United States Patent
Yamamoto et al.

(10) Patent No.: US 6,956,046 B2
(45) Date of Patent: Oct. 18, 2005

(54) 4-HYDROXYPIPERIDINE DERIVATIVES HAVING ANALGESIC ACTIVITY

(75) Inventors: Ichiro Yamamoto, Shinjuku-ku (JP); Kazuyuki Matsuura, Shinjuku-ku (JP); Kazuhiro Suzuki, Shinjuku-ku (JP); Kazuo Kato, Shinjuku-ku (JP); Yasushige Akada, Shinjuku-ku (JP); Hidenori Mochizuki, Shinjuku-ku (JP); Akihito Shimoi, Chitose (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 80 days.

(21) Appl. No.: 10/478,845

(22) PCT Filed: May 17, 2002

(86) PCT No.: PCT/JP02/04815

§ 371 (c)(1), (2), (4) Date: Nov. 25, 2003

(87) PCT Pub. No.: WO02/096875

PCT Pub. Date: Dec. 5, 2002

(65) Prior Publication Data

US 2004/0176410 A1 Sep. 9, 2004

(30) Foreign Application Priority Data

May 25, 2001 (JP) ........................................ 2001-157096

(51) Int. Cl.[7] .................... A61K 31/44; A61K 31/4412; C07D 211/48
(52) U.S. Cl. ...................... 514/327; 546/216; 546/184; 546/192; 546/220
(58) Field of Search ................ 546/216, 184, 546/192, 220; 514/327

(56) References Cited

U.S. PATENT DOCUMENTS 6,255,322 B1 * 7/2001 Welch .......................... 514/312
6,642,257 B2 * 11/2003 Yamamoto et al. ......... 514/327

* cited by examiner

*Primary Examiner*—Ba K. Trinh
(74) *Attorney, Agent, or Firm*—Oliff & Berridge, PLC

(57) ABSTRACT

A compound represented by the following Formula (I):

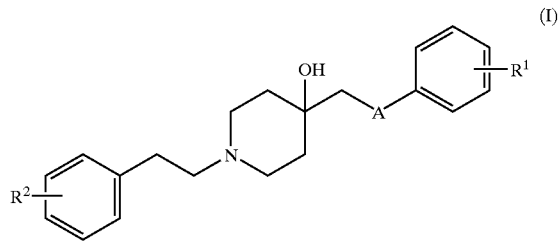

(wherein A represents oxygen atom or —$NR^3$— ($R^3$ represents hydrogen atom or lower alkyl group); $R^1$ represents nitro group, lower alkoxycarbonyl group, carbamoyl group unsubstituted or mono- or di-substituted by lower alkyl group, unprotected or protected hydroxyl group, unprotected or protected carboxyl group, lower alkyl group substituted by unprotected or protected hydroxyl group, or tetrazolyl group; and $R^2$ represents hydrogen atom, cyano group or lower alkylsulfonyl group, provided that when A is —$NR^3$—, it is excluded that $R^1$ represents unprotected or protected hydroxyl group or lower alkyl group substituted by unprotected or protected hydroxyl group) or its salt, and method for producing the compound, and a pharmaceutical composition containing the compound as active ingredient.

10 Claims, No Drawings

# 4-HYDROXYPIPERIDINE DERIVATIVES HAVING ANALGESIC ACTIVITY

TECHNICAL FIELD

The present invention relates to novel 4-hydroxypiperidine derivatives, a method for their manufacture, and pharmaceutical compositions containing, as its active ingredient, at least one of the derivatives, particularly an orally applicable analgesic, and more particularly, an agent for treating neuropathic pain.

BACKGROUND ART

Pain is defined as "an unpleasant sensory and emotional experience associated with actual or potential tissue damage, or described in terms of such damage". Pain is classified into nociceptive pain, neuropathic pain and psycogenic pain.

Nociceptive pain is physiological pain caused by a mechanical stimulus, a temperature stimulus or a chemical stimulus, and plays a role as a biosensor to protect a human body from danger.

Neuropathic pain is caused by a primary damage or by a functional disorder of some part of the neuro-transmission system connecting the periphery to the central nervous system (New Illustrated Anesthetic Science Series, No. 4, "Clinics of Pain Control," 1st Chapter, Written by Kenjiro Dan, 1998, Medical View).

The damage to nerves which becomes a cause to induce the neuropathic pain typically includes traumas and injuries inflicted to the peripheral nervous system, nerve plexus, and soft tissues surrounding the nerves, as well as injuries to the somatesthesia paths in the central nervous system (such as ascending somatesthesia paths found at the levels of spinal cord, brain stem, thalamus and cerebral cortex). For example, neuropathic pain may occur in association with nerve degenerative diseases, bone degenerative diseases, metabolic diseases, cancer, infection, inflammation, post-surgery state, trauma, radiation therapy and anti-cancer chemotherapy, etc. However, the pathophysiology of neuropathic pain, or, especially, molecular mechanisms responsible for its elicitation are not fully clarified yet.

The abnormal reaction against sensation, which is characteristic with neuropathic pain, includes, e.g., allodynia. Allodynia refers to a state in which one feels a pain in the presence of a feeble stimulus which would cause no pain in a normal person. In allodynia, even a gentle tactile stimulus can elicit a pain. Basically this is thought to be accounted for by two factors, namely, a qualitative change in sensory responses and the abnormally lowered sensory threshold. Of the patients with neuralgia subsequent to herpes zoster (postherpetic neuralgia), which is a representative neuropathic disorder, 87% was confirmed to have been affected with allodynia. In addition, it has been said that the severity of pain felt in postherpetic neuralgia is proportional to the severity of allodynia. Allodynia, a pathologic state severely restricting the activity of the patient attracts attention as a target for the treatment of postherpetic neuralgia.

If a patient complains of chronic pain as a result of neuropathy, and is disturbed in his/her everyday activity on account of that pain, relieving him/her of that pain through medication will directly lead to the improvement of his/her quality of life. However, it has been shown that the centrally affecting analgesics represented by morphine, non-steroidal anti-inflammatory agents, or steroids are ineffective for the treatment of neuropathic pain. In the current drug therapy, antidepressants such as amitriptyline, sodium channel blockers such as carbamazepine, anti-epileptic agents such as phenytoin, anti-arrhythmic agents such as mexiletine, etc. are diverted from their respective proper fields to the prescription for the treatment of neuropathic pain. The above therapeutic agents, however, are known to bring about a number of side-effects: amitriptyline may cause thirst, drowsiness, sedation, constipation, dysuria, etc.; carbamazepine and phenytoin may cause gait disorder (staggering), eruption, digestive trouble, harmful effects on cardiac functions, etc.; and mexiletine may cause dizziness, digestive trouble, etc. Those agents which are not specifically intended for the treatment of neuropathic pain are not satisfactory for many neuropathy cases because their therapeutic effects are not sufficiently separated from their side-effects. Accordingly, there is a need for an agent which show high activity via oral administration and is primarily intended for the treatment of neuropathic pain, presenting with few side-effects.

As 4-hydroxypiperidine derivatives, Huegi et al. (J. Med. Chem., 26:42, 1983) reported there are some among them that have a pain-relieving activity. However, the compounds cited by them are centrally affecting pain-relieving agents like morphine which have affinity to the opiate receptors in neurons, and are distinct from the compounds of the present invention in structure. International Publication No. WO 00/61557 discloses 4-hydroxypiperidine derivatives having antiarrhythmic effect and International Publication No. WO 00/61558 discloses 4-hydroxypiperidine derivatives useful as agents for treating neuropathic pain which act on sodium channel and selectively inhibit persistent sodium current in comparison with transient sodium current. However, these products are different from the compounds of the present invention in structure.

As 4-(phenoxymethyl)piperidin-4-ol derivatives, Japanese Patent Application Laid-open No. Sho 60-163861 discloses aryloxymethyl piperidinol derivatives which has antidepressant, antiarrhythimic and hypotensive actions. However, the derivatives of this publication are different from the compounds of the present invention in structure and the publication does not disclose an analgesic activity. International Publication No. WO 93/02052 discloses 2-(4-hydroxypiperidino)-1-alkanol derivatives as an anti-ischemic agent. However, the derivatives of this publication are different from the compounds of the present invention in basic structure and the publication does not disclose an analgesic activity.

Not only desired pharmaceutical activities but also long-term safety are required in the development of medicines. In addition, severe criteria in various tests on absorption, distribution, metabolism and excretion should be satisfied. For example, problems to be examined and solved include drug interation, desentitization and tolerance, absorption at the digestive tract after oral administration, transfer rate into the small intestines, absorption rate and first pass effect, internal organ barrier, binding to proteins, induction of drug metabolizing enzymes, the excretion pathway, clearance in the body and the methods of application (application sites, methods and objects). However, compounds satisfying all these requirements can be seldom found. Therefore, agents having wide safety area and excellent pharmacokinetic property have been desired.

Agents for treating neuropathic pain also involve such general problems as described above in developing as medicine. In addition, with respect to the agents for treating neuropathic pain, agents for having less side-effects mentioned above and having high utility has been sought in comparison with the conventional sodium channel blocking agents which have been now used as the treatment of neuropathic pain.

The problems to be solved by the present invention is to provide analgesics which are applicable orally, have high safety and are excellent in effectiveness and pharmacokinetic property, especially novel compounds which are useful for an agent for treating neuropathic pain.

DISCLOSURE OF INVENTION

The present inventors had intensively studied to solve the above problem and to obtain compounds which have high safety, excellent action to relieve pain and pharmacokinetic property. As a result, they found that 4-hydroxypiperidine derivative, as represented by Formula (I), having, at 4-position, methyl group substituted by hetero atom to which aryl group having specific substituent and its salt are highly effective for the treatment of pain, and especially that those substances are effective for the treatment of neuropathic pain by selectively acting on injured sites. These findings led to the present invention.

Specifically, the inventors found that the compound as represented by Formula (I) has at least one of the following properties: (1) to have excellent activity to suppress painful response in the formalin test; (2) to selectively raise the reaction threshold to a mechanical stimulus applied on the injured side in a model of neuropathy made by loosely constricting the sciatic nerve (selective anti-allodynia activity); (3) to present with comparatively less side-effects and high safety; and (4) and moreover, to be excellent in pharmacokinetic property. Particularly, the compound represented by Formula (I) is highly effective for the treatment of neuropathic pain even when applied orally.

The first embodiment of the present invention is a compound represented by the following Formula (I):

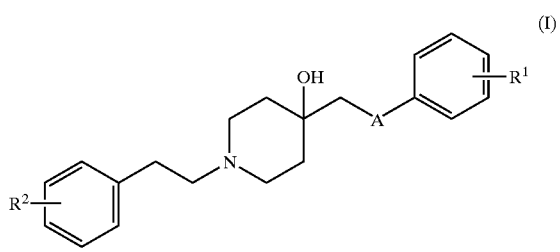

(wherein A represents oxygen atom or —NR$^3$— (R$^3$ represents hydrogen atom or lower alkyl group); R$^1$ represents nitro group, lower alkoxycarbonyl group, carbamoyl group unsubstituted or mono- or di-substituted by lower alkyl group, unprotected or protected hydroxyl group, unprotected or protected carboxyl group, lower alkyl group substituted by unprotected or protected hydroxyl group, or tetrazolyl group; and R$^2$ represents hydrogen atom, cyano group or lower alkylsulfonyl group, provided that when A is —NR$^3$—, it is excluded that R$^1$ represents unprotected or protected hydroxyl group or lower alkyl group substituted by unprotected or protected hydroxyl group), and its pharmaceutically acceptable salt.

For the compound represented by Formula (I), preferred substitutents and their preferred combinations will be introduced below, but this invention should not be limited to those examples.

R$^1$ preferably represents nitro group, lower alkoxycarbonyl group, carbamoyl group unsubstituted or mono- or di-substituted by lower alkyl groups, unprotected or protected carboxyl group, or tetrazolyl group, more preferably represents carboxyl group.

R$^1$ is substituted at ortho-, meta- or para-position with respect to carbon atom to which A bonds, preferably substituted at para-position (4th position).

As R$^1$, carboxyl group bonded to para-position of A is more preferable.

R$^2$ preferably represents cyano group.

R$^2$ is substituted at ortho-, meta- or para-position with respect to carbon atom to which ethyl of phenethyl group bonds, preferably substituted at para-position.

R$^2$ preferably represents cyano group bound to para-position.

A preferably represents —NR$^3$—.

R$^3$ preferably represents lower alkyl group, more preferably represents methyl group or ethyl group.

The compounds of the present invention can be represented by Formula (I), and concrete example of compounds having combinations of more preferable substituents are as follows:

They are compounds or their salts wherein R$^1$ is carboxyl group and R$^2$ represents cyano group in Formula (I). The Formula (I) in this case is also represented by the following Formula (II).

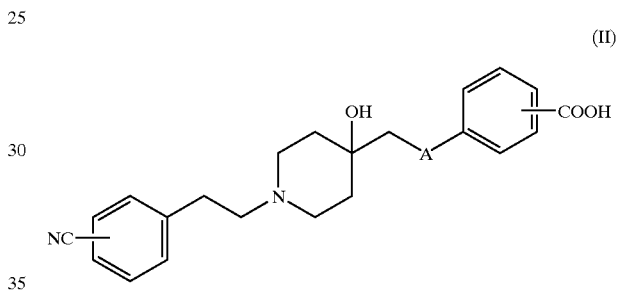

(wherein A has the same meaning as defined above).

The second embodiment of the present invention is a pharmaceutical composition containing, as its active ingredient, a compound represented by Formula (I) or Formula (II), or a pharmaceutically acceptable salt thereof.

The third embodiment of this invention is an analgesic which contains, as its active ingredient, a compound represented by Formula (I) or Formula (II), or a pharmaceutically acceptable salt thereof, and an orally applicable analgesic. An agent useful for the treatment of neuropathic pain and an orally applicable agent useful for the treatment of neuropathic pain are preferable.

The fourth embodiment of this invention is an allodynia treating agent which contains, as its active ingredient, a compound represented by Formula (I) or Formula (II), or a pharmaceutically acceptable salt thereof.

According to different embodiments of the third and fourth embodiments, the following uses or methods are provided: use of a substance containing at least one of the compound represented by the Formula (I) and the compound represented by Formula (II) for manufacturing an analgesic or an orally applicable analgesic, more preferably an agent for the treatment of neuropathic pain or an orally applicable agent useful for the treatment of neuropathic pain, and pharmaceutically acceptable salt thereof; use of a substance containing at least one of the compound represented by the Formula (I) for manufacturing allodynia treating agent, the pharmaceutically acceptable salt thereof, the compound represented by Formula (II) for manufacturing allodynia treating agent and the pharmaceutically acceptable salt thereof; and a method for preventing and treating pain, more preferably neuropathic pain which contains a step of administering a substance selected from a group of the compound represented by the Formula (I), the compound represented by Formula (II) and each pharmaceutically acceptable salt thereof to mammal inclusive of human being, more preferably a step of orally administering it; and a method for preventing and treating allodynia which contains a step of administering a substance selected from a group of the compound represented by the Formula (I), the pharmaceutically acceptable salt thereof, the compound represented by Formula (II) and the pharmaceutically acceptable salt thereof to mammal inclusive of human being, more preferably a step of orally administering it.

The fifth embodiment of this invention is a method for manufacturing a compound represented by Formula (I):

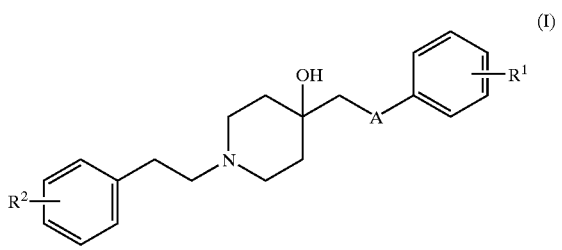

(I)

(wherein A, $R^1$ and $R^2$ have the same meanings as defined above), or a salt thereof and which uses the following Process (a), Process (b), Process (c), Process (d), Process (e) and Process (f).

Process (a)

Process for adding a compound represented by the Formula (XIV):

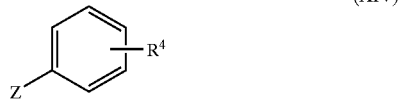

(XIV)

(wherein $R^4$ represents nitro group, lower alkoxycarbonyl group, carbamoyl group unsubstituted or mono- or di-substituted by lower alkyl group, unprotected or protected hydroxyl group, unprotected or protected carboxyl group, lower alkyl group substituted by unprotected or protected hydroxyl group, tetrazolyl group, cyano group or formyl group, and Z represents hydroxyl group or amino group unsubstituted or substituted by lower alkyl group or lower alkanoyl group) to a compound represented by the Formula (III):

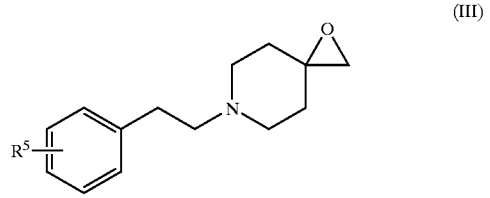

(III)

(wherein $R^5$ represents hydrogen atom, cyano group, lower alkylsulfonyl group or halogen atom), and then converting the lower alkanoyl group to lower alkyl group by reducing reaction when that Z represents amino group substituted by lower alkanoyl group, and converting, as needed, $R^4$ to $R^1$ and $R^5$ to $R^2$.

Process (b)

Process for adding a compound represented by the Formula (XIV):

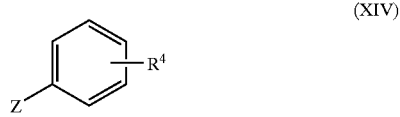

(XIV)

(wherein $R^4$ and Z have the same meanings as defined above) to a compound represented by Formula (IV):

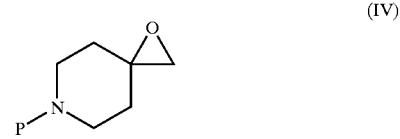

(IV)

(wherein P represents protecting group used for amino group) and converting, as needed, lower alkanoyl group to lower alkyl group by reducing reaction when that Z represents amino group substituted by lower alkanoyl group, followed by deprotection reaction to obtain a compound represented by Formula (VI):

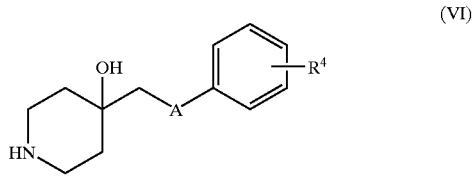

(VI)

(wherein $R^4$ has the same meaning as defined above, A' represents oxygen atom or —$NR^6$— ($R^6$ represents hydrogen atom, lower alkyl group or lower alkanoyl group), which is allowed to react with a compound represented by Formula (VII):

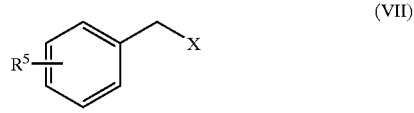

(VII)

(wherein X represents halogenated methyl group, methanesulfonyloxymethyl group, arylsulfonyloxymethyl group such as p-toluenesulfonyloxymethyl group, formyl group or carboxyl group, and $R^5$ has the same meaning as defined above) in the presence or absence of a base when X represents halogenated methyl group, methanesulfonyloxymethyl group or arylsulfonyloxymethyl group, in the presence or absence of acid catalyst under reducing conditions when X represents formyl group, or by using a condensation agent when X represents carboxyl group, followed by conducting reducing reaction, and converting, as needed, $R^4$, $R^5$ and $R^6$ to $R^1$, $R^2$ and $R^3$, respectively, in the obtained compound.

Process (c)

Process for reacting a compound represented by the Formula (VIII):

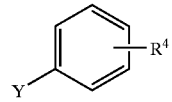
(VIII)

(wherein R⁴ has the same meaning as defined above, and Y represents halogen atom such as F, etc.) with a compound represented by Formula (IX):

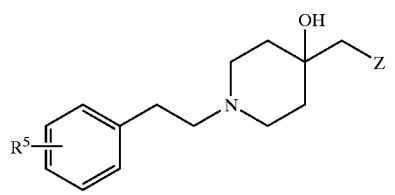
(IX)

(wherein R⁵ and Z have the same meanings as defined above), followed by converting lower alkanoyl group to lower alkyl group by reducing reaction when Z represents amino group substituted by lower alkanoyl group, and converting, as needed, R⁴ to R¹ and R⁵ to R².

Process (d)

Process for reacting a compound represented by the Formula (VIII):

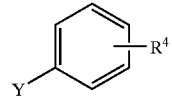
(VIII)

(wherein R⁴ and Y have the same meanings as defined above) with a compound represented by Formula (X):

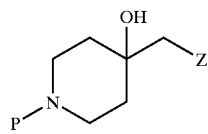
(X)

(wherein P and Z have the same meanings as defined), followed by deprotection reaction to obtain a compound represented by Formula (VI):

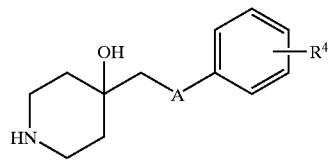
(VI)

(wherein R⁴ hand A' have the same meanings as defined above) which is allowed to react with a compound represented by Formula (VII):

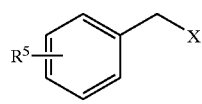
(VII)

(wherein X and R⁵ have the same meanings defined above) in the presence or absence of a base when X represents halogenated methyl group, methanesulfonyloxymethyl group and arylsulfonyloxymethyl group, in the presence or absence of acid catalyst under reducing conditions when X represents formyl group, or by using a condensation agent when X represents carboxyl group, followed by conducting reducing reaction, converting lower alkanoyl group to lower alkyl group when R⁶ is lower alkanoyl group, and converting, as needed, R⁴, R⁵ and R⁶ to R¹, R² and R³, respectively, in the obtained compound.

Process (e)

Process for reacting a compound represented by the Formula (XV):

(XV)

(wherein R³ and R⁴ have the same meanings as defined above) with a compound represented by the Formula (XVI):

(XVI)

(wherein R⁵ and X have the same meanings as defined above), and converting, as needed, R⁴ to R¹ and R⁵ to R².

Process (f)

Process for reacting a compound represented by the Formula (XV):

(XV)

(wherein R³ and R⁴ have the same meanings as defined above) with a compound represented by Formula (XVII):

(XVII)

(wherein P and X have the same meanings as defined above), followed by deprotection reaction to obtain a compound represented by Formula (XIX):

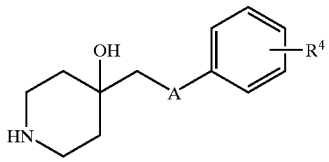
(XIX)

(wherein $R^4$ and A have the same meanings as defined above) which is allowed to react with a compound represented by Formula (VII):

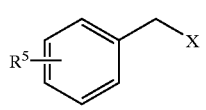
(VII)

(wherein X and $R^5$ have the same meanings defined above) in the presence or absence of a base when X represents halogenated methyl group, methanesulfonyloxymethyl group and arylsulfonyloxymethyl group, in the presence or absence of acid catalyst under reducing conditions when X represents formyl group, or by using a condensation agent when X represents carboxyl group, and converting, as needed, $R^4$ and $R^5$ to $R^1$ and $R^2$, respectively.

BEST MODE FOR CARRYING OUT THE INVENTION

This invention will be described in detail below. The compound of the present invention is a compound represented by the following Formula (I):

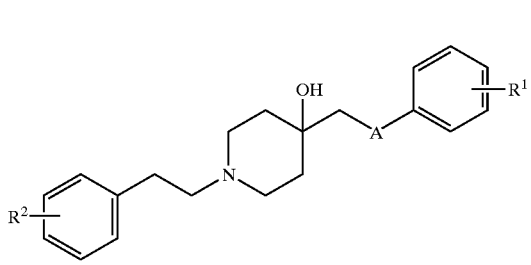
(I)

(wherein A represents oxygen atom or —$NR^3$— ($R^3$ represents hydrogen atom or lower alkyl group); $R^1$ represents nitro group, lower alkoxycarbonyl group, carbamoyl group unsubstituted or mono- or di-substituted by lower alkyl group, unprotected or protected hydroxyl group, unprotected or protected carboxyl group, lower alkyl group substituted by unprotected or protected hydroxyl group, or tetrazolyl group; and $R^2$ represents hydrogen atom, cyano group or lower alkylsulfonyl group, provided that when A is —$NR^3$—, it is excluded that $R^1$ represents unprotected or protected hydroxyl group or lower alkyl group substituted by unprotected or protected hydroxyl group) and its salt.

The groups described in the formula in this invention are defined as follows.

The "lower" means a straight, branched or cyclic carbon chain containing one to four carbons unless otherwise stated, and is expressed as "C1–4", preferably "C1–2", more preferably "C1". Accordingly, the "lower alkyl group" includes a methyl group, ethyl group, propyl group, isopropyl group, cyclopropyl group, butyl group, isobutyl group, sec-butyl group, tert-butyl group, cyclobutyl group, etc., preferably methyl group or ethyl group, more preferably methyl group.

The "lower alkoxycarbonyl group" means C1–4 alkoxycarbonyl group which has one of 1 to 4 carbon atoms in carbon atom number of alkoxy group, and includes methoxycarbonyl group, ethoxycarbonyl group, propoxycarbonyl group, isopropoxycarbonyl group, cyclopropyloxycarbonyl group, butoxycarbonyl group, isobutoxycarbonyl group, sec-butoxycarbonyl group, tert-butoxycarbonyl group, cyclobutyloxycarbonyl group, etc. C1–2 alkoxycarbonyl group (methoxycarbonyl group or ethoxycarbonyl group) are preferable, and C1 alkoxycarbonyl group (methoxycarbonyl group) is more preferable.

The "carbamoyl group unsubstituted or mono- or di-substituted by lower alkyl group" means carbamoyl group of which one or two hydrogen atoms bound on nitrogen atom may be substituted by the aforementioned "lower alkyl group." Specifically, it includes carbamoyl group, methylcarbamoyl group, ethylcarbamoyl group, propylcarbamoyl group, isopropylcarbamoyl group, cyclopropylcarbamoyl group, butylcarbamoyl group, isobutylcarbamoyl group, sec-butylcarbamoyl group, tert-butylcarbamoyl group, cyclobutylcarbamoyl group, dimethylcarbamoyl group, diethylcarbamoyl group, dipropylcarbamoyl group, diisopropylcarbamoyl group, dicyclopropylcarbamoyl group, dibutylcarbamoyl group, diisobutylcarbamoyl group, disec-butylcarbamoyl group, ditert-bytylcarbamoyl group, dicyclobutylcarbamoyl group, ethylmethylcarbamoyl group, methylpropylcarbamoyl group, ethylpropylcarbamoyl group, butylmethylcarbamoyl group, butylethylcarbamoyl group, butylpropylcarbamoyl group, etc., preferably carbamoyl group and carbamoyl group mono- or di-substituted by C1–2 alkyl group (e.g., methylcarbamoyl group, ethylcarbamoyl group, dimethylcarbamoyl group and diethylcarbamoyl group), and more preferably carbamoyl group and carbamoyl group di-substituted by C1–2 alkyl group (e.g., dimethylcarbamoyl group and diethylcarbamoyl group), The protective group used in "unprotected or protected hydroxyl group" as described in this specification includes alkyl protective groups such as a methyl group, tert-butyl group, benzyl group, trityl group, methoxymethyl group, etc.; silyl protective groups such as a trimethylsilyl group, tert-butyldimethylsilyl group, etc.; acyl protective groups such as formyl group, acetyl group, benzoyl group, etc.; and carbonate protective groups such as methoxycarbonyl group, benzyloxycarbonyl group, etc.

The protective group used in "unprotected or protected carboxyl group" as described in this specification includes alkyl ester protective groups such as a methyl group, ethyl group, tert-butyl group, benzyl group, diphenylmethyl group, trityl group, etc.; and silyl ester protective groups such as a trimethylsilyl group, tert-butyldimethylsilyl butyldimethylsilyl group, etc.

The "lower alkyl substituted by unprotected or protected hydroxyl group" includes a case that the above-mentioned lower alkyl group is substituted by hydroxyl group. Specifically, "C1–4 alkyl group substituted by unprotected or protected hydroxyl group" includes hydroxymethyl group, 1-hydroxyethyl group, 2-hydroxylethyl group, 1-hydorxy-1-methylethyl group, 1-hydroxypropyl group, 2-hydroxypropyl group, 3-hydroxypropyl group, 1-hydroxyl-1-methylpropyl group, 1-hydroxybutyl group, 2-hydroxybutyl group, 3-hydroxybutyl group, 4-hydroxybutyl group, 1-hydroxylcyclopropyl group, 1-hydoxycyclopropylmethyl group, etc. C1–2 alkyl group substituted by hydroxyl group (e.g., hydroxymethyl group, 1-hydroxyethyl group, 2-hydroxyethyl group) is preferable, and C1 alkyl group substituted by hydroxyl group (e.g., hydroxymethyl group) is more preferable.

The "lower alkylsulfonyl group" means —SO$_2$— (C1–4 alkyl group) and can be expressed as "C1–4 alkylsulfonyl group". Example of the lower alkylsulfonyl group are methysulfonyl group, ethylsulfonyl group, propylsulfonyl group, isopropylsulfonyl group, butylsulfonyl group, isobutylsulfonyl group, sec-butylsulfonyl group, tert-butylsulfonyl group, etc. C1–2 alkylsufonyl group (e.g., methylsulfonyl group, ethylsulfonyl group) is preferable, and C1 alkylsulfonyl group (methylsulfonyl group) is more preferable.

The "lower alkanoyl group" includes formyl group, acetyl group, propionyl group, etc.

The preferred substituents for the compound of the present invention are as follows.

$R^1$ preferably represents nitro group, lower alkoxycarbonyl group, carbamoyl group unsubstituted or mono- or di-substituted by lower alkyl groups, unprotected or protected carboxyl group or tetrazolyl group, more preferably represents nitro group, methoxycarbonyl group, ethoxycarbonyl group, carbamoyl group, dimethylcarbamoyl group, diethylcarbamoyl group, carboxyl group or tetrazolyl group, and furthermore preferably represents carboxyl group.

$R^1$ is preferably substituted at ortho-, meta- or para-position with respect to carbon atom to which A bonds, more preferably substituted at para-position (4th position).

As $R^1$, carboxyl group bound to para-position of A is more preferable.

$R^2$ preferably represents cyano group or lower alkylsulfonyl group, more preferably represents cyano group, methylsulfonyl group, ethylsulfonyl group propylsulfonyl group, isopropylsulfonyl group or butylsulfonyl group, and furthermore preferably represents cyano group.

$R^2$ is preferably substituted at ortho-, meta- or para-position with respect to carbon atom to which ethyl of phenethyl group bonds, is preferably substituted at para-position.

$R^2$ preferably represents cyano group bound to para-position.

A preferably represents —NR$^3$—.

$R^3$ preferably represents lower alkyl group, more preferably represents methyl group or ethyl group.

In addition to the compounds of the present invention represented by Formula (I), examples of compounds having furthermore preferable substituents are as follows.

It is a compound wherein $R^1$ presents carboxyl group and $R^2$ represents cyano group in Formula (I), or its salt. The Formula (I) in this case may be represented by Formula (II)

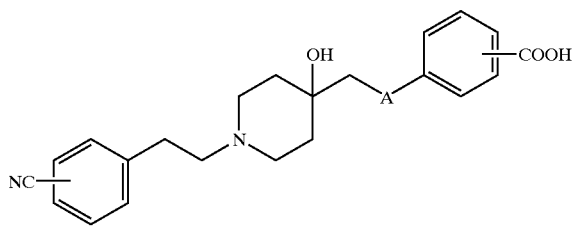

(II)

(wherein A has the same meaning as defined above).

The preferred compound includes followings:
1-[2-(4-cyanophenyl)ethyl]-4-(4-nitrophenoxymethyl)piperidin-4-ol;
1-[2-(4-cyanophenyl)ethyl]-4-(4-hydroxyphenoxymethyl)piperidin-4-ol;

4-(4-carbamoylphenoxymethyl)-1-[2-(4-cyanophenyl)ethyl]piperidin-4-ol;
methyl 4-{1-[2-(4-cyanophenyl)ethyl]-4-hydroxypiperidin-4-ylmethoxy}benzoate;
4-{1-[2-(4-cyanophenyl)ethyl]-4-hydroxypiperidin-4-ylmethoxy}benzoic acid;
1-[2-(4-cyanophenyl)ethyl]-4-(4-hydroxymethylphenoxymethyl)piperidin-4-ol;
methyl 4-({1-[2-(4-cyanophenyl)ethyl]-4-hydroxypiperidin-4-ylmethyl}methylamino)benzoate;
4-({1-[2-(4-cyanophenyl)ethyl]-4-hydroxypiperidin-4-ylmethyl}methylamino)benzoic acid;
4-({1-[2-(3-cyanophenyl)ethyl]-4-hydroxypiperidin-4-ylmethyl}methylamino)benzoic acid;
4-({1-[2-(2-cyanophenyl)ethyl]-4-hydroxypiperidin-4-ylmethyl}methylamino)benzoic acid;
3-({1-[2-(4-cyanophenyl)ethyl]-4-hydroxypiperidin-4-ylmethyl}methylamino)benzoic acid;
2-({1-[2-(4-cyanophenyl)ethyl]-4-hydroxypiperidin-4-ylmethyl}methylamino)benzoic acid;
4-[2-(4-hydroxy-4-{[methyl(4-nitrophenyl)amino]methyl}piperidin-1-yl)ethyl]benzonitrile;
4-{2-[4-hydroxy-4-({methyl[4-(1H-tetrazol-5-yl)phenyl]amino}methyl)piperidin-1-yl]ethyl}benzonitrile;
4-({1-[2-(4-cyanophenyl)ethyl]-4-hydroxypiperidin-4-ylmethyl}amino)benzoic acid;
4-({4-hydroxy-1-[2-(4-methanesulfonylphenyl)ethyl]piperidin-4-ylmethyl}methylamino)benzoic acid; and
4-[(4-hydroxy-1-phenethylpiperidin-4-ylmethyl)methylamino]benzoic acid.

These compounds can form the salts described below.

The compound (I) of this invention may form acid addition salts, or may form salts with bases, depending on the kind of its substituents. The salts are not limited to any specific ones, as long as they are pharmaceutically acceptable. Specifically, they include acid-bound salts, the acid being mineral acid such as hydrochloric acid, hydrobromic acid, hydroiodic acid, sulfuric acid, nitric acid, phosphoric acid, etc.; organic carboxylic acid such as aliphatic monocarboxylic acid such as formic acid, acetic acid, propionic acid, butyric acid, valeric acid, enanthic acid, capric acid, myristic acid, palmitic acid, stearic acid, lactic acid, sorbic acid, mandelic acid, etc., aromatic monocarboxylic acid such as benzoic acid, salicylic acid, etc., aliphatic dicarboxylic acid such as oxalic acid, malonic acid, succinic acid, fumalic acid, maleic acid, malic acid, tartaric acid, etc.; organic tricarboxylic acid such as citric acid, etc.; organic sulfonic acid such as aliphatic sulfonic acid such as methanesulfonic acid, ethanesulfonic acid, 2-hydroxyethanesulfonic acid, etc., aromatic sulfonic acid such as benzenesulfonic acid, p-toluenesulfonic acid, etc.; acid addition salt with amino acid such as aspartic acid, glutamic acid, etc. and slats with metal of alkali metal or alkaline earth metal such as sodium, potassium, magnesium, calcium or aluminum, slats with organic bases such as methylamine, ethylamine, ethanolamine, pyridine, lysine, arginine, ornithine, etc.; or ammonium salts.

The above salt can be prepared according to convention: for example, the compound of the present invention and a solution containing a desired acid or base at equivalent amounts are mixed and the resulting salt is collected by filtration or by distilling off a solvent. Further, the compound of this invention or its salts can form solvate in the presence of a solvent such as water, ethanol, glycerol, etc.

The salts of the compounds of the present invention may contain mono- or di-salts. The compounds of the present invention may simultaneously form both acid addition salt and salt with a base depending on the substituent on the side chains of the compounds.

Moreover, the present invention includes hydrates, various pharmaceutically acceptable solvate and polymorphic crystals of compound (I). Naturally, the present invention is not limited to the compounds mentioned in the Examples below, but include all the compounds represented by Formula (I), and their pharmaceutically acceptable salts.

Next, the method for manufacturing the compound of this invention will be disclosed and the processes involved therein will be described. The definitions of A, A', $R^1$, $R^2$, $R^3$, $R^4$, $R^5$, $R^6$, P, X, Y and Z in Formulas (I), (V), (VI), (VIII) and (XIX) cited in the Reaction Schemes and the description of Manufacturing Methods 1 to 3 are the same meanings as above, unless otherwise stated.

The compound of the present invention represented by Formula (I), or its salts can be prepared according to Manufacturing Methods 1 to 3 described below or to their modifications from compounds as represented by Formula (XIV) (wherein $R^4$ and Z have the same meanings as defined above), Formula (III), Formula (IV) (wherein P has the same meaning as defined above), Formula (VII) (wherein X has the same meaning as defined above), Formula (VII) (wherein $R^4$ and Y have the same meanings as defined above), Formula (IX), Formula (X) (wherein P has the same meaning as defined above), Formulae (XV), (XVI) and (XVII), which may be synthesized starting from the compounds known in the art or from commercially available compounds. The definitions of A, A', $R^1$, $R^2$, $R^3$, $R^4$, $R^5$, $R^6$, P, X, Y and Z in the Formulae are the same meanings as above, unless otherwise stated. As starting material, intermediate material and product of each process, the salt of a relevant compound may be used as needed.

Next, the manufacturing processes will be described in detail.

<Manufacturing Method 1>

It is possible to prepare a compound represented by Formula (I) or its salt, from a compound represented by Formula (XIV), and another compound represented by Formula (III) or Formula (IV), by employing appropriate processes cited in Reaction Scheme 1.

REACTION SCHEME 1

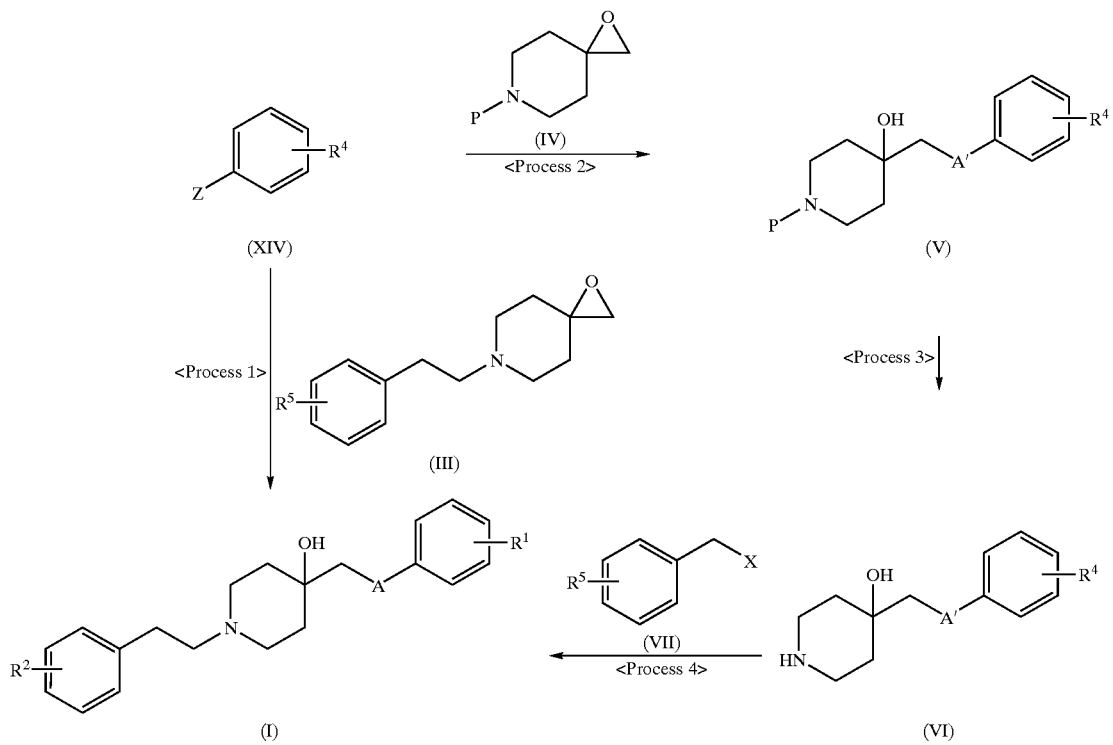

<Process 1>

The compound represented by Formula (I) or its salt can be manufactured from a compound represented by Formula (XIV) and the compound represented by Formula (III). The compound represented by Formula (XIV) and the compound represented by Formula (III) are reacted in a solvent not interfering with the reaction, for example, chosen from the group comprising halogenated hydrocarbon solvents such as methylene chloride, chloroform, etc., ether solvents such as diethyl ether, tetrahydrofuran, etc., hydrocarbon solvents such as toluene, benzene, hexane, etc., and polar solvents such as dimethylformamide, dimethyl sulfoxide, etc. and acetonitrile, etc. or without using a solvent, in the presence or absence of an acid catalyst containing Lewis acid such as lithium perchlorate, scandium (III) trifluoromethanesulfonate, etc., or in the presence or absence of a base and in the presence or absence of crown ether such as 18-Crown-6, etc. at a temperature between 0° C. and the temperature at which the reaction mixture will reflux, followed by converting lower alkanoyl group to lower alkyl group by reducing reaction when Z represents amino group substituted by lower alkanoyl group and then, by converting, as needed, $R^4$ to $R^1$ and $R^5$ to $R^2$. The compound represented by Formula (I) can be also manufactured by reacting the compound represented by Formula (XIV) and the compound represented by Formula (III) in diethyl ether in the presence of a neutral alumina at room temperature, according to the method described in Gary H. Posner et al., Journal of the American Chemical Society, 99, 8208–8214 (1977), followed by converting lower alkanoyl group to lower alkyl group by reducing reaction when Z represents amino group substituted by lower alkanoyl group and then, converting, as needed, $R^4$ to $R^1$ and $R^5$ to $R^2$. The compound represented by Formula (I) can be also manufactured by reacting the compound represented by Formula (XIV) or the salt thereof, and the compound represented by Formula (III) or the salt thereof by a solvent not interfering with the reaction such as alcoholic solvent such as methanol, ethanol, etc. or water, etc. in the presence or absence of cyclodextrins such as β-cyclodextrin, followed by converting lower alkanoyl group to lower alkyl group by reducing reaction when Z represents amino group substituted by lower alkanoyl group and then, converting, as needed, $R^4$ to $R^1$ and $R^5$ to $R^2$.

It is also possible to obtain the compound represented by Formula (I) according to Processes 2, 3 and 4 described below.

<Process 2>

It is possible to prepare the compound represented by Formula (V) (wherein $R^4$ and P have the same meanings as defined above) from the compound represented by Formula (XIV) and the compound represented by Formula (IV) according to Process 1. The protective group P includes alkyl protective groups such as benzyl group, trityl group, methoxymethyl group, etc., and carbamate protective groups such as tert-butoxycarbonyl group, benzyloxycarbonyl group, etc., as described in T. W. Greene and P. G. M. Wuts (eds.), "Protective Groups in Organic Synthesis," 3rd Ed., John Wiley and Sons, 1999.

<Process 3>

It is possible to obtain the compound represented by Formula (VI) (wherein $R^4$ has the same meaning as defined above) by removing the protective group at the 1st position of piperidine from the compound represented by Formula (V).

Removal of the protective group at the 1st position of piperidine from the compound represented by Formula (V) may be achieved by the method introduced in the above review, i.e., "Protective Groups in Organic Synthesis," 3rd Ed., 1999. For example, when the protective group P is a benzyl group, benzyloxycarbonyl group or the like, removal of the protective group will be achieved by placing the compound in an alcoholic solvent such as methanol, ethanol, etc., or solvents such as ethyl acetate, acetic acid, water, etc. under hydrogen atmosphere, or in the presence of ammonium formate in the presence of a catalyst such as palladium on carbon, platinum oxide, etc., at a temperature between 0° C. and the temperature at which the reaction mixture will reflux. Then, the compound represented by Formula (VI) will be obtained. When the protective group P is tert-butoxycarbonyl group, etc., removal of the protective group will be achieved by placing the compound in acid such as trifluoroacetic acid, hydrochloric acid, etc., in the presence or absence of anisole at a temperature between 0° C. and the temperature at which the reaction mixture will reflux. Then, the compound represented by Formula (VI) will be obtained.

<Process 4>

It is possible to allow the compound represented by Formula (VI) to react with the compound represented by Formula (VII) according to the method described below appropriately chosen depending on the sorts of X. The compound represented by Formula (I) or its salt can be manufactured by converting $R^4$, $R^5$ and $R^6$ to $R^1$, $R^2$ and $R^3$, respectively, in the obtained compound.

(Method A)

If X represents halogenated methyl group, methanesulfonyloxymethyl group, or arylsulfonyloxymethyl group such as p-toluenesulfonyloxymethyl group, the compound represented by Formula (VI) and the compound represented by Formula (VII) are reacted in a solvent not interfering with the reaction, for example, halogenated hydrocarbon solvents such as methylene chloride, chloroform, etc., ether solvents such as diethyl ether, tetrahydrofuran, etc., hydrocarbon solvents such as toluene, benzene, hexane, etc., and polar solvents such as dimethylformamide, dimethyl sulfoxide, etc., in the presence or absence of an organic base such as triethylamine, pyridine, etc., or in the presence or absence of an inorganic base such as potassium carbonate, etc., at a temperature between 0° C. and the temperature at which the reaction mixture will reflux, followed by converting, as needed, $R^4$, $R^5$ and $R^6$ to $R^1$, $R^2$ and $R^3$, respectively, in the obtained compound. Then, the compound represented by Formula (I) will be obtained. When X represents halogenated methyl group, sodium iodide may be used as a catalyst.

(Method B)

When X represents formyl group, the compounds represented by Formula (VI) and the compound represented by Formula (VII) are reacted in a solvent, for example, chosen from the group comprising aromatic hydrocarbon solvents such as toluene, benzene, etc., halogenated hydrocarbon solvents such as methylene chloride, chloroform, etc., and alcoholic solvents such as methanol, ethanol, etc., in the presence or absence of an acidic catalyst such as acetic acid, hydrochloric acid, etc., in combination with an appropriate reducing agent, followed by converting, as needed, $R^4$, $R^5$ and $R^6$ to $R^1$, $R^2$ and $R^3$, respectively, in the obtained compound. Then, the compound represented by Formula (I) will be obtained. Generally speaking, for this reaction, any reducing agent that can reduce imino group into amino group is applicable, the preferred reducing agent includes sodium triacetoxyborohydride, sodium borohyd ride, lithium borohydride, diisobutylaluminum hydride, sodium cyanoborohyd ride, etc. The reducing reaction may proceed at a temperature between –78° C. and room temperature, preferably at room temperature, for a period in which reaction will proceed sufficiently, specifically, a period between three and twelve hours.

(Method C)

When X represents carboxyl group, it is possible to prepare the compound represented by Formula (I) or its salt by reacting the compounds represented by Formula (VI) and the compound represented by Formula (VII) in a solvent not interfering with the reaction, for example, chosen from the group comprising halogenated hydrocarbon solvents such as methylene chloride, chloroform, etc., ether solvents such as diethyl ether, tetrahydrofuran, etc., hydrocarbon solvents such as toluene, benzene, hexane, etc., and polar solvents such as dimethylformamide, dimethyl sulfoxide, etc., in the presence of a condensing agent such as 1-ethyl-3-(3-dimehtylaminopropyl)carbodiimide hydrochloride (water soluble carbodiimide hydrochloride, WSC.HCl) or dicyclohexylcarbodiimide (DCC), at a temperature between 0° C. and the temperature at which the reaction mixture will reflux to synthesize amide compound, and reacting the prepared amide bond with a reducing agent such as lithium aluminum hydride or diisobutylaluminum hydride, or a borane com plex represented by borane-methyl sulfide complex or borane-tetrahydrofuran complex, in a solvent not interfering with the reaction, for example, chosen from the group comprising ether solvents such as diethyl ether, tetrahydrofuran, etc., and aromatic hydrocarbon solvents such as toluene, benzene, etc., at a temperature between 0° C. and the temperature at which the reaction mixture will reflux, followed by converting, as needed, $R^4$, $R^5$ and $R^6$ to $R^1$, $R^2$ and $R^3$, respectively, in the obtained compound.

The reaction between the compound represented by Formula (VI) and the compound represented by Formula (VII) can be conducted in a solvent not interfering with the reaction, for example, chosen from the group comprising halogenated hydrocarbon solvents such as methylene chloride, chloroform, etc., ether solvents such as diethyl ether, tetrahydrofuran, etc., and hydrocarbon solvents such as toluene, benzene, hexane, etc., in the presence of a dehydrating agent such as phosphorus oxychloride and of a base such as pyridine, triethylamine, etc., at a temperature between –20° C. and the temperature at which the reaction mixture will reflux.

The reaction between the compound represented by Formula (VI) and the compound represented by Formula (VII) can be conducted by converting the compound represented by Formula (VII) into its acid chloride using thionyl chloride, etc., and then by allowing the acid chloride to react in a solvent chosen from the group comprising halogenated hydrocarbon solvents such as methylene chloride, chloroform, etc., ether solvents such as diethyl ether, tetrahydrofuran, etc., hydrocarbon solvents such as toluene, benzene, hexane, etc. or basic solvents such as pyridine, triethylamine, etc. in the presence of organic base such as triethylamine, pyridine, etc. or an inorganic base such as potassium carbonate, etc., at a temperature between –20° C. and the temperature at which the reaction mixture will reflux.

<Manufacturing Method 2>

It is possible to prepare the compound represented by Formula (I) or its salt from a compound represented by Formula (VIII) and a compound represented by Formula (IX) or a compound represented by Formula (X), by employing appropriate processes cited in Reaction Scheme 2.

REACTION SCHEME 2

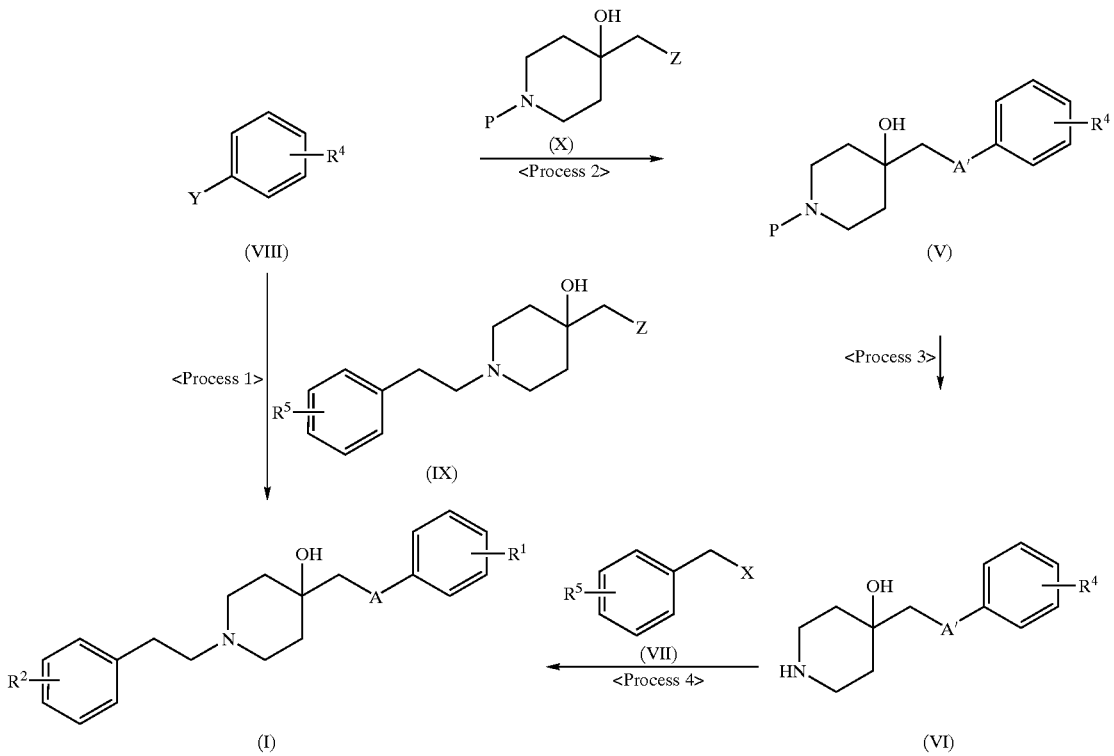

<Process 1>

The compound represented by Formula (I) or its salt can be manufactured by reacting the compound represented by Formula (VIII) and the compound represented by Formula (IX) in a solvent not interfering with the reaction, for example, chosen from the group comprising halogenated hydrocarbon solvents such as methylene chloride, chloroform, etc., ether solvents such as diethyl ether, tetrahydrofuran, etc., hydrocarbon solvents such as toluene, benzene, hexane, etc., and polar solvents such as dimethylformamide, dimethyl sulfoxide, etc. or without using a solvent, in the presence or absence of a base catalyst at a temperature between 0° C. and the temperature at which the reaction mixture will reflux, followed by converting, as needed, $R^4$, $R^5$ and $R^6$ to $R^1$, $R^2$ and $R^3$, respectively.

It is also possible to obtain the compound represented by Formula (I) or its salt according to Processes 2, 3 and 4 described below.

<Process 2>

It is possible to prepare the compound represented by Formula (V) by reacting the compound represented by Formula (VIII) and the compound represented by Formula (X) in a solvent not interfering with the reaction, for example, chosen from the group comprising halogenated hydrocarbon solvents such as methylene chloride, chloroform, etc., ether solvents such as diethyl ether, tetrahydrofuran, etc., hydrocarbon solvents such as toluene, benzene, hexane, etc., and polar solvents such as dimethylformamide, dimethyl sulfoxide, etc. or without using a solvent, in the presence or absence of a base catalyst at a temperature between 0° C. and the temperature at which the reaction mixture will reflux.

<Process 3>

It is also possible to obtain the compound represented by Formula (VI) or its salt from the compound represented by Formula (V) according to Process 3 of Manufacturing Method 1.

<Process 4>

It is also possible to obtain the compound represented by Formula (I) or its salt from the compound represented by Formula (VI) and the compound represented by Formula (VII) according to Process 4 of Manufacturing Method 1.

<Manufacturing Method 3>

It is possible to prepare the compound represented by Formula (I) or its salt, from a compound represented by Formula (XV) and a compound represented by Formula (XVI) or a compound represented by Formula (XVII) by employing appropriate processes cited in Reaction Scheme 3.

It is also possible to obtain the compound represented by Formula (I) or its salt according to Processes 2, 3 and 4 described below.

<Process 2>

It is also possible to obtain the compound represented by Formula (XVIII) from the compound represented by Formula (XV) and the compound represented by Formula (XVII) according to Process 4 of Manufacturing Method 1.

<Process 3>

It is also possible to obtain the compound represented by Formula (XIX) from the compound represented by Formula (XVIII) according to Process 3 of Manufacturing Method 1.

<Process 4>

It is also possible to obtain a compound represented by Formula (I) or its salt from a compound represented by Formula (XIX) or the compound represented by Formula (VII) according to Process 4 of Manufacturing Method 1.

The compounds prepared as above by the aforementioned processes may be converted to another during process, according to the methods described below.

When the compound wherein A or A' represents —NH—, it is possible to convert the compound to a compound wherein A or A' represents —NR$^3$— (wherein R$^3$ represents lower alkyl group) by using halogenated lower alkyl, meth-

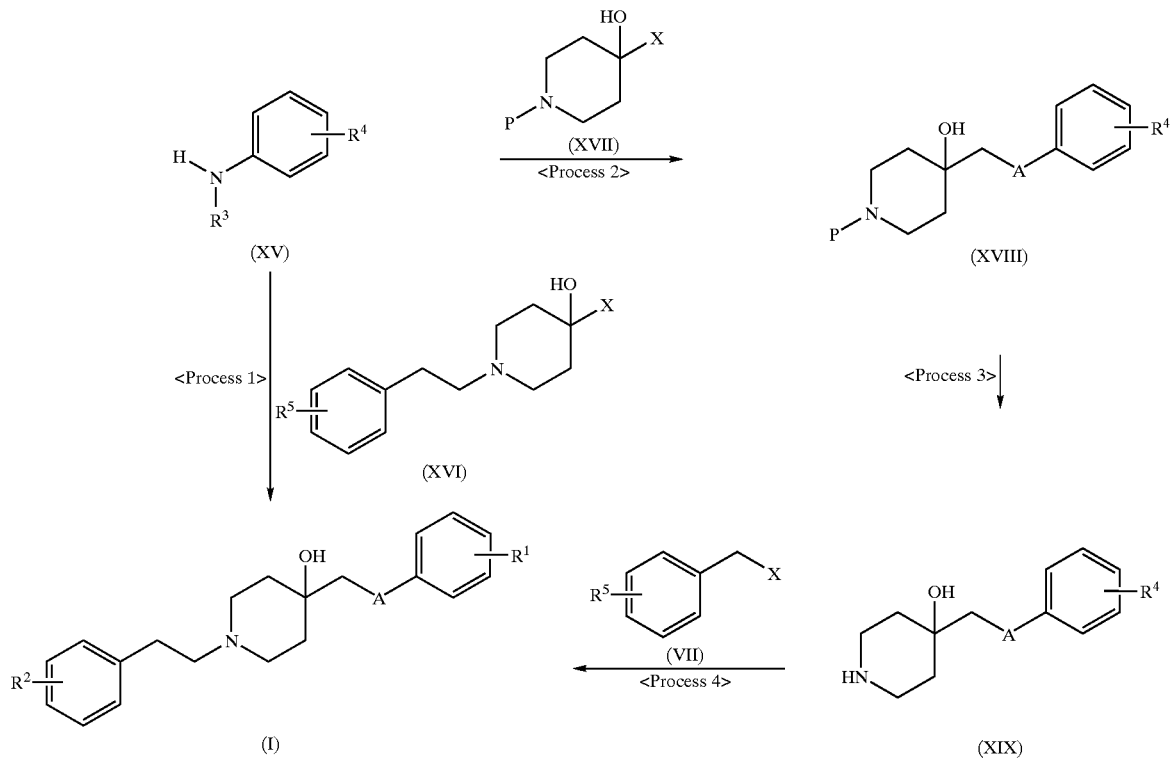

REACTION SCHEME 3

<Process 1>

It is possible to obtain the compound represented by Formula (I) or its salt from the compound represented by Formula (XV) and the compound represented by Formula (XVI) by reacting these compounds according to Process 4 of Manufacturing Method 1, followed by converting, as needed, R$^4$, R$^5$ and R$^6$ to R$^1$, R$^2$ and R$^3$, respectively.

anesulfonyloxy lower alkyl, arylsulfonyloxy lower alkyl, lower alkyl aldehyde, lower alkyl carboxylic acid according to Process 4 of Manufacturing Method 1. Also it is possible to convert to —N(CH$_3$)— by allowing the compound to react with a reducing agent such as sodium borohydride in a solvent not interfering with the reaction, for example, ether solvents such as tetrahydrofuran, etc. or without using a solvent, in the presence of sulfuric acid, by using formalin.

If the compound has lower alkoxycarbonyl group as a substituent, it is possible to replace the alkoxycarbonyl group with carboxyl group, by a known method, for example, by hydrolyzing the compound in a solvent chosen from alcoholic solvents such as methanol, ethanol, etc., in the presence of alkaline aqueous solution of lithium hydroxide, sodium hydroxide or the like at a temperature between room temperature and the temperature at which a reaction mixture will reflux, or by reacting with lithium alkylthiolate in a solvent not interfering the reaction, for example, polar solvents such as dimethylformamide (DMF) or hexamethylphospholamide (HMPA), or reacting with potassium tert-butoxide, potassium trimethylsilanolate, etc. in a solvent not interfering with the reaction, for example, ether solvents such as tetrahydrofuran, etc. or alcoholic solvents such as tert-butanol, etc. Further, it is possible to replace the resulting carboxyl group with a carbamoyl group unsubstituted or mono- or di-substituted by lower alkyl groups, by subjecting the compound to the condensing reaction as described in Method C of Process 4 of Manufacturing Method 1 above.

Further, if the compound prepared as above has formyl group as a substituent on its aromatic ring, it is possible to convert the formyl group to hydroxymethyl group, by a known method, for example, by reacting the compound in a solvent such as alcoholic solvent such as methanol, ethanol, etc. by using a reducing agent such as sodium borohydride, sodium triacetoxylborohydride, sodium cyanoborohydride, etc.

If the compound has cyano group as a substituent on its aromatic ring, it is possible to convert the cyano group to carbamoyl group in the presence of an acid such as hydrochloric acid or sulfuric acid, etc. or a base such as sodium hydroxide, by hydrolysis and so forth.

Further, if the compound prepared as above has halogen atom, or preferably bromine atom as a substituent on its aromatic ring, it is possible to convert the bromine atom to cyano group, by a known method, for example, by placing the compound in a solvent not interfering with the reaction, for example, chosen from polar aprotic solvents such as dimethylformamide, dimethyl sulfoxide, dimethylimidazolidone, etc., by using copper (I) cyanide, potassium cyanide, etc., at a temperature between room temperature and the temperature at which the reaction mixture will reflux. This reaction may proceed in the presence of a catalyst chosen from transition metal complexes comprising palladium complexes, for example, palladium acetate, and nickel complexes, for example, tetrakistriphenylphosphine nickel, etc.

If the compounds prepared as above have, as a substituent, a reactive group such as a hydroxyl group, amino group, carboxyl group, etc., it is possible to protect the group with a protective group appropriately chosen at one process, and then to remove the protective group at another as needed. Introduction and removal of such a protective group may be achieved by any method appropriately chosen depending on the natures of the group to be protected and protective group, for example, by the methods as described in the aforementioned review, "Protective Groups in Organic Synthesis," 3rd Ed., 1999.

Among the reaction intermediates used in the above manufacturing methods, it is possible to prepare the compound represented by Formula (III) by a known method, for example, by allowing the compound represented by Formula (VII) to react with 4-piperidone or its equivalent according to Process 4 of Manufacturing Method 1. Or, it is possible to obtain the compound represented by Formula (III) by reacting the compound represented by Formula (XI):

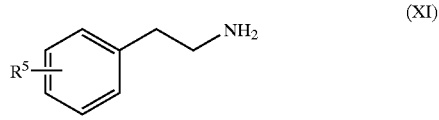

(XI)

by the method as described in Huegi et al., J. Med. Chem. 26:42, 1983, or by Mannich reaction of the compound represented by Formula (XI) with 1,3-acetondicarboxylic derivative, followed by decarboxylation, to obtain the compound represented by Formula (XII):

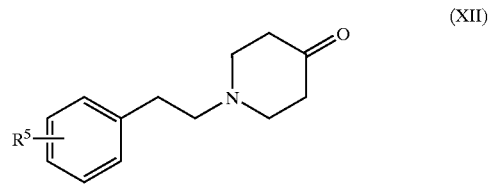

(XII)

and then, reacting the obtained compound represented by Formula (XII) with trimethylsufoxonium iodide, trimethylsifoxonium bromide, etc. in the present of a base, in a solvent not interfering with the reaction, for example, polar solvents such as dimethyl sulfoxide, etc. It is also possible to prepare the compound represented by Formula (III) by reacting the compound represented by Formula (XII) with methylenetriphenylphosphorane in a solvent not interfering the reaction with ether solvents such as ether, dioxane, tetrahyrofuran, etc., polar solvents such as dimethylformamide, dimethylsulfoxide, etc. to convert carbonyl group to methylene group, followed by reacting the methylene group with m-chloroperbenzoic acid in a solvent not interfering the reaction such as halogenated solvents such as methylene chloride, chloroform, etc. to be converted to epoxide, and by selectively reducing only N-oxide when N-oxide is produced.

It is possible to produce the compound represented by Formula (IV) by reacting a compound of the following Formula (XIII):

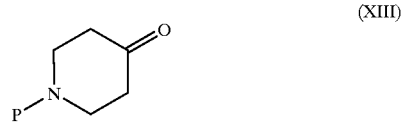

(XIII)

(wherein P has the same meaning as defined above) which is a commercially available compound or can be easily produced by known method, in the present of a base with trimethyl sulfoxonium iodide or trimethyl sulfoxonium bromide, in a solvent not interfering with the reaction, for example, polar solvents such as dimethyl sulfoxide, etc. It is also possible to prepare the compound represented by Formula (IV) by reacting the compound represented by Formula (XIII) with methylenetriphenylphospholan in a solvent not interfering the reaction with ether solvents such as ether, dioxane, tetrahyrofuran, etc., polar solvents such as dimethylformamide, dimethylsulfoxide, etc. to convert carbonyl group to methylene group, followed by reacting the methylene group with m-chloroperbenzoic acid in a solvent not interfering the reaction such as halogenated hydrocarbon solvents such as methylene chloride, chloroform, etc. to be converted to epoxide, and by selectively reducing only N-oxide when N-oxide is produced.

It is possible to produce the compound represented by Formula (IX) or the compound represented by Formula (X), when, for example, Z represents hydroxyl group, by hydrolyzing the compound represented by Formula (III) or the compound represented by Formula (IV) in a solvent not interfering with the reaction, for example, chosen from the group of ether solvents such as dioxane, tetrahydrofuran, etc. and polar solvents such as dimethylformamide, dimethylsulfoxide, etc. by using a base such as sodium hydroxide, potassium hydroxide, etc. When Z represents amino group unprotected or protected by lower alkyl in the compound represented by Formula (IX) or the compound represented by Formula (X), it is possible to produce each compound by reacting the compound represented by Formula (III) or the compound represented by Formula (IV) with ammonia or lower alkylamine in the presence or absence of a base in a solvent not interfering with the reaction, for example, chosed from the group of ether solvents such as dioxane, teterahydrofuran, etc. and polar solvents such as dimethylformamide, dimethyl sulfoxide, etc. In a case of the obtained compound wherein Z represents amino group, it is possible to further produce the compound represented by Formula (IX) or the compound represented by Formula (X) wherein Z represents amino group substituted by lower alkanoyl group or amino group substituted by lower alkyl group, according to the method described in Method C of Process 4 of Manufacturing Method 1.

EXPERIMENTAL EXAMPLES

The present invention will be illustrated below with reference to Experimental Examples, but it should be understood that the present invention is not limited in any way to these examples.

Experimental Example 1

[Inhibitory Effect on the Formalin-induced Nociceptive Response in Rats]

The experiment was undertaken by the method disclosed by Doak et al., Eur. J. Pharmacol. 281:311, 1995. Specifically, 50 μL of 0.5% formalin solution was subcutaneously injected into the left foot pad of the rat, and then each behavior of the rat consisting of the licking or biting of the pad immediately following the injection was checked with a stopwatch for its duration, and its cumulative duration was recorded at five minute intervals. The nociceptive response observed in 10 minutes after the injection was termed a first-phase response while the response observed between 10 minutes and 45 minutes after the injection was termed a second-phase response. The test compound was orally applied to the rat 30 minutes before the subcutaneous injection of formalin. Then, the inhibitory effect of the test compound on the nociceptive response induced by the formalin injection was calculated according to the following formula and 30% inhibition dose ($ED_{30}$ value) was determined by the probit method. The results thus obtained are shown in Table 1. To mention, for illustration, $ED_{30}$ value of carbamazepine was 27 mg/kg.

Percent inhibition (%)=[(PRcontrol−PRtest)/PRcontrol]×100 wherein PRtest is the response time (sec) of the test group which received formalin and the test compound, while PRcontol is the response time of the control group which received formalin and vehicle.

TABLE 1

Inhibitory effects of test compounds on the formalin-induced nociceptive response in rats

| Test Compound | $ED_{30}$ value (mg/kg) |
|---|---|
| Example 11 | 0.047 |
| Example 12 | 2.0 |
| Example 29 | 1.2 |

As is obvious from above result, the compounds of the present invention inhibited the formalin-induced nociceptive response by oral administration with low dose. At the same time, there was no notable abnormalities in general conditions. Thus, the compounds of the present invention were shown to have less toxicity.

Experimental Example 2

[Efficacy in the Rat Model Made by Loosely Constricting the Sciatic Nerve]

Preparation of the rat pain model based on the constriction of the sciatic nerve was performed by the method introduced by Bennett et al. ("Pain," 33:87, 1988). Specifically, the rat was anesthetized with i.p. injection of pentobarbital sodium at 40 mg/kg; the overlying skin was cut open; and the left biceps femoris muscle was bluntly separated. The sciatic nerve was isolated from surrounding tissues; it was gently constricted at four sites about 1 mm apart from each other by the use of surgical gut sutures (4-0 or 3-0 chromic gut); the operated part was closed; and the rat was returned to its cage for further feeding. For the rat belonging to the sham-surgery group, the same operation was performed except that the sciatic nerve was left untouched. Two weeks after the surgery, the response threshold to a mechanical stimulus consisting of touch with von Frey filaments was determined. The test proceeded as follows: the test compound was orally applied to the rat having the sciatic nerve constricted; one hour later, von Frey hairs were applied against the foot pad (spots ranging from heel to the mid-point of foot) one after another in an ascending order of their stiffness; if the rat raises its foot when a certain von Frey hair was applied, the stimulus intensity of that hair was taken as the response threshold (maximum stimulus intensity being 28.84 g). The results are shown in Table 2.

TABLE 2

Efficacy in the rat model made by loosely constricting the sciatic nerve

| | | | Mean threshold (g) | |
|---|---|---|---|---|
| Operation | Test Compound | Dose (mg/kg) | Injured foot (left) | Normal foot (right) |
| A. Efficacy of Example 12 | | | | |
| Sham-operation | — | — | 16.85 | 18.56 |
| Constriction press | — | — | 6.94 | 16.43 |
| Constriction press | Example 12 | 1 | 7.96 | 14.29 |
| Constriction press | Example 12 | 3 | 8.92 | 14.71 |
| Constriction press | Example 12 | 10 | 10.96 | 14.29 |
| B. Efficacy of Example 29 | | | | |
| Constriction press | — | — | 3.50 | 14.80 |
| Constriction press | Example 29 | 1 | 5.22 | 14.12 |
| Constriction press | Example 29 | 3 | 7.09 | 14.49 |
| Constriction press | Example 29 | 10 | 8.61 | 15.49 |

TABLE 2-continued

Efficacy in the rat model made by loosely constricting the sciatic nerve

| Operation | Test Compound | Dose (mg/kg) | Injured foot (left) | Normal foot (right) |
|---|---|---|---|---|
| C. Efficacy of Carbamazepine ||||||
| Constriction press | — | — | 7.41 | 14.65 |
| Constriction press | Carbamazepine | 30 | 9.01 | 20.53 |

In this test, a marked fall in the threshold to a mechanical stimulus was observed only on the injured side, that is, the side at which the sciatic nerve was constricted, suggesting the presence of allodynia.

The compound of the present invention significantly increased the threshold of the injured paw to a mechanical stimulus, while it scarcely affected the response threshold of the normal paw. In contrast, carbamazepine significantly raised the response threshold to a mechanical stimulus not only on the injured side but on the normal side. From above, it was found that the compounds of the present invention selectively control the nociceptive response on the injured part.

Experimental Example 3
[Toxicological Study]

The compounds of Example 8 or Example 12 were orally given to 6 week-old Wistar Hannover female rats at 40 mg/kg/day. There were no abnormalities in general appearance, and all the rats survived during the examination period.

The compound of Example 29 was orally given to 6 week-old Wistar Hannover female rats at 400 mg/Kg/day once daily for 14 days, respectively. All the rats survived until 24 hours after the final administration of the compound, and showed no abnormalities in their general appearances, body weight gains and food consumptions. No abnormal findings were observed in the examinations of hematology, biochemistry, organ weight, and histopathology.

The compound Example 12 or Example 29 were orally given to 3 year-old rhesus male monkeys at 20 mg/Kg/day and 40 mg/Kg/day, respectively, once daily for 14 days. All the monkeys survived until 24 hours after the final administration of the compounds, and showed no abnormalities in their general appearances, body weight gains and food consumptions. No abnormal findings were observed in the examination of hematology, biochemistry, organ weight, and histopathology.

In Holter ECG test, the compound of Example 12 or Example 29 were orally given to 4 year-old rhesus male monkey at 80 mg/Kg. There was no effect in electrocardiogram.

Experimental Example 4
[Pharmacokinetics]

The compound of Example 12 or Example 29 were studied about time-course profile of plasma concentration after a single oral administration to 3 or 4 year-old male rhesus monkey. Both compounds showed very good bioavailability and maximum plasma concentration (Cmax) and area under the plasma concentration-time curve (AUC) increased almostly in proportion to the doses and had property to keep linearity. The both compounds exhibited no serious inhibitory effect on human-drug metabolizing enzymes. Therefore, it can be considered to cause unlikely the drug-drug interaction by the compounds. Moreover, the compounds were metabolically stable in human, monkey, dog and rat liver microsomes and hepatocytes. Therefore, it can be considered that the compounds are unlikely metabolized by first pass effect.

Taking these facts together, it was demonstrated that the compounds of the present invention markedly inhibited the formalin-induced nociceptive response in the rats, when orally applied, moreover, selectively controled the pain on the injured side from the neuropathic pain model rats in which the sciatic nerve was constricted. In addition, the compounds showed very low toxicity, since they induce no abnormal response in the toxicological study.

Furthermore, the compounds of the present invention show to have very good pharmacokietic property.

Moreover, no notable change was observed both in the PQ interval and in the QRS width, which suggests the compounds do not have practically any harmful effect on the cardiac function. Any affection to cardiovascular system such as blood pressure, etc. was not recognized.

Hence, since the compounds of the present invention have excellent analgetic effect in the animal pain model, high safety and good pharmacokenetic property, they can be expected as an excellent analgesic, especially as an agent specifically adapted for the treatment of neuropathic pain.

The compounds of the present invention can be used for the treatment of pain accompanying painful diseases such as hyperalgesia, allodynia, spontaneous painful sensation, for example, for the treatment and prevention of pain accompanying central neuropathy (for example, neuropathy resulting from spinal cord injury), peripheral neuropathy (for example, reflex sympathetic dystrophy (RSD)), herpes zoster infection during its acute phase, postherpetic neuralgia (PHN), diabetic neuropathy, trigeminal neuralgia, postoperative neuralgia, cancer pain, low back pain-related neuropathy, pain state subsequent to spinal cord injury, thalamic pain, limb pain, causalgia, reflex sympathetic nerve atrophy, chronic headache, toothache, periarthritis scaupulohumeralis, osteoarthritis, arthritis, rheumatism, etc., but its effective use is not limited to the above. Or, the inhibitor may be used for preventing or retarding the aggravation of symptoms accompanying those chronic diseases which otherwise may appear in the course of time.

The compounds of the present invention can also be useful to pain diseases which show symptoms such as hyperalgesia (phenomenon that excess reaction is generated against harmful stimulus), allodynia (state that pain is felt by even soft touch), spontaneous pain (state that pain is caused even when no action is taken).

The compounds of the present invention will be effective not only for the treatment of pain diseases, etc., but also for the treatment of convulsion, epilepsy, dementia (cerebrovascular and dementia senilis), cerebral infarction during its acute phase, cerebral hemorrhage, transient cerebral ischemia, subarachnoidal hemorrhage, head trauma, after-effects subsequent to brain surgery, cerebral vascular disorders subsequent to cerebral arterial sclerosis, diseases accompanied by itching, irritable bowel syndrome (IBS), etc., but their use should not be limited to those diseases.

The medicinal preparation of this invention will be used as a medicinal component.

The medicinal component of the present invention may contain at least one of the compounds represented by Formula (I) of the present invention, and may be prepared into a medicine in combination with pharmaceutically acceptable additives. Specifically, the preferred additive includes excipients (for example, lactose, sucrose, mannite, crystalline cellulose, silica, corn starch, potato starch), binders (for example, celluoses (hydroxypropylcellulose (HPC), hydroxypropylmethylcellulose (HPMC)), crystalline cellulose, sugars (lactose, mannitol, sucrose, sorbitol, erythritol, xylitol), starches (corn starch, potato starch), α-starch, dextrin, polyvinylpyrrolidone (PVP), macrogol, polyvinyl alcohol (PVA)), lubricants (for example, magnesium stearate, calcium stearate, talc, carboxymethylcellulose), disintegrants (for example, starches (corn starch, potato starch), sodium carboxymethyl starch, carmellose, carmellose calcium, croscarmellose soidum, crospovidone), coating agents (for example, celluoses (hydroxypropylcellulose (HPC), hydroxypropylmethylcellulose (HPMC), aminoalkylmethacrylate copolymer E, methacrylate copolymer LD), plasticizers (for example, triethyl citrate, macrogol), masking agents (for example, titanium oxide), colorants, flavoring agents, antiseptic agents (benzarconium chloride, paraoxybenzoate ester), isotonicities (for example, glycerin, sodium chloride, potassium chloride, mannitol, glucose), pH adjusters (sodium hydroxide, potassium hydroxide, sodium carbonate, hydrochloric acid, sulfuric acid, buffer such as phosphate-buffer), stabilizers (for example, sugar, sugar alcohol, xanthan gum), dispersants, anti-oxidants (for example, ascorbic acid, butylhydroxyanisol (BHA), propyl gallate, dl-α-tocophenol), buffering agents, preservatives (for example, paraben, benzyl alcohol, benzalconium chloride), fragrances (for example, vanillin, 1-mentol, rose oil), solubilizing agents (for example, polyoxyethylene-hydrogenated castor oil, polysorbate 80, polyethyleneglycol, phopholipid cholesterol, triethanolamine), absorption enhancers (for example, sodium glycolate, disodium edetate, sodium caprylate, acylcarnitines, limonene), gelatinizers, suspension enhancers, emulsifiers, etc., and these additives and any other appropriate additives and solvents generally used may be combined as appropriate with the compound of this invention, and the mixture may be prepared into any appropriate dosage forms.

The preferred dosage form includes tablets, capsules, granules, powder, pills, ointments, patch, suppositories, injectables, sublingual troches, liquid, powder or suspension agents, nasally applicable agents, and sustained releasable agents. The agent of the present invention may be applied to the patient orally, subcutaneously, intramuscularly, percutaneously, intravenously, intraarterially, through the tissues surrounding a nerve, extradurally, intrathecally, intraventricularly, rectally, nasally, etc. Further, they may be modified in such a way as to allow the patient, whenever he feels pain, to apply the agent to the affected site through an infuser dedicated for the purpose (patient-controlled analgesia (PCA)), through a needleless injector, or through percutaneous administration of medicine with ion photolysis.

The agent of this invention should be applied to the adult at 0.005 mg to 3.0 g/day, preferably 0.05 mg to 2.5 g/day, more preferably 0.1 mg to 1.5 g/day but the dose may be changed as appropriate depending on the severity of the symptom, or on the administration route.

A total dose for a day may be applied at once, or it may be divided into 2 to 6 fractions, and each divided fraction may be applied one after another orally or parenterally, or the dose may be applied dropwise or continuously through a tube inserted into a vein.

EXAMPLES

Next, this invention will be described below more in detail by means of Examples, but it should be understood that this invention is not limited in any way to those examples.

The nuclear magnetic resonance (NMR) spectra were obtained with JEOL JNM-EX270 FT-NMR (data obtained with this machine were marked with *, JEOL Ltd.) or JEOL JNM-LA300 FT-NMR (JEOL Ltd.). The infrared (IR) spectra were obtained with Horiba FT-720 (HORIBA Ltd.). The melting points were measured with Mettler FP900 thermo system (METTLER TOLEDO).

Example 1

Synthesis of 1-[2-(4-cyanophenyl)ethyl]-4-(4-hydroxyphenoxymethyl)piperidin-4-ol <Step 1> Synthesis of 4-cyanophenylacetaldehyde Methoxymethyltriphenylphosphonium chloride (392 g) was suspended in anhydrous tetrahydrofuran (1.3 L), and was added dropwise an anhydrous tetrahydrofuran solution (1.3 L) of potassium tert-butoxide (128 g) under nitrogen atmosphere at −20° C. to −15° C. The mixture was stirred at the same temperature for ten minutes and then at 0° C. for eighty minutes. A solution of 4-cyanobenzaldehyde (100 g) in anhydrous tetrahydrofuran (600 mL) was added dropwise to the mixture at −20° C. to −15° C. and stirred at the same temperature for ten minutes, and the reaction mixture was warmed to room temperature over ninety minutes. After water (1 L) was added to the reaction mixture and the mixture was stirred, salt and ether were added thereto until the mixture was separated. The organic layer was washed with brine, and dried over anhydrous sodium sulfate. The solvent was removed under reduced pressure and hexane:ether (1:1, 1 L) was added to the residue obtained to remove insoluble matter by filtration and the filtrate was concentrated under reduced pressure. The obtained oil was purified by silica gel column chromatography (Chromatorex NH™)(eluent; hexane:ethyl acetate=49:1 to 4:1) to give an oil (118 g).

2N hydrochloric acid (230 mL) was added to a solution of acetone (460 mL) in the oil (115 g) and heated under reflux for eighty minutes under nitrogen atmosphere. After allowing to cool, ether and salt were added to the reaction mixture to be separated, and further the aqueous layer was extracted with ether. The organic layer was combined and washed with brine (until pH of the aqueous layer became about 4) and then, was dried over anhydrous sodium sulfate. The solvent was removed under reduced pressure to obtain the titled compound (105 g) as an oil.

<Step 2> Synthesis of 1-[2-(4-cyanophenyl)ethyl]piperidin-4-one

Sodium triacetoxyborohydride (41.4 g) was added to a solution of the compound (13.2 g) obtained in the Step 1 and 4-piperidone hydrochlroide monohydrate (10.0 g) in a methanol (500 mL) under cooling with ice-water over two and half hours, and stirred at the same temperature for one hour. The reaction mixture was concentrated under reduced pressure, and 1N hydrochloric acid (220 mL) and dichiromethane were added to the residue to be separated, and then, the aqueous layer was washed with ethyl acetate. After adjusting pH of the aqueous layer to above 9 with potassium carbonate, the layer was extracted with ethyl acetate. The organic layer was dried over anhydrous sodium sulfate, and the solvent was removed under reduced pressure. The residue was crystallized from 2-propanol and collected by filtration to obtain the titled compound (9.07 g) as crystals.

<Step 3> Synthesis of 1-[2-(4-cyanophenyl)ethyl]piperidin-4-spiro-2'-oxirane

60% sodium hydride (1.89 g) was added to anhydrous dimethylsulfoxide (42 mL) and the mixture was stirred at room temperature for ten minutes under nitrogen atmosphere. After gradually adding trimethylsulfoxonium iodide (10.4 g) to the mixture at 10 to 19° C., the mixture was stirred at 8 to 10° C. for thirty minutes and at room temperature for sixty minutes. An anhydrous dimethylsulfoxide solution (42 mL) of the compound (9.00 g) obtained in Step 2 was added dropwise to the mixture. After stirring the resulting mixture at room temperature for one and half hours, the reaction mixture was poured into an ice water (250 mL) gradually with stirring. The mixture was extracted with ethyl acetate, and the organic layer was combined and washed with water and brine successively. The organic layer was dried over anhydrous sodium sulfate, the solvent was removed under reduced pressure. The residue was crystallized from hexane and collected by filtration to obtain the titled compound (8.61 g) as crystals.

<Step 4> Synthesis of 1-[2-(4-cyanophenyl)ethyl]-4-(4-hydroxyphenoxymethyl)piperidin-4-ol 60% sodium hydride (46 mg) was added to an anhydrous dimethylformamide solution (4 mL) of hydroquinone (0.18 g) under cooling with ice-water and the mixture was stirred at room temperature for fourty minutes under nitrogen atmosphere. The compound (0.40 g) obtained in Step 3 was added to the mixture, and the reaction mixture was stirred at 80° C. for four hours under nitrogen atmosphere. Water (40 mL) was added to the mixture under cooling with ice-water and the mixture was extracted with ethyl acetate. The organic layer was washed with water and brine successively, dried over anhydrous sodium sulfate and then, the solvent was removed under reduced pressure. The obtained residue was purified by silica gel column chromatography (eluent; ethyl acetate:methanol=49:1 to 19:1) and the obtained fractions were concentrated and washed with ether-ethyl acetate to obtain the titled compound (52 mg).

Example 2

Synthesis of 1-[2-(4-cyanophenyl)ethyl]-4-(4-hydroxymethylphenoxymethyl)piperidin-4-ol <Step 1> Synthesis of 1-[2-(4-cyanophenyl)ethyl]-4-(4-formylphenoxymethyl)piperidin-4-ol The compound (10.0 g) obtained in Step 3 of Example 1 and 4-hydroxybenzaldehyde (5.04 g) were dissolved in anhydrous dimethylformamide (55 mL), and to the mixture was added potassium carbonate (28.5 g) and 18-crown-6 (1.09 g) at room temperature under nitrogen atmosphere and the mixture was heated at 100° C. for five hours. After allowing to cool, insoluble matter was removed by filtration and washed with ethyl acetate (300 mL). The filtrate was cooled with ice-water and water (150 mL) was added to the mixture to be separated. The aqueous layer was extracted with ethyl acetate. The organic layer was combined, washed with water and brine successively, and dried over anhydrous sodium sulfate, followed by removal of the solvent under reduced pressure. The obtained residue was crystallized from ether and collected by filtration to obtain the titled compound (12.7 g) as crystals.

<Step 2>Synthesis of 1-[2-(4-cyanophenyl)ethyl]-4-(4-hydroxymethylphenoxymethyl)piperidin-4-ol The compound (0.20 g) obtained in Step 1 was dissolved in a mixture of ethanol (3 mL) and tetrahydrofuran (2.75 mL) and to this solution was added sodium borohydride (0.016 g) under cooling with ice-water and the mixture was stirred at the same temperature for two hours under nitrogen atmosphere. After adding water (15 mL) and stirring, to the mixture was added salt until it was saturated, and the mixture was extracted with ethyl acetate. The organic layer was washed with brine and dried over anhydrous sodium sulfate, and the solvent was removed under reduced pressure. The obtained residue was purified by silica gel column chromatography (Chromatorex NH™) (eluent; ethyl acetate:methanol=99:1 to 9:1) to obtain the titled compound (0.16 g).

Example 3

Synthesis of methyl 4-{1-[2-(4-cyanophenyl)ethyl]-4-(hydroxypiperidin-4-ylmethoxy}benzoate A mixture of the compound (0.24 g) obtained in Step 1 of Example 1 and methyl 4-hydroxybenzoate (0.15 g) was heated and stirred at 100° C. for three hours under nitrogen atmosphere. After allowing to cool, the solidified residue was purified by silica gel column chromatography (Chromatorex NH™)(eluent; ethyl acetate:hexane=1:9 to 3:17) to obtain the titled compound (0.074 g) as crystals.

Example 4

Synthesis of methyl 4-{1-[2-(4-cyanophenyl)ethyl]-4-hydroxypiperidin-4-ylmethoxy}benzoate <Step 1> Synthesis of 1-benzylpiperidin-4-spiro-2'-oxirane 60% sodium hydride (25.4 g) was added to anhydrous dimethylsulfoxide (400 mL) and the mixture was stirred at room temperature under nitrogen atmosphere. Trimethylsulfoxonium iodide (140 g) was added gradually to the mixture at 20 to 28° C., and the mixture was stirred at room temperature for sixty minutes. An anhydrous dimethylsulfoxide solution (400 mL) of 1-benzyl-4-piperidone (100 g) was added dropwise to the mixture. After stirring the resulting mixture at room temperature for sixty minutes, the reaction mixture was poured into ice-water (2.0 L) gradually with stirring. The mixture was extracted with ethyl acetate, and the organic layer was combined and washed with water (four times) and brine successively. After drying over anhydrous sodium sulfate, the solvent was removed under reduced pressure. The obtained residue was purified by silica gel column chromatography (eluent; ethyl acetate:hexane= 1:9 to 1:1) to obtain the titled compound (86.7 g) as an oil.

<Step 2> Synthesis of 1-benzyl-4-hydroxymethylpiperidin-4-ol

85% potassium hydroxide (40.6 g) was dissolved in water (615 mL) and mixed with dioxane (103 mL). A dioxane solution (103 mL) of the compound (25.0 g) obtained in Step 1 was added dropwise to the mixture at 90° C. over 60 minutes under nitrogen atmosphere and stirred at the same temperature for 20 minutes. With cooling the reaction solution with ice-water, the pH of the solution was adjusted to 9 with concentrated hydrochloric acid, the mixture was saturated with salt, and extracted with ethyl acetate. The organic layer was combined and dried over anhydrous sodium sulfate, and the solvent was removed under reduced pressure. The residue was crystallized from hexane:ether and collected by filtration to obtain the titled compound (24.6 g) as crystals.

<Step 3> Synthesis of 1-benzyl-4-(4-cyanophenoxymethyl) piperidin-4-ol

60% sodium hydride (0.30 g) was added to a solution of the compound (1.66 g) obtained in Step 2 in anhydrous dimethylformamide (8 mL) under cooling with ice-water, and stirred at room temperature for thirty minutes under nitrogen atmosphere. 4-fluorobenzonitrile (0.91 g) was added to the mixture and stirred at room temperature for two days. The resulting mixture was poured into water (30 mL) and extracted with ethyl acetate. The organic layer was washed with brine and dried over anhydrous sodium sulfate, and the solvent was removed under reduced pressure. The obtained residue was purified by silica gel column chromatography (Chromatorex NH™)(eluent; ethyl acetate:hexane=1:1) to obtain the titled compound (2.2 g).

<Step 4> Synthesis of 1-benzyl-4-(4-carboxyphenoxymethyl)piperidin-4-ol

The compound (4.27 g) obtained in Step 3 was dissolved in ethanol (38 mL), and to the solution was added 4N sodium hydroxide (33 mL) and the mixture was heated under reflux for eight hours. The resulting mixture was concentrated under reduced pressure up to about 40 mL, and to the residue was added 12N hydrochloric acid (11 mL) under cooling with ice-water. The precipitated crystals were collected by filtration and dried to obtain the titled compound (3.7 g) as crystals.

<Step 5> Synthesis of 1-benzyl-4-(4-methoxycarbonylphenoxymethyl)piperidin-4-ol

The compound (0.86 g) obtained in Step 4 was dissolved in methanol (10 mL) and to the solution was added a 2M trimethylsilyidiazomethan-hexane solution (1.3 mL). After completion of the reaction, the residue from which the solvent was removed under reduced pressure was purified by silica gel column chromatography (Chromatorex NH™) (eluent; ethyl acetate:hexane=1:19 to 1:9) to obtain the titled compound (0.8 g) as crystals.

<Step 6> Synthesis of 4-(4-methoxycarbonylphenoxymethyl)piperidin-4-ol

10% palladium on carbon (2.5 g) was added to a methanol solution (200 mL) of the compound (25 g) obtained in Step 5 and the mixture was stirred at room temperature overnight under hydrogen atmosphere. The catalyst was removed by filtration with Celite™ and the filtrate was condensed under reduced pressure to obtain the titled compound (18.7 g) as crystals.

<Step 7> Synthesis of methyl 4-{1-[2-(4-cyanophenyl)ethyl]-4-hydroxypiperidin-4-ylmethoxy}benzoate Acetic acid (11.5 mL) was added to a dichloromethane solution (450 mL) of the compound (17.7 g) obtained in Step 6 and the compound (19.4 g) obtained in Step 1 of Example 1 at room temperature and the mixture was stirred at the same temperature for thirty minutes. Sodium triacetoxyborohydride (56.6 g) was added to the mixture under cooling with ice-water and the mixture was stirred at the same temperature for thirty minutes and further stirred at room temperature for five hours. The solvent was removed under reduced pressure and insoluble matter (16.1 g) precipitated by adding water (250 mL) and ethyl acetate (250 mL) was collected by filtration. To the obtained insoluble matter (13.0 g) was added water (50 mL) and saturated aqueous sodium hydrogencarbonate solution (150 mL) and the residue was extracted with ethyl acetate. The organic layer was washed with brine and dried over anhydrous sodium sulfate, and the solvent was removed under reduced pressure. The obtained residue was crystallized from ether-hexane to obtain the titled compound (10.3 g) as crystals. The physical data of the obtained compound accord with those of the compound of Example 3.

Example 5

Synthesis of 4-(4-carbamoylphenoxymethyl)-1-[2-(4-cyanophenyl)ethyl]-piperidin-4-ol <Step 1> Synthesis of 4-(4-carbamoylphenoxymethyl)piperidin-4-ol 4N sodium hydroxide (6.8 mL) was added to an ethanol solution (30 mL) of the compound (2.2 g) obtained in Step 3 of Example 4 and the mixture was heated under reflux for four and half hours. The solvent was removed under reduced pressure and to the residue was added water (30 mL), and the precipitate was collected by filtration.

The precipitate was dissolved in methanol (50 mL) and to the solution was added 10% palladium on carbon (0.2 g), and the mixture was stirred at room temperature for two days under hydrogen atmosphere. The catalyst was removed by filtration with Celite™ and the filtrate was concentrated under reduced pressure to obtain the titled compound (0.93 g) as crystals.

<Step 2> Synthesis of 4-(4-carbamoylphenoxymethyl)-1-[2-(4-cyanophenyl)ethyl]-piperidin-4-ol The titled compound (0.5 g) was obtained by the same manner in Step 7 of Example 4 by using the compound (0.93 g) obtained in Step 1 and the compound (0.58 g) obtained in Step 1 of Example 1.

Example 6

Synthesis of 1-[2-(4-cyanophenyl)ethyl)-4-(4-nitrophenoxymethyl)piperidin-4-ol

<Step 1> Synthesis of 1-benzyl-4-(4-nitrophenoxymethyl)piperidin-4-ol

The titled compound (1.6 g) was obtained by the same manner in Step 3 of Example 4 by using the compound (1.1 g) obtained in Step 2 of Example 4 and 4-fluoronitrobenzene (0.72 g).

<Step 2> Synthesis of 4-(4-nitrophenoxymethyl)piperidin-4-ol 1-chloroethyl chloroformate (0.40 g) was added to a dichloroethane solution (5 mL) of the compound (0.47 g) obtained in Step 1 and the mixture was heated under reflux for four and half hours. After the solvent was removed under reduced pressure, to the mixture was added methanol (10 mL), and the mixture was heated under reflux for two hours. The obtained residue by removal of the solvent under reduced pressure was washed with ethyl acetate, the pH of the residue was adjusted to 8 with saturated aqueous sodium hydrogencarbonate solution, and extracted with ethyl acetate. The residue obtained was purified by silica gel column chromatography (Chromatorex NH™) (eluent; ethyl acetate:methanol=10:1) to obtain the titled compound (0.10 g).

<Step 3> Synthesis of 1-[2-(4-cyanophenyl)ethyl]-4-(4-nitrophenoxymethyl)piperidin-4-ol The titled compound (0.054 g) was obtained by the same manner in Step 7 of Example 4 by using the compound (0.090 g) obtained in Step 2 and the compound (0.10 g) obtained in Step 1 of Example 1.

Example 7

Synthesis of 1-[2-(4-cyanophenyl)ethyl]-4-(4-hydroxyphenoxymethyl)piperidin-4-ol hydrochloride 10% hydrochloric acid-methanol (0.2 mL) was added to a methanol solution (2 mL) of the compound (50 mg) obtained in Step 4 of Example 1. After the solvent was removed under reduced pressure, the residue obtained was crystallized from ether and collected by filtration to obtain the titled compound (48 mg) as crystals.

The following hydrochlorides were synthesized in the same manner as in Example 7.

Example 8

Synthesis of 1-[2-(4-cyanophenyl)ethyl]-4-(4-hydroxymethylphenoxymethyl)piperidin-4-ol hydrochloride

Example 9

Synthesis of methyl 4-{1-[2-(4-cyanophenyl)ethyl]-4-hydroxypiperidin-4-ylmethoxy}benzoate hydrochloride

Example 10

Synthesis of 4-(4-carbamoylphenoxymethyl)-1-[2-(4-cyanophenyl)ethyl]-piperidin-4-ol hydrochloride

Example 11

Synthesis of 1-[2-(4-cyanophenyl)ethyl]-4-(4-nitrophenoxymethyl)piperidin-4-ol hydrochloride

Example 12

Synthesis of 4-{1-[2-(4-cyanophenyl)ethyl]-4-hydroxypiperidin-4-ylmethoxy}benzoic acid hydrochloride 2N sodium hydroxide (0.25 mL) was added to a methanol solution (10 mL) of the compound (0.20 g) obtained in Example 3 and heated under reflux for five hours. The solvent was removed under reduced pressure and the residue was dissolved in a small amount of water, and the obtained aqueous layer was washed with ethyl acetate. The remaining aqueous layer was adjusted to pH 3 by diluted hydrochloric acid and the precipitate was collected by filtration to obtain the titled compound (0.069 g) as crystals.

Example 13

Synthesis of 4-{1-[2-(4-cyanophenyl)ethyl]-4-hydroxypiperidin-4-ylmethoxy}benzoic acid N-octanethiol (2.04 g) was dissolved in anhydrous tetrahydrofuran (10 mL) and anhydrous hexamethyl phosphoric triamide (HMPA) (5 mL), and to this solution was added dropwise 1.59 M n-butyllithium-hexane solution (8.74 mL, 13.9 mmol) under nitrogen atmosphere and under cooling with ice-water. After the mixture was stirred at the same temperature for fifteen minutes, a solution of the compound (2.50 g) of Example 3 in anhydrous tetrahydrofuran (10 mL) and anhydrous MHPA (5 mL) were added dropwise to the mixture for ten minutes. The mixture was stirred at the same temperature for thirty minutes and then stirred at room temperature for seventeen hours. After completion of the reaction, to the reaction solution was added ice-water (20 mL) under cooling with ice-water and the residue was washed with ethyl acetate (25 mL×2). With stirring under cooling with ice-water, the pH of the aqueous layer was adjusted to 5.6 by adding 3M hydrochloric acid gradually. The precipitated crystals were collected by filtration and washed with water and ethanol successively. The precipitated crystals were suspended in methanol (50 mL) and water (10 mL) and heated under reflux for thirty minutes. After allowing to cool, crystal was collected by filtration and washed with methanol. The crystals were dried. under reduced pressure to obtain the titled compound (1.83 g) as crystals.

Example 14

Synthesis of 4-({1-[2-(4-cyanophenyl)ethyl]-4-hydroxypiperidin-4-ylmethyl}methylamino)benzoic acid Scandium trifluoromethanesulfonate (609 mg) was added to a mixture of the compound (500 mg) obtained in Step 3 of Example 1, 4-methylaminobenzoic acid (343 mg) and anhydrous acetonitrile (10 mL) under cooling with ice-water, and the mixture was stirred at room temperature for sixty eight hours under nitrogen atmosphere. Water (50 mL) and acetonitrile (10 mL) were added to the resulting mixture and the pH of the mixture was adjusted to above 9 with sodium hydrogen carbonate, insoluble matter was removed by filtration and the filtrate was concentrated under reduced pressure. Water in the residue was removed by azeotrope with ethanol, soluble components in the residue were dissolved in ethanol and the insoluble matter was removed by filtration. The filtrate was concentrated under reduced pressure and then, the residue was dissolved in water (50 mL) and the pH of the solution was adjusted to 7 by diluted hydrochloric acid. Precipitate was collected by filtration and washed with water and ethyl acetate successively under stirring. The precipitate was collected by filtration and dried to obtain the titled compound (524 mg) as powder.

Example 15

Synthesis of 3-({1-[2-(4-cyanophenyl)ethyl]-4-hydroxypiperidin-4-ylmethyl}methylamino)benzoic acid <Step 1> Synthesis of methyl 3-formylaminobenzoate 1-ethyl-3-(3-dimethylaminopropyl)carbodiimide hydrochloride (2.47 g) was added to a mixture of methyl 3-aminobenzoate (1.50 g), formic acid (748 μL) and dichloromethane (15 mL) under cooling with ice-water, and the mixture was stirred at the same temperature for ten minutes under nitrogen atmosphere and stirred at room temperature for fourteen hours. The reaction mixture was poured into ice-water (30 mL) to be separated and the aqueous layer was extracted with dichloromethane. The organic layer was washed with water and an aqueous sodium hydrogencarbonate solution successively, and dried over anhydrous sodium sulfate. After the solvent was removed under reduced pressure, the residue obtained was washed with ether and dried to obtain the titled compound (1.61 g) as crystals.

<Step 2> Synthesis of 3-mehtylaminobenzoic acid

Tetrahydrofuran solution of borane-tetrahydrofuran complex (1M; 16.7 mL) was gradually added to an anhydrous tetrahydrofuran solution (10 mL) of the compound (1.00 g) obtained in Step 1 under cooling with ice-water, and stirred at the same temperature for thirty minutes and then at room temperature fourteen hours under nitrogen atmosphere. After dropwise adding methanol (5 mL) under cooling with ice-water, the mixture was adjusted to below pH 1 by adding a 10% hydrogen chloride-methanol solution (10 mL), followed by heating under reflux for two hours. The solvent was removed under reduced pressure and to the residue obtained was added an aqueous sodium hydrogencarbonate solution and extracted with ethyl acetate. The organic layer was washed with brine, dried over anhydrous sodium sulfate, and the solvent was removed under reduced pressure to obtain an oil (1.05 g).

Sodium hydroxide (160 mg) was added to an ethanol solution (10 mL) of the obtained oil (500 mg) and heated under reflux for nine hours. The solvent was removed under reduced pressure, the residue was dissolved in water (20 mL) and the solution was washed with ether. The aqueous layer was adjusted to pH 5 to 6 with diluted hydrochloric acid and extracted with ethyl acetate. The organic layer was washed with brine and dried over anhydrous sodium sulfate. The solvent was removed under reduced pressure to obtain the titled compound (338 mg) as crystals.

<Step 3> Synthesis of 3-({1-[2-(4-cyanophenyl)ethyl)-4-hydroxypiperidin-4-ylmethyl}methylamino)benzoic acid The titled compound (162 mg) was obtained as powder by the same manner in Example 14 by using the compound (200 mg) obtained in Step 3 of Example 1 and the compound (137 mg) obtained in Step 2.

Example 16

Synthesis of 4-[2-(4-hydroxy-4-{[methyl(4-nitrophenyl)amino]methyl}piperidin-1-yl)ethyl]benzonitrile The titled compound (73 mg) was obtained as powder by the same manner in Example 14 by using the compound (485 mg) obtained in Step 3 of Example 1 and N-methyl-4-nitroaniline (335 mg).

Example 17

Synthesis of 4-{2-[4-hydroxy-4-({methyl[4-(1H-tetrazol-5-yl)phenyl]-amino}methyl)piperidin-1-yl] ethyl}benzonitrile <Step 1> Synthesis of 4-methylaminobenzonitrile A 40% methylamine methanol solution (7.5 mL) was added to a methanol (2.5 mL) solution of 4-fluorobenzonitrile (2.00 g) and the mixture was heated under reflux for fifteen hours under nitrogen atmosphere. After the solvent was removed under reduced pressure, to the residue obtained was added water (15 mL) and the mixture was extracted with ethyl acetate. The organic layer was washed with water and brine successively, and dried over anhydrous sodium sulfate. The oil obtained by removal of the solvent under reduced pressure was purified by silica gel column chromatography (eluent; hexane:ethyl acetate= 2:1) to obtain the titled compound (0.48 g) as crystals.

<Step 2> Synthesis of N-methyl-4-(1H-tetrazol-5-yl)aniline

A mixture of the compound (450 mg) obtained in Step 1, 90% sodium azide (664 mg), triethylammonium chloride (703 mg) and anhydrous 1-methyl-2-pirrolidone (12 mL) was stirred at 140 to 160° C. for ten hours under nitrogen atmosphere. The reaction mixture was poured into ice-water, and the residue was adjusted to pH 3 with diluted hydrochloric acid and extracted with ethyl acetate. The organic layer was washed with water and brine successively, and dried over anhydrous sodium sulfate. The solvent was removed under reduced pressure, and the residue was crystallized from tert-butyl methyl ether, collected by filtration and dried to obtain the titled compound (471 mg) as crystals.

<Step 3> Synthesis of 4-{2-[4-hydroxy-4-({methyl[4-(1H-tetrazol-5-yl)phenyl]amino{methyl)piperidin-1-yl] ethyl}benoznitrile The titled compound (85 mg) was obtained as powder by the same manner in Example 14 by using the compound (250 mg) obtained in Step 3 of Example 1 and the compound (199 mg) obtained in Step 2.

Example 18

Synthesis of 4-({1-[2-(4-cyanophenyl)ethyl]-4-hydroxypiperidin-4-ylmethyl}methylamino)benzoic acid Methanol (2 mL) was added to a mixture of the compound (50.0 mg) obtained in Step 3 of Example 1, 4-methylaminobenozic acid (34.3 mg), β-cyclodextrin (58.6 mg), 1N sodium hydroxide (227 µL) and water (2 mL) and the mixture was stirred at room temperature for three days under nitrogen atmosphere. 2-propanol (2 mL) and ether (2 mL) were added to the resulting mixture, and insoluble matter was removed by filtration. After the filtrate was concentrated under reduced pressure, to the residue was added 2-propanol to dissolve soluble component, and insoluble matter was removed by filtration and the filtrate was concentrated. The residue was triturated with ether and the precipitate was collected by filtration. The precipitate was dissolved in water and the solution was adjusted to pH 7 with diluted hydrochloric acid, the precipitate was washed with water, ethyl acetate and ether successively with stirring, collected by filtration and dried to obtain the titled compound (41. 0 mg) as powder. The physical data of the obtained compound accord with those of the compound of Example 14.

Example 19

Synthesis of 2-({1-[2-(4-cyanophenyl)ethyl]-4-hydroxypiperidin-4-ylmethyl}methylamino)benzoic acid The titled compound (211 mg) was obtained as powder by the same manner in Example 18 by using the compound (200 mg) obtained in Step 3 of Example 1 and 2-methylamino benzoic acid (137 mg).

Example 20

Synthesis of methyl 4-({1-[2-(4-cyanophenyl) ethyl]-4-hydroxypiperidin-4-ylmethyl}methylamino) benzoate <Step 1> Synthesis of methyl 4-formylaminobenzoate Formic acid (90.0 mL) was added to a dichloromethane solution (900 mL) of methyl 4-aminobenzoate (90.0 g) and to the mixture was added 1-ethyl-3-(3-dimethylaminopropyl)carbodiimide hydrochloride (114 g) at 5° C. over thirty minutes, and then the mixture was stirred at room temperature for three hours. To the reaction mixture was added saturated aqueous sodium hydrogencarbonate solution (1.2 L) and the pH was adjusted to 10 with 1N sodium hydroxide, and the residue was separated. The aqueous layer was extracted with dichloromethane, and the organic layer was combined and washed with 1N hydrochloric acid, water and brine successively. After the organic layer was dried over anhydrous sodium sulfate, the solvent was removed under reduced pressure, and the residue obtained was washed with ethyl acetate to obtain the titled compound (88.7 g) as crystals.

<Step 2> Synthesis of methyl 4-({1-[2-(4-cyanophenyl) ethyl]-4-hydroxypiperidin-4-ylmethyl}methylamino) benzoate A mixture of the compound (139 g) obtained in Step 3 of Example 1, the compound (113 g) obtained in Step 1, potassium carbonate (120 g) and acetonitrile (570 mL) was heated under reflux for twenty three hours under nitrogen atmosphere. Insoluble matter was removed by filtration and the filtrate was concentrated under reduced pressure to obtain a crude intermediate compound (250 g) as an oil.

Borane-methyl sulfide complex (10M; 148 mL) was added dropwise to anhydrous tetrahydrofuran solution (2.0 L) of the crude intermediate compound (250 g) under cooling with ice-water and the mixture was stirred at the same temperature for thirty minutes under nitrogen atmosphere and at room temperature overnight. After methanol was added gradually to the reaction solution under cooling with ice-water, 10% hydrochloric acid-methanol was added to adjust pH to below 1, followed by stirring at room temperature for thirty minutes and then heating under reflux for two hours. The solvent was removed under reduced pressure and to the residue obtained was added a saturated aqueous sodium hydrogencarbonate solution (900 mL), and the pH was adjusted to 10 with potassium carbonate. The mixture was extracted with dichloromethane, and the organic layer was combined and washed with brine, and then, dried over anhydrous sodium sulfate. After the solvent was removed under reduced pressure, the residue obtained was purified by silica gel column chromatography (Chromatorex NH™) (eluent; hexane:dichloromethane=1:1 to 1:2). The obtained crude product was suspended in ether, washed and collected by filtration to obtain the titled compound (33.3 g) as powder.

Example 21

Synthesis of tert-butyl 4-({1-[2-(4-cyanophenyl) ethyl]-4-hydroxypiperidin-4-ylmethyl}methylamino) benzoate <Step 1> Synthesis of tert-butyl 4-methylaminobenzoate 1-ethyl-3-(3-dimethylaminopropyl)carbodiimide hydrochloride (25.6 g) and 4-dimethylaminopyridine (134 mg) were added to 4-methyl aminobenzoate (20.2 g) and tert-buthanol (100 g) and the mixture was stirred at room temperature for five hours. The residue obtained by removal of the solvent under reduced pressure was extracted with ethyl acetate. The organic layer was washed with water, a saturated aqueous sodiurri hydrogencarbonate solution and brine successively, and dried over anhydrous sodium sulfate. The solvent was removed under reduced pressure to obtain the titled compound (16.0 g) as an oil.

<Step 2> Synthesis of tert-butyl 4-({1-[2-(4-cyanophenyl) ethyl]-4-hydroxypiperidin-4-ylmethyl}methylamino) benzoate A hexane solution of n-butyllithium (1.57M; 2.68 mL) was added dropwise to an anhydrous tetrahydrofuran solution (4.22 mL) of the compound (874 mg) obtained in Step 1 at the internal temperature of below 5° C. and the mixture was stirred under cooling with ice-water for one hour. To the mixture was added dropwise an anhydrous tetrahydrofuran solution (4.22 mL) of the compound (1.02 g) obtained in Step 3 of Example 1 at the internal temperature of below 5° C. over thirty minutes, stirred at the same temperature for one hour and further at room temperature for fifty two hours. To the solution added water (40 mL) under cooling with ice-water and the residue was extracted with ethyl acetate. After the organic layer was washed with brine and dried over anhydrous sodium sulfate, the solvent was removed under reduced pressure. The obtained residue was purified by silica gel column chromatography (Chromatorex NH™)(eluent; hexane:ethyl acetate=7:3 to 1:1) to obtain the titled compound (940 mg) as powder.

Example 22

Synthesis of tert-butyl 4-({1-[2-(4-cyanophenyl) ethyl]-4-hydroxypiperidin-4-ylmethyl}methylamino) benzoate <Step 1> Synthesis of tert-butyl 4-formylaminobenzoate The titled compound (25.8 mg) was obtained as crystals by the same manner in Step 1 of Example 15 by using tert-butyl 4-aminobenzoate (25 g).

<Step 2> Synthesis of tert-butyl 4-({1-[2-(4-cyanophenyl)ethyl]-4-hydroxypiperidin-4-ylmethyl}amino)benzoate A mixture of the compound (0.48 g) obtained in Step 3 of Example 1, the compound (0.44 g) obtained in Step 1, potassium carbonate (0.55 g) and anhydrous dimethylformamide (5 mL) was stirred at 95 to 105° C. for three hours under nitrogen atmosphere. Water (30 mL) was added to the resulting mixture and the residue was extracted with ethyl acetate. The organic layer was washed with brine and dried over anhydrous sodium sulfate. The residue (1.1 g) obtained by removal of the solvent was purified by silica gel column chromatography (Chromatorex NH™)(eluent; hexane:ethyl acetate=1:1 to ethyl acetate) to obtain the titled compound (0.55 g) as crystals.

<Step 3> Synthesis of tert-butyl 4-({1-[2-(4-cyanophenyl) ethyl]-4-hydroxypiperidin-4-ylmethyl}methylamino) benzoate To a mixture of 3M sulfuric acid (1.7 mL) and an aqueous 37% formaldehyde solution (37 mg) was added dropwise a suspension of sodium borohydride (38 mg) and the compound (0.10 g) obtained in Step 2 in tetrahydrofuran (2 mL) under cooling with ice-water, and vigorously stirred at the same temperature for one hour. The resulting mixture was adjusted to pH 7 with saturated aqueous sodium hydrogencarbonate solution and extracted with ethyl acetate. The organic layer was washed with brine and dried over anhydrous sodium sulfate. The residue (0.10 g) obtained by removal of the solvent was purified by silica gel column chromatography (Chromatorex NH™) (eluent; hexane:ethyl acetate=3:1 to 1:1) to obtain the titled compound (60 mg) as crystals. The physical data of the obtained compound accord to those of the compound of Example 21.

Example 23

Synthesis of methyl 4-({1-[2-(4-cyanophenyl) ethyl]-4-hydroxypiperidin-4-ylmethyl}methylamino) benzoate <Step 1> Synthesis of methyl 4-({1-[2-(4-cyanophenyl) ethyl]-4-hydroxypiperidin-4-ylmethyl}amino)benzoate A mixture of the compound (242 mg) obtained in Step 3 of Example 1, methyl 4-aminobenzoate (756 mg), anhydrous lithium perchlorate (106 mg) and anhydrous acetonitrile (1 mL) was heated under reflux for two hours under nitrogen atmosphere. To the mixture was added brine (5 mL) and the residue was extracted with ethyl acetate. The organic layer was washed with brine and dried over anhydrous sodium sulfate. The solid residue obtained by removal of the solvent was washed two times by suspending in tert-butyl methyl ether to obtain the titled compound (144 mg) as powder.

<Step 2> Synthesis of methyl 4-({1-[2-(4-cyanophenyl) ethyl]-4-hydroxypiperidin-4-ylmethyl}methylamino) benzoate The titled compound (20.6 g) was obtained as crystals by the same manner in Step 3 of Example 22 by using the compound (33.7 g) obtained in Step 1. The physical data of the obtained compound accord with those of the compound of Example 20.

Example 24

Synthesis of sodium 4-({1-[2-(4-cyanophenyl) ethyl]-4-hydroxypiperidin-4-ylmethyl}methylamino) benzoate <Step 1> Synthesis of sadium 4-({1-[2-(4-cyanophenyl) ethyl]-4-hydroxypiperidin-4-ylmethyl}methylamino) benzoic acid 90% potassium trimethylsilanolate (787 mg) was added to a anhydrous tetrahydrofuran solution (35 mL) of the compound (1.00 g) obtained in the Example 20 under cooling with ice-water and the mixture was stirred at room temperature overnight under nitrogen atmosphere. The solvent was removed under reduced pressure and to the residue was added ethyl acetate (10 mL) and the mixture was stirred, and insoluble matter was collected by filtration. The obtained insoluble matter was washed repeatedly by the similar manner and dried to obtain insoluble matter (771 mg). 300 mg of the obtained insoluble matter was dissolved in water (2 mL) and then the solution was adjusted to pH 7 with 2N hydrochloric acid. After the precipitate was collected by filtration, washed with water and air-dried, the precipitate was further dried under reduced pressure to obtain the titled compound (126 mg) as powder. The physical data of the obtained compound accord with those of the compound of Example 14.

<Step 2> Synthesis of sodium 4-({1-[2-(4-cyanophenyl)ethyl]-4-hydroxypiperidin-4-ylmethyl}methylamino)benzoate 1N aqueous sodium hydroxide solution (238 μL) was added to a methanol suspension (10 mL) of the compound (93.5 mg) obtained in Step 1 and the mixture was stirred at room temperature for thirty minutes. The solvent was removed under reduced pressure and to the residue obtained was added ethyl acetate (5 mL) to be solidified. Insoluble matter was collected by filtration and dried to obtain the titled compound (76.0 mg) as powder.

Example 25

Synthesis of methyl 4-({1-[2-(3-cyanophenyl)ethyl]-4-hydroxypiperidin-4-ylmethyl}methylamino)benzoate <Step 1> Synthesis of 3-cyanophenylacetoaldehyde The titled compound (6.32 g) was obtained as an oil by the same manner in Step 1 of Example 1 by using 3-cyanobenzaldehyde (6.0 g).

<Step 2> Synthesis of methyl 4-[(1-benzyl-4-hydroxypiperidin-4-ylmethyl}methylamino)benzoate Potassium carbonate (92.0 g) was added to an anhydrous acetonitrile solution (300 mL) of the compound (90.0 g) obtained in Step 1 of Example 4 and the compound (79.3 g) obtained in Step 1 of Example 20 and the mixture was heated under reflux under nitrogen atmosphere. After allowing to cool, the mixture was filtered with Celite and the filtrate was concentrated under reduced pressure to obtain a crude intermediate compound (164 g) as an oil.

Borane-methylsulfide complex (10M; 83.7 mL) was added dropwise to tetrahydrofuran solution (120 mL) of the crude intermediate compound (164 g) under cooling with ice-water and under nitrogen atmosphere over twenty minutes, and then the mixture was stirred at room temperature for three hours. Methanol (400 mL) was added gradually to the reaction solution under cooling with ice-water, and the solution was adjusted pH to below 1 by adding hydrogen chloride-methanol reagent (2.5M/L:400 mL) and heated under reflux for two hours. The solvent was removed under reduced pressure and to the residue was added ethyl acetate (2 L) and saturated aqueous sodium hydrogencarbonate solution (1 L), and the pH of the residue was adjusted to 10 by using aqueous 1N sodium hydroxide solution and the mixture was separated. The aqueous layer was extracted with ethyl acetate and the ethyl acetate layer was combined and washed with water and brine successively, and then dried over anhydrous sodium sulfate. The solvent was removed under reduced pressure and the residue was purified by silica gel column chromatography (eluent; ethyl acetate:methanol=20:1 to 10:1) to obtain crude crystals (125 g). The crude crystals were purified by silica gel column chromatography (Chromatorex NH™)(eluent; hexane:ethyl acetate:tetrahydrofuran=4:4:1) to obtain the titled compound (67.7 9) as crystals.

<Step 3> Synthesis of methyl 4-[(4-hydroxypiperidin-4-ylmethyl)methylamino])benzoate 10% palladium on carbon (3.9 g) was added to methanol (480 mL) and stirred at room temperature for one hour under hydrogen atmosphere. A methanol solution (200 mL) of the compound (67.7 g) synthesized in Step 2 was added to the mixture and the residue was stirred at room temperature for thirty hours under hydrogen atmosphere. The catalyst was separated by filtration with Celite and the filtrate was concentrated under reduced pressure to obtain an oil (58.6 g). To the oil was added ether to be crystallized and the crystals were collected by filtration. The crystals were dried under reduced pressure to obtain the titled compound (51.6 9) as crystals.

<Step 4> Synthesis of methyl 4-({1-[2-(3-cyanophenyl)ethyl]-4-hydroxypiperidin-4-ylmethyl}methylamino)benzoate To dichloromethane (14 mL) were added the compound (557 mg) obtained in Step 3, the compound (581 mg) obtained in Step 1 and acetic acid (0.7 mL), and was added sodium tricacetoxyborohydride (1.70 g) under cooling with ice-water, and then the mixture was stirred at the same temperature for forty five minutes and at room temperature for four hours. Water (10 mL) was gradually added to the mixture under cooling with ice-water and adjusted to pH 9 to 10 with potassium carbonate and then separated, and the aqueous layer was extracted with dichloromethane. The combined dichloromethane layer was washed and dried over anhydrous sodium sulfate. The residue obtained by removal of the solvent under reduced pressure was purified by silica gel column chromatography (eluent; ethyl acetate:methanol=9:1 to 4:1) to obtain the titled compound (210 mg) as an oil.

Example 26

Synthesis of methyl 4-({1-[2-(2-cyanophenyl)ethyl]-4-hydroxypiperidin-4-ylmethyl}methylamino)benzoate <Step 1> Synthesis of 2-cyanophenylacetoaldehyde The titled compound (705 mg) was obtained as an oil by the same manner in Step 1 of Example 1 by using 2-cyanobenzaldehyde (833 mg).

<Step 2> Synthesis of methyl 4-({1-[2-(2-cyanophenyl)ethyl]-4-hydroxypiperidin-4-ylmethyl}methylamino)benzoate The titled compound (672 mg) was obtained as crystals by the same manner in Step 4 of Example 25 by using the compound (500 mg) obtained in Step 3 of Example 25 and the compound (391 mg) obtained in Step 1.

Example 27

Synthesis of 4-({4-hydroxy-1-[2-(4-methanesulfonylphenyl)ethyl]piperidin-4-ylmethyl}methylamino)benzoic acid <Step 1> Synthesis of methyl 4-({4-hydroxy-1-[2-(4-methanesulfonylphenyl)acetyl]piperidin-4-ylmethyl}methylamino)benzoate 1-ethyl-3-(3-dimethylaminopropyl)carbodiimide hydrochloride (0.68 g) was added to a dichloromethane solution (15 mL) of the compound (0.90 g) obtained in Step 3 of Example 25 and 4-methylsulfonylphenylacetic acid (0.76 g) and the mixture was stirred at room temperature for one hour. The reaction mixture was poured into cold water (80 mL) and then separated, and the aqueous layer was extracted with dichloromethane. The organic layer was combined and washed with water and brine successively, and then dried over anhydrous sodium sulfate. After the solvent was removed under reduce pressure, the residue was purified by silica gel column chromatography (eluent; dichloromethane:methanol=8:1) to obtain the titled compound (1.36 g) as crystals.

<Step 2> Synthesis of methyl 4-({4-hydroxy-1-[2-(4-methanesulfonylphenyl)ethyl]piperidin-4-ylmethyl}methylamino)benzoate Borane-methylsulfide complex (10M; 0.86 mL) was added to a mixture of the compound (1.36 g) obtained in Step 1, anhydrous tetrahydrofuran (15 mL) and anhydrous chloroform (85 mL) under cooling with ice-water over five minutes under nitrogen atmosphere, and the mixture was stirred at room temperature for twenty four hours. After methanol (10 mL) was added to the mixture under cooling with ice-water, hydrogen chloride-methanol reagent (2.5 M; 5.0 mL) was added to adjust pH to below 1 and the mixture was heated under reflux for two hours. The solvent was removed under reduced pressure and to the residue was added chloroform (50 mL) and saturated aqueous sodium hydrogencarbonate solution (50 mL). The mixture was adjusted to pH 10 by using aqueous 2N sodium hydroxide solution (5 mL) and then separated, and the aqueous layer was extracted with chloroform. The organic layer was combined and washed with water and brine successively, and dried over anhydrous sodium sulfate. After the solvent was removed under reduced pressure, the residue was purified by silica gel column chromatography (Chromatorex NH™) (eluent; dichlorometane:methanol=20:1). The fractions were concentrated and the residue was washed with ethyl acetate and dried to obtain the titled compound (0.76 g) as crystals.

<Step 3> Synthesis of 4-({4-hydroxy-1-[2-(4-methanesulfonylphenyl)ethyl]piperidin-4-ylmethyl}methylamino)benzoic acid An aqueous 2N sodium hydroxide solution (3.4 mL) was added to methanol (20 mL) solution of the compound (0.78 g) obtained in Step 2 and heated under reflux for three hours. The solvent was removed under reduced pressure and to the residue was added with ether and water to be separated. The aqueous layer was washed with ether and the remaining aqueous layer adjusted to pH 5 to 7 with 3N hydrochloric acid and stirred at 50° C. for thirty minutes. The precipitate was collected by filtration and washed with water and then dried under reduced pressure to obtain the titled compound (0.67 g) as crystals.

Example 28

Synthesis of 4-[(4-hydroxy-1-phenethylpiperidin-4-ylmethyl)methylamino)benzoic acid <Step 1> Synthesis of methyl 4-[(4-hydroxy-1-phenylacetylpiperidin-4-ylmethyl}methylamino)benzoate The titled compound (3.52 g) was obtained as crystals by the same manner in Step 1 of Example 27 by using the compound (3.45 g) obtained in Step 3 of Example 25 and phenylacetic acid (1.86 g).

<Step 2> Synthesis of methyl 4-[(4-hydroxy-1-phenethylpiperidin-4-ylmethyl}methylamino)benzoate The titled compound (3.12 g) was obtained as crystals by the same manner in Step 2 of Example 27 by using the compound (4.52 g) obtained in Step 1.

<Step 3> Synthesis of 4-[(4-hydroxy-1-phenethylpiperidin-4-ylmethyl}methylamino)benzoic acid The titled compound (1.50 g) was obtained as crystals by the same manner in Step 3 of Example 27 by using the compound (1.55 g) obtained in Step 2.

Example 29

Synthesis of 4-({1-[2-(4-cyanophenyl)ethyl]-4-hydroxypiperidin-4-ylmethyl}methylamino)benzoic acid monohydrochloride 2N hydrochloric acid (76 μL) was added to an acetic acid solution (100 μL) of the compound (50.0 mg) obtained in Example 14 to prepare homogenous solution. Water (400 μL) was gradually added under stirring and left at rest at room temperature for thirty minutes. The precipitate was collected by filtration and washed with water, ethyl acetate and ether successively, and dried to obtain the titled compound (48.2 mg) as crystals.

The following compounds were synthesized in the same manner in Example 29.

Example 30

Synthesis of 3-({1-[2-(4-cyanophenyl)ethyl]-4-hydroxypiperidin-4-ylmethyl}methylamino)benzoic acid monohydrochloride Example 31

Synthesis of 2-({1-[2-(4-cyanophenyl)ethyl]-4-hydroxypiperidin-4-ylmethyl}methylamino)benzoic acid monohydrochloride Example 32

Synthesis of 4-({2-[4-hydroxy-4-({methyl[4-(1H-tetrazol-5-yl)phenyl]amino}methyl)piperidin-1-yl]ethyl}benzonitrile monohydrochloride Example 33

Synthesis of 4-[2-(4-hydroxy-4-{[methyl(4-nitrophenyl)amino]methyl}piperidin-1-yl)ethyl]benzonitrile monohydrochloride The compound (80 mg) of Example 16 was dissolved in 2-propanol (2 mL) and methanol (1 mL) and to the solution was added 1M hydrogen chloride-ether (0.3 mL) and then the mixture was stirred. The solvent was removed under reduced pressure, and to the residue was added ether to be powdered, the powder was collected by filtration and dried to obtain the titled compound (73 mg) as powder.

Example 34

Synthesis of 4-({1-[2-(4-cyanophenyl)ethyl]-4-hydroxypiperidin-4-ylmethyl}methylamino)benzoic acid monohydrochloride The compound (100 mg) obtained in Step 2 of Example 21 was dissolved in 6N hydrochloric acid (0.5 mL) at room temperature and stirred at the same temperature for five hours. To the mixture was added water (3 mL) and adjusted to pH 9 to 10 by potassium carbonate, and the aqueous layer was washed with ethyl acetate. Insoluble matter of the aqueous layer was removed by filtration and the filtrate was adjusted to pH 3 with 6N hydrochloric acid. The precipitate was collected by filtration and dried to obtain the titled compound (71 mg) as crystals. The physical data of the obtained compound accord with those of the compound of Example 29.

The following compound was synthesized in the same manner in Example 34.

Example 35

Synthesis of 4-({1-[2-(4-cyanophenyl)ethyl]-4-hydroxypiperidin-4-ylmethyl}amino)benzoic acid monohydrochloride Example 36

Synthesis of 4-({4-hydroxy-1-[2-(4-methanesulfonylphenyl)ethyl]piperidin-4-ylmethyl}methylamino)benzoic acid monohydrochloride The compound (0.65 g) obtained in Step 3 of Example 27 was dissolved in an aqueous 0.4N sodium hydroxide solution (25 mL) and the pH was adjusted to 3 to 4 by using 3N hydrochloric acid at 5° C. and the residue was stirred at the same temperature for thirty minutes. The precipitate was collected by filtration and washed with cold water, and dried under reduced pressure to obtain the titled compound (0.61 g) as crystals.

The following compound was synthesized in the same manner in Example 36.

Example 37

Synthesis of 4-[(4-hydroxy-1-phenethylpiperidin-4-ylmethyl)methyl-amino]benzoic acid monohydrochloride

Example 38

Synthesis of 4-({1-[2-(4-cyanophenl)ethyl]-4-hydroxypiperidin-4-ylmethyl}methylamino)benzoic acid monohydrochloride 90% potassium trimethylsilanolate (14.0 g) was added to anhydrous teterahydrofuran solution (630 mL) of the compound (17.8 g) obtained in Step 2 of Example 20 under cooling with ice-water and the mixture was stirred at the same temperature for thirty minutes and stirred at room temperature overnight. The solvent was removed under reduced pressure and to the residue was added ethyl acetate and stirred, and then insoluble matter was collected by filtration. The obtained insoluble matter was repeated two times with the similar washing operation and dried. The insoluble matter was dissolved in water (500 mL) and the solution was adjusted to pH 3 with 6N hydrochloric acid. The precipitate was collected by filtration, washed with water and dried under reduced pressure to obtain the titled compound (9.02 g) as powder. The physical data of the obtained compound accord with those of the compound of Example 29.

The following compounds were synthesized in the same manner in Example 38.

Example 39

Synthesis of 4-({1-[2-(3-cyanophenyl)ethyl]-4-hydroxypiperidin-4-ylmethyl}methylamino)benzoic acid monohydrochloride

Example 40

Synthesis of 4-({1-[2-(2-cyanophenyl)ethyl]-4-hydroxypiperidin-4-ylmethyl}methylamino)benzoic acid monohydrochloride The physical data of the compounds of Examples 1 to 40 are listed in Table 3. The physical data of intermediate compounds of compound of each Example was listed in Table 4. In Table 4, for example, Example No. 1-1 refers to Step 1 of Example 1.

TABLE 3

| Example No. | IR (cm$^{-1}$) | NMR (ppm) (no mark: 300MHz, *: 270MHz) | melting point (° C.) |
|---|---|---|---|
| 1 | KBr: 2227, 1510, 1454, 1228, 829 | DMSO-d$_6$: 7.74(2H, d, J=8Hz), 7.45(2H, d, J=8Hz), 6.74(2H, d, J=9Hz), 6.65(2H, d, J=9Hz), 4.40(1H, br.s), 3.61(2H, s), 2.87–2.79 (2H, m), 2.66–2.46(4H, m), 2.40–2.29(2H, m), 1.73–1.60(2H, m), 1.54–1.43(2H, m) | 95.4–99.8 |
| 2 | KBr: 2233, 1608, 1510, 1252, 1045, 829 | CDCl$_3$: 7.58(2H, d, J=8Hz), 7.32(2H, d, J=8Hz), 7.30(2H, d, J=9Hz), 6.90(2H, d, J=9Hz), 4.63(2H, s), 3.81(2H, s), 2.94–2.84 (2H, m), 2.81–2.72(2H, m), 2.70–2.61(2H, m), 2.50(2H, ddd, J=11, 11, 3Hz), 2.13(1H, br.s), 1.87–1.69(4H, m) | 148.7–150.3 |
| 3 | KBr: 2225, 1711, 1606, 1282, 1259, 1167, | CDCl$_3$: 8.00(2H, d, J=9Hz), 7.58(2H, d, J=8Hz), 7.32(2H, d, J=8Hz), 6.93(2H, d, J=9Hz), 3.89(3H, s), 3.88(2H, s), 2.94–2.85 (2H, m), 2.82–2.73(2H, m), 2.70–2.62(2H, m), 2.51(2H, ddd, J=11, 10, 4Hz), 2.11(1H, br.s), 1.88–1.72(4H, m) | 118.6–120.6 |
| 5 | KBr: 2229, 1664, 1606, 1419, 1261 | DMSO-d$_6$: 7.87–7.78(3H, m), 7.73(2H, d, J=8Hz), 7.44(2H, d, J=8Hz), 7.17(1H, br.s), 6.96(2H, d, J=9Hz), 4.53(1H, br. s), 3.79(2H, s), 2.88–2.78(2H, m), 2.69–2.31(6H, m), 1.73–1.48(4H, m) | 192.1–193.2 |
| 6 | KBr: 2229, 1593, 1344, 1263, 1111 | CDCl$_3$*: 8.21(2H, d, J=9Hz), 7.58(2H, d, J=8Hz), 7.33(2H, d, J=8Hz), 6.99(2H, d, J=9Hz), 3.92(2H, s), 2.94–2.84(2H, m), 2.83–2.73(2H, m), 2.71–2.61(2H, m), 2.56–2.43(2H, m), 1.96(1H, br.s), 1.86–1.75(4H, m) | 134.7–156.7 |
| 7 | KBr: 2227, 1608, 1510, 1234, 827 | CD$_3$OD: 7.73(2H, d, J=8Hz), 7.52(2H, d, J=8Hz), 6.80(2H, d, J=9Hz), 6.71(2H, d, J=9Hz), | 253.0–255.6 |

TABLE 3-continued

| Example No. | IR (cm$^{-1}$) | NMR (ppm) (no mark: 300MHz, *: 270MHz) | melting point (° C.) |
|---|---|---|---|
|  |  | 3.81(2H, s), 3.65–3.58(2H, m), 3.48–3.34(4H, m), 3.25–3.15(2H, m), 2.12(2H, ddd, J=14, 14, 4Hz), 2.00–1.90(2H, m) |  |
| 8 | KBr: 3359, 2229, 1608, 1514, 1248 | CD$_3$OD: 7.73(2H, d, J=8Hz), 7.52(2H, d, J=8Hz), 7.28(2H, d, J=9Hz), 6.94(2H, d, J=9Hz), 4.53(2H, s), 3.89(2H, s), 3.66–3.55 (2H, m), 3.50–3.34(4H, m), 3.26–3.14(2H, m), 2.13(2H, ddd, J=14, 14, 4Hz), 2.03–1.90(2H, m) | 189.2–192.3 |
| 9 | KBr: 3230, 2549, 2225, 1705, 1606, 1288, 1259 | CD$_3$OD: 7.98(2H, d, J=9Hz), 7.73(2H, d, J=8Hz), 7.52(2H, d, J=8Hz), 7.05(2H, d, J=9Hz), 3.98(2H, s), 3.87(3H, s), 3.57–3.46(2H, m), 3.43–3.32(4H, m), 3.23–3.14(2H, m), 2.18–2.04(2H, m), 2.02–1.93 (2H, m) | 183.7–189.7 |
| 10 | KBr: 3330, 2227, 1676, 1606, 1408, 1263 | CD$_3$OD: 7.86(2H, d, J=9Hz), 7.73(2H, d, J=8Hz), 7.53(2H, d, J=8Hz), 7.04(2H, d, J=9Hz), 3.98(2H, s), 3.64–3.52(2H, m), 3.48–3.34(4H, m), 3.26–3.16(2H, m), 2.23–2.07(2H, m), 2.04–1.93 (2H, m) | 251.0–254.9 |
| 11 | KBr: 3338, 2227, 1593, 1510, 1342, 1269 | CD$_3$OD: 8.24(2H, d, J=9Hz), 7.73(2H, d, J=8Hz), 7.53(2H, d, J=8Hz), 7.14(2H, d, J=9Hz), 4.04(2H, s), 3.61–3.50(2H, m), 3.46–3.33(4H, m), 3.24–3.16(2H, m), 2.18–1.95(4H, m) | 219.6–221.3 |
| 12 | KBr: 2935, 2227, 1707, 1606, 1257, 1165 | CD$_3$OD: 7.99(2H, d, J=9Hz), 7.73(2H, d, J=8Hz), 7.53(2H, d, J=8Hz), 7.04(2H, d, J=9Hz), 3.99(2H, s), 3.63–3.53(2H, m), 3.50–3.36(4H, m), 3.25–3.16(2H, m), 2.21–2.07(2H, m), 2.05–1.95 (2H, m) | 239.5–242.2 |
| 13 | KBr: 3309, 2229, 1604, 1543, 1363, 1246 | DMSO-d$_6$*: 7.88(2H, d, J=9Hz), 7.74(2H, d, J=8Hz), 7.45(2H, d, J=8Hz), 7.02(2H, d, J=9Hz), 4.55(1H, br.s), 3.82(2H, s), 2.88–2.80 (2H, m), 2.69–2.33(6H, m), 1.73–1.50(4H, m) | 208.4 (dec.) |
| 14 | KBr: 3211, 2231, 1606, 1572, 1520, 1383, 787 | CD$_3$OD*: 7.81(2H, d, J=9Hz), 7.66(2H, d, J=8Hz), 7.45(2H, d, J=8Hz), 6.80(2H, d, J=9Hz), 3.47(2H, s), 3.13–2.70(8H, m), 3.11(3H, s), 1.95–1.80(2H, m), 1.77–1.66(2H, m) | 220.0 (dec.) |
| 15 | KBr: 3400, 2229, 1556, 1379, 768 | CD$_3$OD: 7.68(2H, d, J=8Hz), 7.49–7.43 (3H, m), 7.30–7.26(1H, m), 7.19(1H, dd, J=8, 8Hz), 6.95–6.89 (1H, m), 3.44(2H, s), 3.37–3.25 (2H, m), 3.20–3.00(6H, m), 3.07(3H, s), 2.02–1.77(4H, m) | 181.9–189.1 |
| 16 | KBr: 3400, 2227, 1591, 1502, 1308, 1113 | CDCl$_3$: 8.11(2H, d, J=9Hz), 7.55(2H, d, J=8Hz), 7.26(2H, d, J=8Hz), 7.14(2H, d, J=9Hz), 3.75(2H, s), 3.01(3H, s), 2.83–2.75 (2H, m), 2.56–2.43(4H, m), 2.35–2.25(2H, m), 2.12–2.02(2H, m), 1.88–1.78(2H, m) | 98.3–108.1 |
| 17 | KBr: 3400, 2229, 1612, 1508, 1205, 827 | CD$_3$OD: 7.82(2H, d, J=9Hz), 7.69(2H, d, J=8Hz), 7.50(2H, d, J=8Hz), 6.96(2H, d, J=9Hz), 3.58–3.46 (2H, m), 3.53(2H, s), 3.45–3.27 (4H, m), 3.25–3.14(2H, m), 3.13(3H, s), 2.14–1.85(4H, m) | 159.7–171.8 |
| 19 | KBr: 3400, 2227, 1606, 1458, 1375, 708 | CD$_3$OD*: 7.93(1H, d, J=8Hz), 7.70(2H, d, J=8Hz), 7.60–7.54(2H, m), 7.49(2H, d, J=8Hz), 7.36–7.28 (1H, m), 3.44–3.09(8H, m), 3.40(2H, s), 3.00(3H, s), 1.91–1.79 (4H, m) | 106.5–116.2 |

TABLE 3-continued

| Example No. | IR (cm⁻¹) | NMR (ppm) (no mark: 300MHz, *: 270MHz) | melting point (° C.) |
|---|---|---|---|
| 20 | — | CDCl₃: 7.89(2H, d, J=9Hz), 7.58(2H, d, J=8Hz), 7.31(2H, d, J=8Hz), 6.82(2H, d, J=9Hz), 3.86(3H, s), 3.42(2H, s), 3.11(3H, s), 2.91–2.74(4H, m), 2.68–2.59 (2H, m), 2.45–2.33(2H, m), 1.83–1.63(4H, m), 1.50(1H, s) | — |
| 21 | — | CDCl₃*: 7.84(2H, d, J=9Hz), 7.57(2H, d, J=8Hz), 7.31(2H, d, J=8Hz), 6.80(2H, d, J=9Hz), 3.40(2H, s), 3.09(3H, s), 2.91–2.72 (4H, m), 2.67–2.58(2H, m), 2.44–2.31(2H, m), 1.83–1.60(4H, m), 1.57(9H, s), 1.49(1H, s) | — |
| 24 | KBr: 3435, 2233, 1604, 1522, 1408, 1383 | CD₃OD: 7.80(2H, d, J=9Hz), 7.64(2H, d, J=8Hz), 7.42(2H, d, J=8Hz), 6.77(2H, d, J=9Hz), 3.40(2H, s), 3.08(3H, s), 2.94–2.75 (4H, m), 2.67–2.59(2H, m), 2.51–2.40(2H, m), 1.82–1.60(4H, m) | 265.1 (dec.) |
| 25 | — | CDCl₃*: 7.89(2H, d, J=9Hz), 7.53–7.35 (4H, m), 6.83(2H, d, J=9Hz), 3.86(3H, s), 3.42(2H, s), 3.11(3H, s), 2.88–2.74(4H, m), 2.66–2.58 (2H, m), 2.44–2.33(2H, m), 1.83–1.63(4H, m), 1.50(1H, br.s) | — |
| 26 | — | CDCl₃*: 7.88(2H, d, J=9Hz), 7.64–7.58 (1H, m), 7.56–7.47(1H, m), 7.33–7.25(2H, m), 6.82(2H, d, J=9Hz), 3.86(3H, s), 3.42(2H, s), 3.10(3H, s), 3.08–3.00(2H, m), 2.87–2.63(4H, m), 2.45(2H, ddd, J=12, 12, 3Hz), 1.85–1.50(4H, m) | — |
| 27 | — | CD₃OD: 7.94(2H, d, J=9Hz), 7.85(2H, d, J=9Hz), 7.58(2H, d, J=9Hz), 6.86(2H, d, J=9Hz), 3.58–3.26 (6H, m), 3.56(2H, s), 3.23–3.12 (2H, m), 3.15(3H, s), 3.11(3H, s), 2.03–1.84(4H, m) | — |
| 28 | — | CD₃OD: 7.85–7.77(2H, m), 7.34–7.17 (5H, m), 6.84–6.76(2H, m), 3.55–2.82(8H, m), 3.48(2H, s), 3.11(3H, s), 1.95–1.70(4H, m) | — |
| 29 | KBr: 3151, 2225, 1660, 1601, 1385, 1194 | CD₃OD*: 7.85(2H, d, J=9Hz), 7.72(2H, d, J=8Hz), 7.50(2H, d, J=8Hz), 6.86(2H, d, J=9Hz), 3.59–3.26 (6H, m), 3.56(2H, s), 3.22–3.10 (2H, m), 3.15(3H, s), 2.08–1.82 (4H, m) | 146.1–148.9 |
| 30 | KBr: 3413, 3213, 2231, 1687, 1601, 1275, 760 | CD₃OD*: 7.71(2H, d, J=8Hz), 7.55–7.45 (3H, m), 7.36–7.29(1H, m), 7.27(1H, dd, J=8, 8Hz), 7.12–7.03 (1H, m), 3.58–3.24(6H, m), 3.49(2H, s), 3.23–3.11(2H, m), 3.10(3H, s), 2.08–1.84(4H, m) | 125.5–129.7 |
| 31 | KBr: 3294, 2563, 2225, 1676, 1608, 1232 | CD₃OD: 8.26(1H, dd, J=8, 1Hz), 7.98(1H, d, J=8Hz), 7.93–7.85(1H, m), 7.75–7.62(3H, m), 7.49(2H, d, J=8Hz), 3.85(2H, s), 3.56–3.47(2H, m), 3.35(3H, s), 3.43–3.13(6H, m), 2.05–1.92(2H, m), 1.85–1.75(2H, m) | 195.3–200.6 |
| 32 | KBr: 3400, 2229, 1612, 1508, 1383, 1207, 827 | CD3OD*: 7.83(2H, d, J=9Hz), 7.71(2H, d, J=9Hz), 7.50(2H, d, J=8Hz), 7.02(1H, d, J=9Hz), 3.61–3.48 (2H, m), 3.57(2H, s), 3.44–3.26 (4H, m), 3.23–3.11(2H, m), 3.17(3H, s), 2.11–1.85(4H, m) | amorphous |
| 33 | KBr: 3338, 2225, 1591, 1500, 1327, 1113 | CD₃OD: 8.12(2H, d, J=9Hz), 7.71(2H, d, J=8Hz), 7.47(2H, d, J=8Hz), 7.36(2H, d, J=9Hz), 3.74(2H, s), 3.57–3.47(2H, m), 3.40–3.28(2H, m), 3.18–3.07(2H, m), 3.13(3H, s), 2.97–2.84(2H, m), 2.68–2.58(2H, m), 2.10–1.95(2H, m) | 169.8–173.6 |
| 35 | KBr: 3377, 2227, 1685, | CD₃OD*: 7.78(2H, d, J=9Hz), 7.72(2H, d, J=9Hz), 7.50(2H, d, | 247.7–253.2 |

TABLE 3-continued

| Example No. | IR (cm$^{-1}$) | NMR (ppm) (no mark: 300MHz, *: 270MHz) | melting point (° C.) |
|---|---|---|---|
| | 1606, 1173 | J=9Hz), 6.69(2H, d, J=9Hz), 3.58–3.10 (10H, m), 2.05–1.85(4H, m) | |
| 36 | KBr: 3392, 2927, 1674, 1603, 1298, 1186, 1149 | CD$_3$OD: 7.94(2H, d, J=8Hz), 7.85(2H, d, J=9Hz), 7.58(2H, d, J=8Hz), 6.86(2H, d, J=9Hz), 3.56(2H, s), 3.55–3.26(6H, m), 3.23–3.13(2H, m), 3.15(3H, s), 3.11(3H, s), 2.03–1.84(4H, m) | 246.5–249.6 |
| 37 | KBr: 3386, 1603, 1523, 1383, 1277, 1190 | CD$_3$OD: 7.84(2H, d, J=9Hz), 7.37–7.22 (5H, m), 6.85(2H, d, J=9Hz), 3.54(2H, s), 3.52–3.43(2H, m), 3.37–3.21(4H, m), 3.14(3H, s), 3.11–3.03(2H, m), 2.07–1.93(2H, m), 1.91–1.82(2H, m) | 242.5–245.0 |
| 39 | KBr: 3435, 2229, 1676, 1603, 1188 | CD$_3$OD*: 7.85(2H, d, J=9Hz), 7.71(1H, m), 7.68–7.61(2H, m), 7.54(1H, dd, J=8, 8Hz), 6.86(2H, d, J=9Hz), 3.60–3.25(6H, m), 3.56(2H, s), 3.20–3.08(2H, m), 3.15(3H, s), 2.07–1.82(4H, m) | 166.8–176.4 |
| 40 | KBr: 2929, 2224, 1668, 1603, 1190 | CD$_3$OD*: 7.85(2H, d, J=9Hz), 7.79–7.64 (2H, m), 7.59–7.44(2H, m), 6.87(2H, d, J=9Hz), 3.62–3.51(2H, m), 3.57(2H, s), 3.49–3.26(6H, m), 3.15(3H, s), 2.09–1.85(4H, m) | 197.2–222.4 |

TABLE 4

| Example No. | IR (cm$^{-1}$) | NMR (ppm) (no mark: 300MHz, *: 270MHz) | melting point (° C.) |
|---|---|---|---|
| 1-1 | — | CDCl$_3$: 9.80(1H, t, J=2Hz), 7.67(2H, d, J=8Hz), 7.34(2H, d, J=8Hz), 3.82(2H, d, J=2Hz) | — |
| 1-2 | — | CDCl$_3$: 7.60(2H, d, J=8Hz), 7.34(2H, d, J=8Hz), 2.90(2H, dd, J=9, 6Hz), 2.82(4H, t, J=6Hz), 2.74(2H, dd, J=9, 6Hz), 2.47(4H, t, J=6Hz) | 79.0–79.6 |
| 1-3 | — | CDCl$_3$: 7.58(2 H, d, J=8Hz), 7.32(2H, d, J=8Hz), 2.88(2H, dd, J=9, 6Hz), 2.75–2.57(6H, m), 2.68(2H, s), 1.89(2H, ddd, J=13, 9, 4Hz), 1.55(2H, ddd, J=13, 5, 4Hz) | 74.2–75.1 |
| 2-1 | — | CDCl$_3$: 9.90(1H, s), 7.85(2H, d, J=9Hz), 7.58(2H, d, J=8Hz), 7.32(2H, d, J=8Hz), 7.03(2H, d, J=9Hz), 3.91(2H, s), 2.92–2.46(8H, m), 2.01(1H, br.s), 1.94–1.73(4H, m) | — |
| 4-1 | — | CDCl$_3$: 7.37–7.22(5H, m), 3.56(2H, s), 2.68–2.50(4H, m), 2.65(2H, s), 1.84(2H, ddd, J=13, 8, 4Hz), 1.55(2H, ddd, J=13, 5, 4Hz) | — |
| 4-2 | — | CDCl$_3$: 7.34–7.22(5H, m), 3.53(2H, s), 3.47(2H, s), 2.64(2H, ddd, J=12, 4, 4Hz), 2.36(2H, ddd, J=12, 7, 7Hz), 1.63(4H, dd, J=7, 4Hz) | 86.6–88.2 |
| 4-3 | — | CDCl$_3$*: 7.59(2H, d, J=9Hz), 7.36–7.23 (5H, m), 6.97(2H, d, J=9Hz), 3.86(2H, s), 3.56(2H, s), 2.74–2.63 (2H, m), 2.50–2.37(2H, m), 1.96(1H, br.s), 1.85–1.71(4H, m) | — |
| 4-4 | — | DMSO-d$_6$: 7.87(2H, d, J=9Hz), 7.35–7.21 (5H, m), 7.02(2H, d, J=9Hz), 4.55(1H, br.s), 3.82(2H, s), 3.48(2H, s), 2.60–2.27(4H, m), 1.74–1.63(2H, m), 1.60–1.50(2H, m) | 131.1–132.3 |
| 4-5 | — | CDCl$_3$: 7.99(2H, d, J=9Hz), 7.35–7.24 (5H, m), 6.92(2H, d, J=9Hz), 3.89(3H, s), 3.86(2H, s), 3.56(2H, | |

TABLE 4-continued

| Example No. | IR (cm$^{-1}$) | NMR (ppm) (no mark: 300MHz, *: 270MHz) | melting point (° C.) |
|---|---|---|---|
| 4-6 | — | s), 2.73–2.66(2H, m), 2.50–2.38 (2H, m), 1.82–1.71(4H, m) CDCl$_3$: 7.99(2H, d, J=9Hz), 6.93(2H, d, J=9Hz), 3.89(3H, s), 3.86(2H, s), 3.05(2H, ddd, J=12, 10, 4Hz), 2.90(2H, ddd, J=12, 4, 4Hz), 1.79–1.62(4H, m) | — |
| 5-1 | — | DMSO-d$_6$ + CDCl$_3$*: 7.85(2H, d, J=9Hz), 7.75(1H, br.s), 7.02–6.90(3H, m), 4.56(1H, br.s), 3.80(2H, s), 3.04–2.90(2H, m), 2.88–2.78(2H, m), 1.77–1.55(4H, m) | — |
| 6-1 | — | CDCl$_3$: 8.21(2H, d, J=9Hz), 7.36–7.22 (5H, m), 6.98(2H, d, J=9Hz), 3.91(2H, s), 3.56(2H, s), 2.73–2.67 (2H, m), 2.49–2.38(2H, m), 1.97(1H, br.s), 1.86–1.72(4H, m) | — |
| 6-2 | — | CDCl$_3$: 8.21(2H, d, J=9Hz), 6.99(2H, d, J=9Hz), 3.91(2H, s), 3.05(2H, ddd, J=12, 10, 4Hz), 2.92(2H, ddd, J=12, 4, 4Hz), 1.83–1.59 (4H, m) | — |
| 15-1 | — | CDCl$_3$: 8.76(0.4H, d, J=11Hz), 8.43(0.6H, d, J=2Hz), 8.06(0.6H, dd, J=2, 1Hz), 7.95(0.6H, ddd, J=8, 2, 1Hz), 7.90–7.77(0.4H, m), 7.87(0.4H, ddd, J=8, 1, 1Hz), 7.82(0.6H, ddd, J=8, 1, 1Hz), 7.78(0.4H, dd, J=2, 1Hz), 7.45(0.4H, dd, J=8, 6Hz), 7.43(0.6H, dd, J=8, 8Hz), 7.37(0.6H, br.s), 7.32–7.25(0.4H, m), 3.94(1.2H, s), 3.93(1.8H, s) | — |
| 15-2 | — | CDCl$_3$*: 7.46(1H, ddd, J=8, 1, 1Hz), 7.33(1H, dd, J=2, 1Hz), 7.27(1H, dd, J=8, 8Hz), 6.84(1H, ddd, J=8, 2, 1Hz), 2.89(3H, s) | — |
| 17-1 | — | CDCl$_3$: 7.44(2H, d, J=9Hz), 6.56(2H, d, J=9Hz), 4.26(1H, br.s), 2.88(3H, d, J=5Hz) | — |
| 17-2 | — | DMSO-d$_6$*: 7.76(2H, d, J=9Hz), 6.67(2H, d, J=9Hz), 6.42–6.31(1H, m), 2.74(3H, d, J=5Hz) | — |
| 20-1 | — | CDCl$_3$: 8.84(0.4H, d, J=11Hz), 8.44(0.6H, d, J=1Hz), 8.05(0.8H, d, J=9Hz), 8.03(1.2H, d, J=9Hz), 7.98–7.88(0.4H, m), 7.64(1.2H, d, J=9Hz), 7.39(0.6H, br.s), 7.13(0.8H, d, J=9Hz), 3.92(1.2H, s), 3.91(1.8H, s) | — |
| 21-1 | — | CDCl$_3$: 7.83(2H, d, J=9Hz), 6.54(2H, d, J=9Hz), 4.12(1H, br.s), 2.88(3H, d, J=5Hz), 1.57(9H, s) | — |
| 22-1 | — | CDCl$_3$: 8.83(0.4H, d, J=11Hz), 8.43(0.6H, d, J=2Hz), 8.28–8.16 (0.4H, m), 7.99(0.8H, d, J=9Hz), 7.97(1.2H, d, J=9Hz), 7.61(1.2H, d, J=9Hz), 7.54(0.6H, br.s), 7.11(0.8H, d, J=9Hz), 1.60(3.6H, s), 1.59(5.4H, s) | — |
| 22-2 | — | CDCl$_3$*: 7.81(2H, d, J=9Hz), 7.58(2H, d, J=8Hz), 7.31(2H, d, J=8Hz), 6.60(2H, d, J=9Hz), 4.43–4.34 (1H, m), 3.19(2H, d, J=6Hz), 2.92–2.55(6H, m), 2.50–2.35(2H, m), 1.78–1.66(4H, m), 1.56(9H, s), 1.52(1H, s) | — |
| 23-1 | — | CDCl$_3$: 7.86(2H, d, J=9Hz), 7.58(2H, d, J=8Hz), 7.31(2H, d, J=8Hz), 6.62(2H, d, J=9Hz), 4.45(1H, t, J=6Hz), 3.85(3H, s), 3.19(2H, d, J=6Hz), 2.92–2.83(2H, m), 2.78–2.60(4H, m), 2.49–2.37 (2H, m), 1.78–1.69(4H, m), 1.52(1H, s) | — |

TABLE 4-continued

| Example No. | IR (cm$^{-1}$) | NMR (ppm) (no mark: 300MHz, *: 270MHz) | melting point (° C.) |
|---|---|---|---|
| 25-1 | — | CDCl$_3$*: 9.80(1H, t, J=2Hz), 7.64–7.41 (4H, m), 3.80(2H, d, J=2Hz) | — |
| 25-2 | — | CDCl$_3$: 7.87(2H, d, J=9Hz), 7.35–7.22 (5H, m), 6.81(2H, d, J=9Hz), 3.85(3H, s), 3.52(2H, s), 3.40(2H, s), 3.08(3H, s), 2.75–2.66(2H, m), 2.31(2H, ddd, J=12, 12, 3Hz), 1.82–1.57(4H, m), 1.54(1H, s) | — |
| 25-3 | — | CDCl$_3$: 7.88(2H, d, J=9Hz), 6.82(2H, d, J=9Hz), 3.85(3H, s), 3.40(2H, s), 3.10(3H, s), 3.02–2.83 (4H, m), 1.70–1.57(4H, m) | — |
| 26-1 | — | CDCl$_3$*: 9.84(1H, t, J=1Hz), 7.72(1H, dd, J=8, 1Hz), 7.61(1H, ddd, J=8, 8, 1Hz), 7.43(1H, ddd, J=8, 8, 1Hz), 7.34(1H, dd, J=8, 1Hz), 4.02(2H, d, J=1Hz) | — |
| 27-1 | — | CDCl$_3$: 7.90(2H, d, J=8Hz), 7.89(2H, d, J=9Hz), 7.46(2H, d, J=8Hz), 6.81(2H, d, J=9Hz), 4.57–4.48 (1H, m), 3.86(3H, s), 3.82(2H, s), 3.77–3.67(1H, m), 3.51–3.32 (3H, m), 3.08(3H, s), 3.05(3H, s), 3.04–2.93(1H, m), 1.78–1.55 (3H, m), 1.52–1.36(1H, m) | — |
| 27-2 | KBr: 3489, 1687, 1610, 1298, 1188, 1149 | CDCl$_3$: 7.89(2H, d, J=9Hz), 7.86(2H, d, J=8Hz), 7.40(2H, d, J=8Hz), 6.82(2H, d, J=9Hz), 3.86(3H, s), 3.42(2H, s), 3.11(3H, s), 3.04(3H, s), 2.94–2.87(2H, m), 2.84–2.75(2H, m), 2.69–2.62(2H, m), 2.44–2.34(2H, m), 1.83–1.63 (4H, m) | 149.4–152.0 |
| 28-1 | — | CDCl$_3$: 7.86(2H, d, J=9Hz), 7.34–7.20 (5H, m), 6.75(2H, d, J=9Hz), 4.56–4.47(1H, m), 3.85(3H, s), 3.77–3.64(1H, m), 3.73(2H, s), 3.40–3.24(3H, m), 3.03(3H, s), 2.94(1H, ddd, J=13, 13, 3Hz), 1.70–1.46(3H, m), 1.27–1.13(1H, m) | — |
| 28-2 | KBr: 3460, 2947, 1676, 1606, 1298, 1190 | CDCl$_3$: 7.93(2H, d, J=9Hz), 7.33–7.26 (2H, m), 7.23–7.17(3H, m), 6.82(2H, d, J=9Hz), 3.85(3H, s), 3.42(2H, s), 3.10(3H, s), 2.88–2.77 (4H, m), 2.68–2.59(2H, m), 2.37(2H, ddd, J=12, 12, 3Hz), 1.86–1.63(4H, m), 1.57(1H, s) | 114.8–115.9 |

The structures of the compounds manufactured in the above-mentioned Examples are shown in Charts 1 to 3. In the abbreviations of the substituents used in the structures, Me- means methyl group, Et- means ethyl group and tBu- means tert-butyl group.

Chart 1

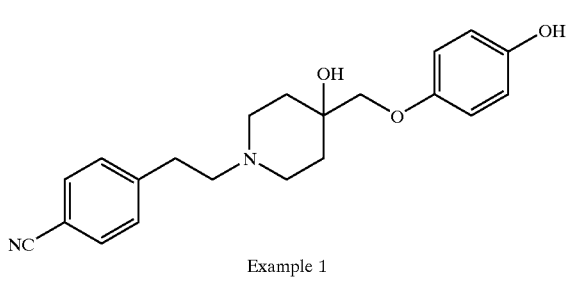

Example 1

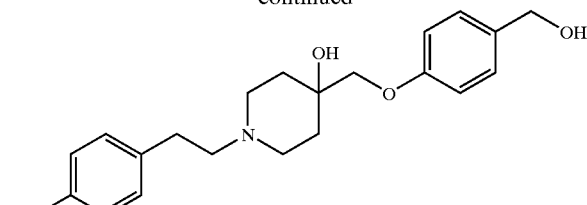

Example 2

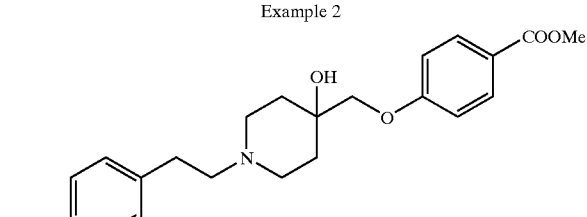

Example 3
Example 4

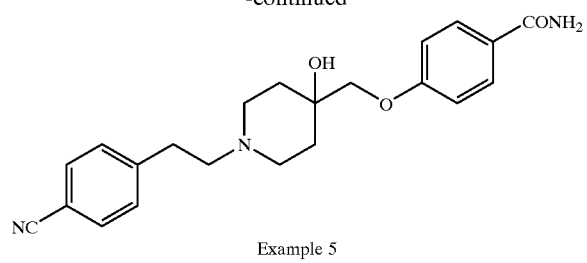

Example 5

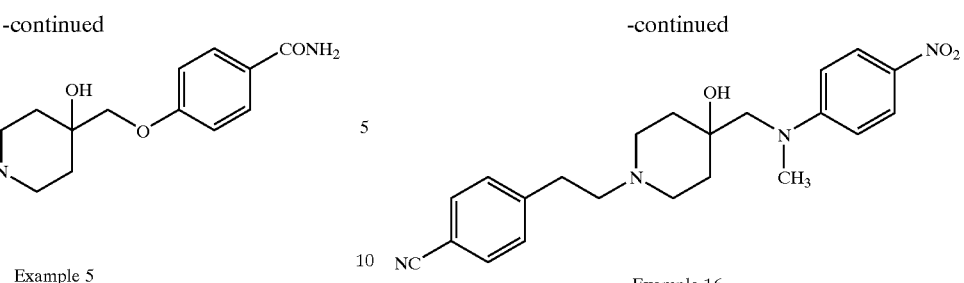

Example 16

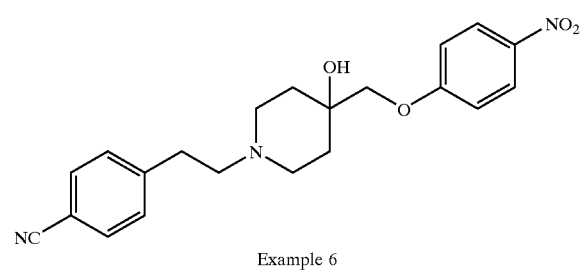

Example 6

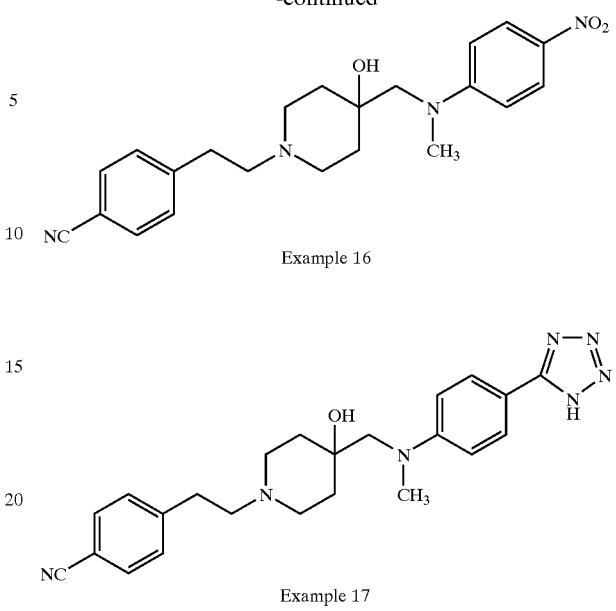

Example 17

Example 7 hydrochloride of compound of Example 1
Example 8 hydrochloride of compound of Example 2
Example 9 hydrochloride of compound of Example 3
Example 10 hydrochloride of compound of Example 5
Example 11 hydrochloride of compound of Example 6
Example 12 hydrochloride of compound of Example 13

Chart 2

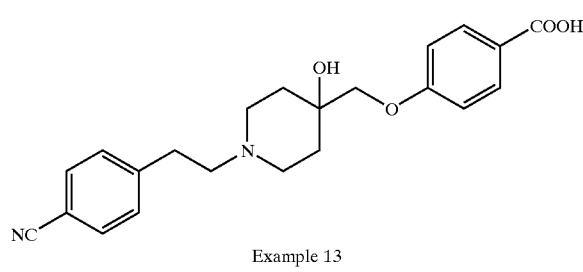

Example 13

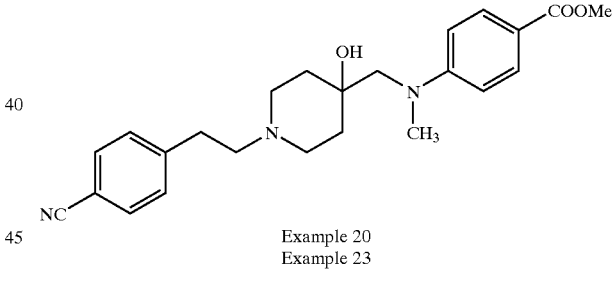

Example 19

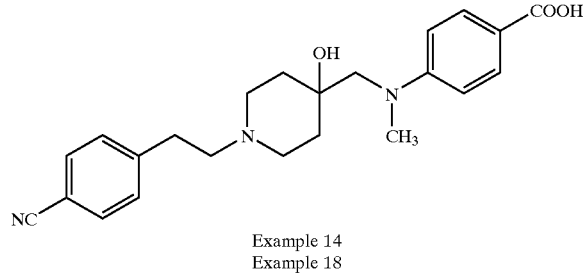

Example 14
Example 18

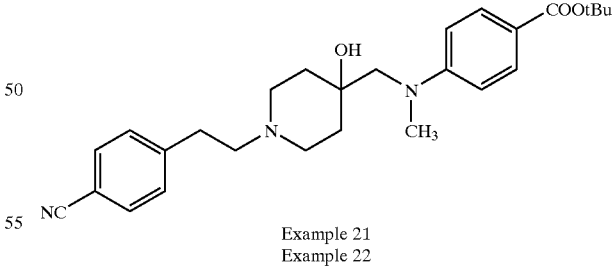

Example 20
Example 23

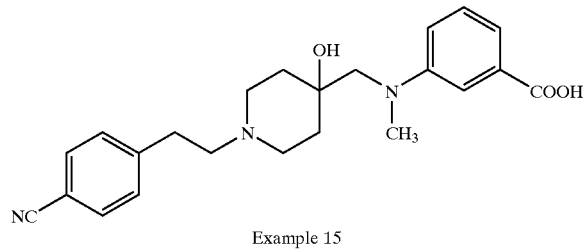

Example 15

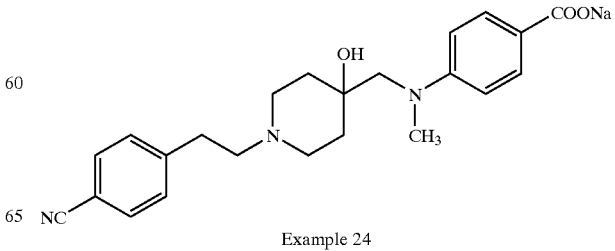

Example 21
Example 22

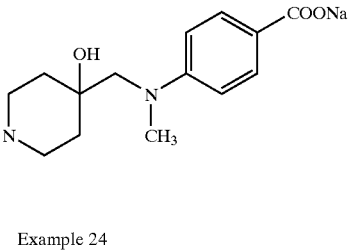

Example 24

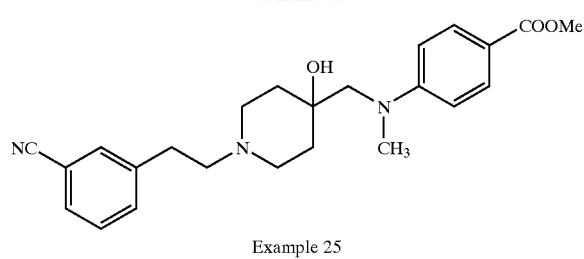

Example 25

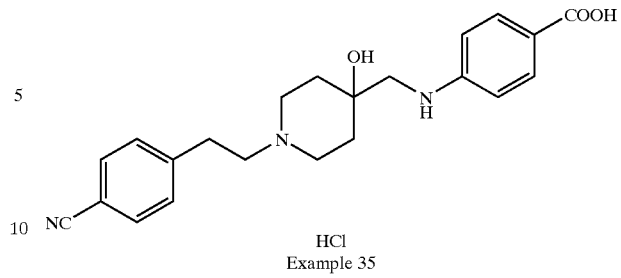

HCl
Example 35

Example 36 monohydrochloride of compound of Example 27

Example 37 monohydrochloride of compound of Example 28

Chart 3

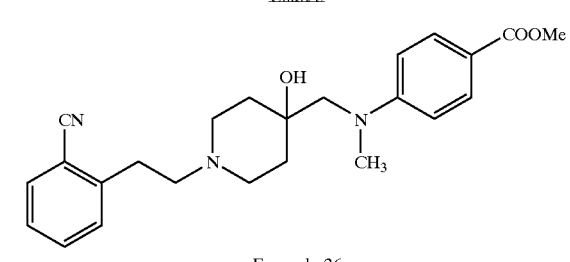

Example 26

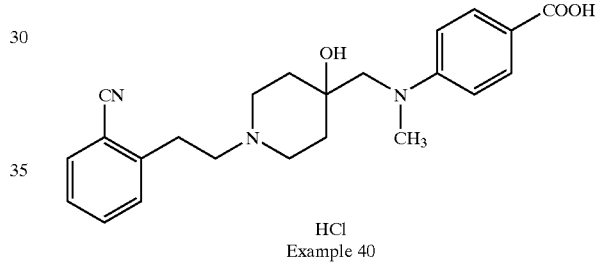

HCl
Example 39

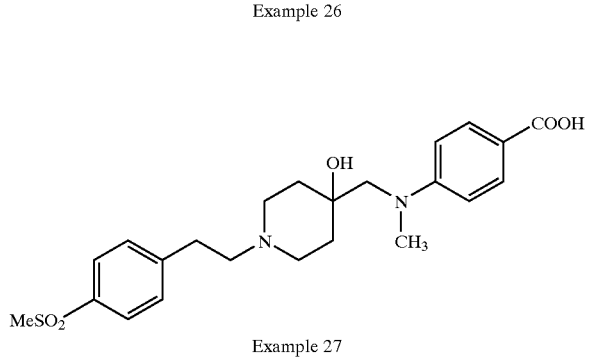

Example 27

Example 28

Example 29 monohydrochloride of compound of Example 14

Example 30 monohydrochloride of compound of Example 15

Example 31 monohydrochloride of compound of Example 19

Example 32 monohydrochloride of compound of Example 17

Example 33 monohydrochloride of compound of Example 16

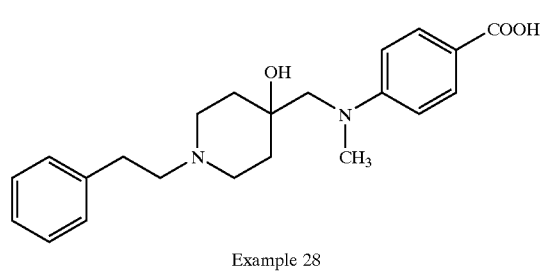

HCl
Example 40

Compounds shown in Charts 4 to 11 are synthesized in the similar way with the above-mentioned Examples.

CHART 4

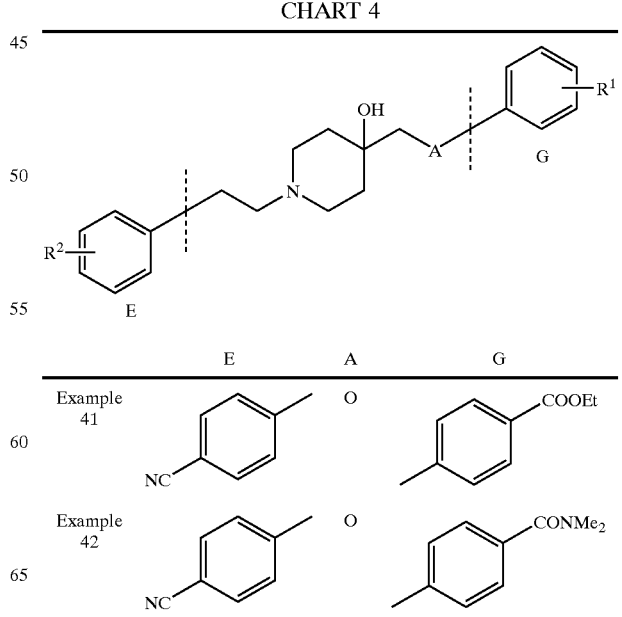

CHART 4-continued

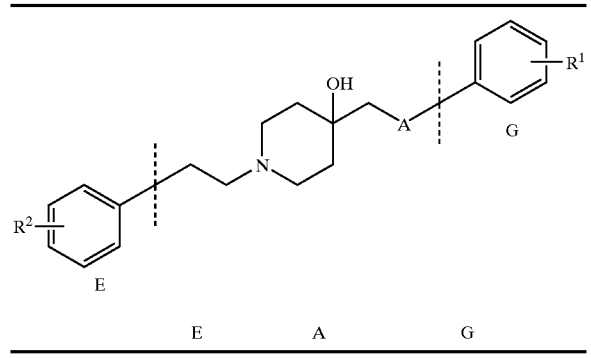

| | E | A | G |
|---|---|---|---|
| Example 43 | NC-C6H4- | O | -C6H4-CONEt2 |
| Example 44 | NC-C6H4- | O | -C6H4-tetrazole |
| Example 45 | NC-C6H4- | NMe | -C6H4-COOEt |
| Example 46 | NC-C6H4- | NMe | -C6H4-CONMe2 |
| Example 47 | NC-C6H4- | NMe | -C6H4-CONEt2 |

CHART 5

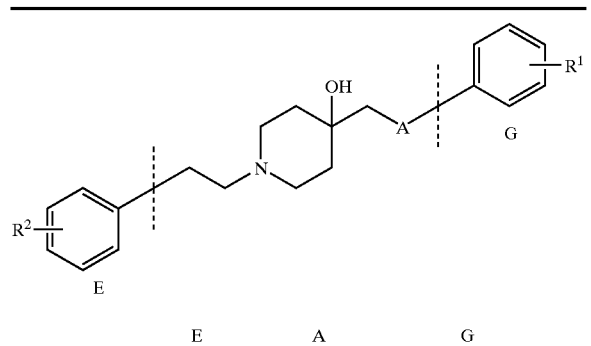

| | E | A | G |
|---|---|---|---|
| Example 48 | NC-C6H4- | NH | -C6H4-NO2 |
| Example 49 | NC-C6H4- | NH | -C6H4-COOEt |

CHART 5-continued

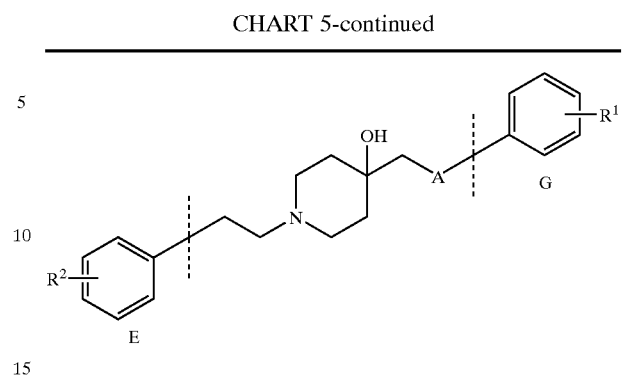

| | E | A | G |
|---|---|---|---|
| Example 50 | NC-C6H4- | NH | -C6H4-CONH2 |
| Example 51 | NC-C6H4- | NH | -C6H4-CONMe2 |
| Example 52 | NC-C6H4- | NH | -C6H4-CONEt2 |
| Example 53 | NC-C6H4- | NH | -C6H4-tetrazole |

CHART 6

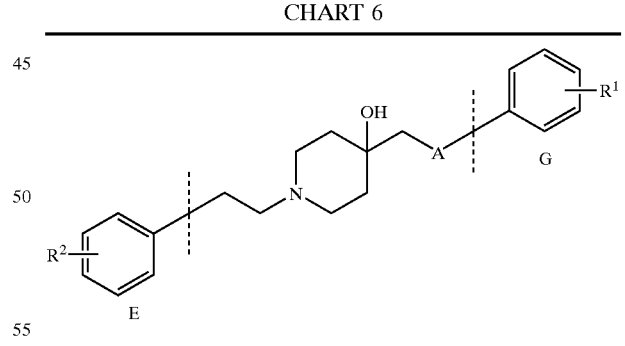

| | E | A | G |
|---|---|---|---|
| Example 54 | MeO2S-C6H4- | O | -C6H4-NO2 |
| Example 55 | MeO2S-C6H4- | O | -C6H4-COOMe |

CHART 6-continued
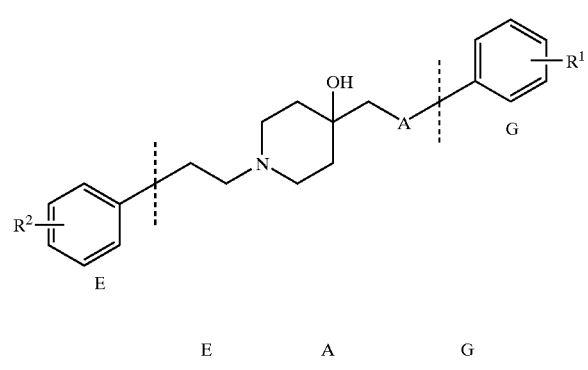
| | E | A | G |
|---|---|---|---|
| Example 56 | 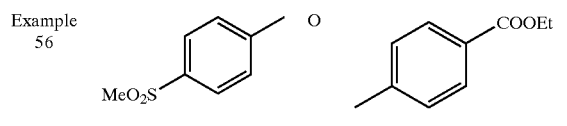 | O | 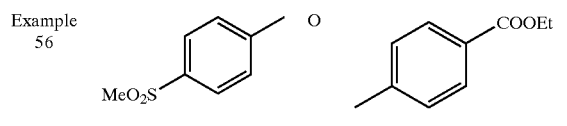 COOEt |
| Example 57 | 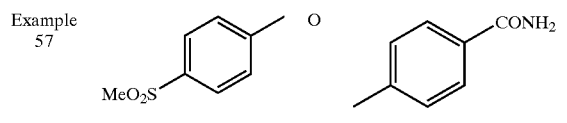 | O | 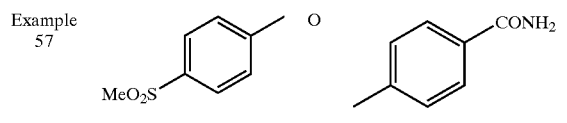 CONH₂ |
| Example 58 | 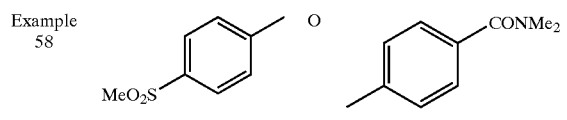 | O | 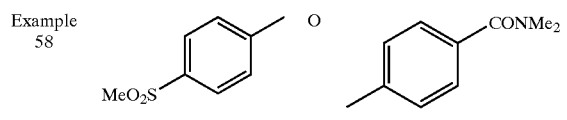 CONMe₂ |
| Example 59 | 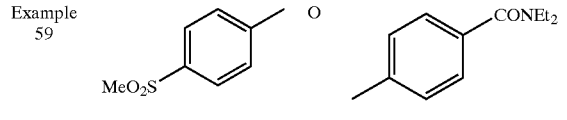 | O | 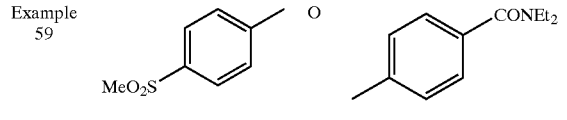 CONEt₂ |
| Example 60 | 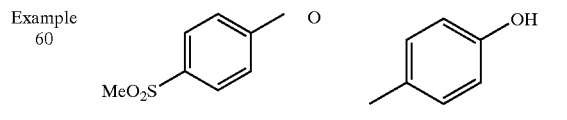 | O | 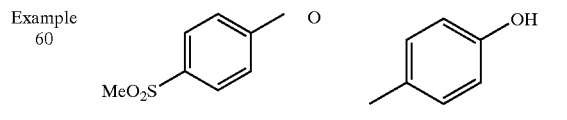 OH |
| Example 61 | 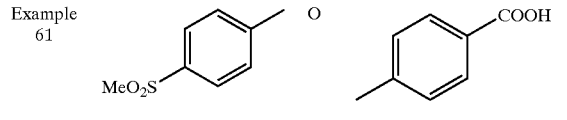 | O | 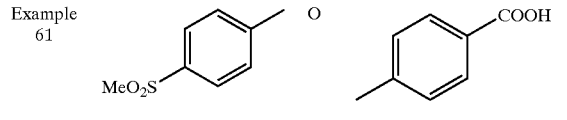 COOH |
| Example 62 | 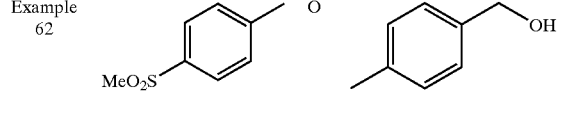 | O | 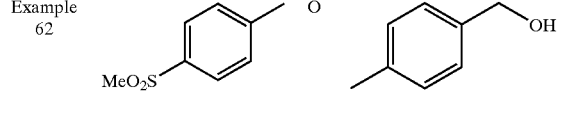 OH |
| Example 63 | 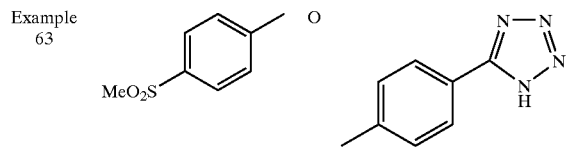 | O | 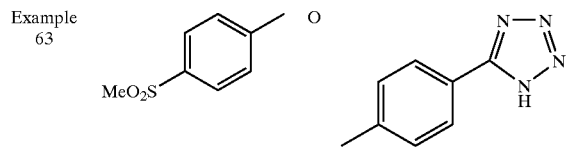 (tetrazole) |
CHART 7
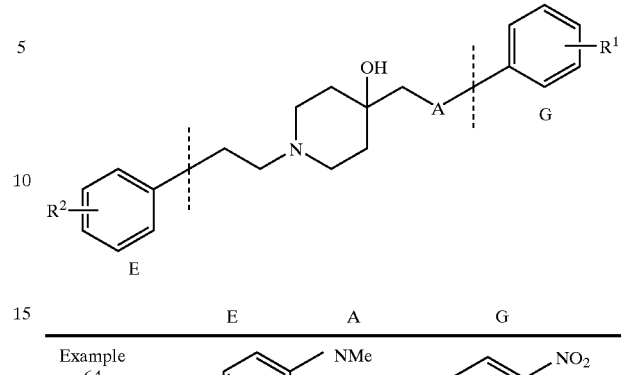
| | E | A | G |
|---|---|---|---|
| Example 64 | 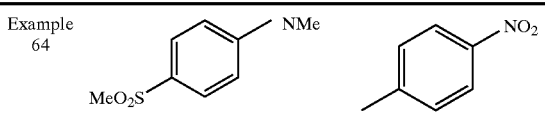 | NMe | NO₂ |
| Example 65 | 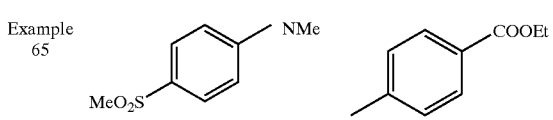 | NMe | COOEt |
| Example 66 | 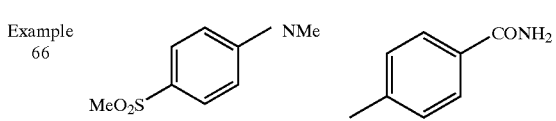 | NMe | CONH₂ |
| Example 67 | 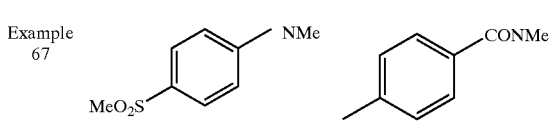 | NMe | CONMe₂ |
| Example 68 | 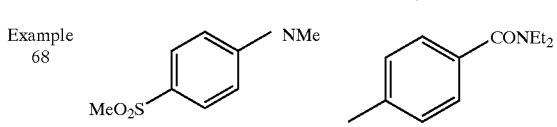 | NMe | CONEt₂ |
| Example 69 | 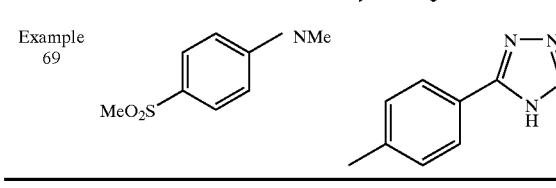 | NMe | (tetrazole) |
CHART 8
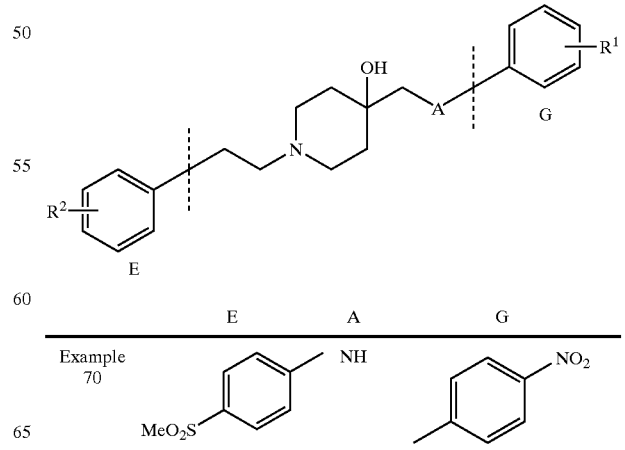
| | E | A | G |
|---|---|---|---|
| Example 70 | MeO₂S–C₆H₄– | NH | –C₆H₄–NO₂ |

CHART 8-continued
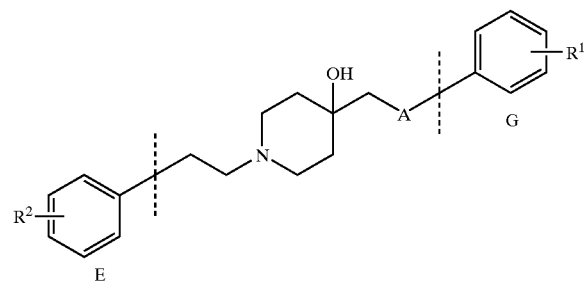
| | E | A | G |
|---|---|---|---|
| Example 71 | 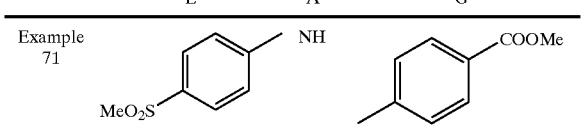 | NH | COOMe |
| Example 72 | 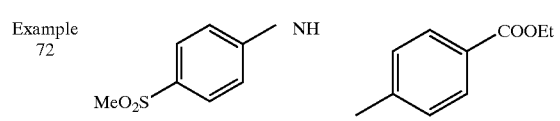 | NH | COOEt |
| Example 73 | 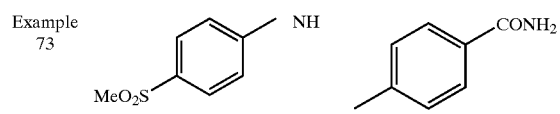 | NH | CONH$_2$ |
| Example 74 | 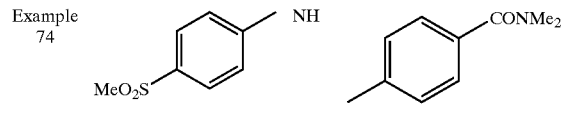 | NH | CONMe$_2$ |
| Example 75 | 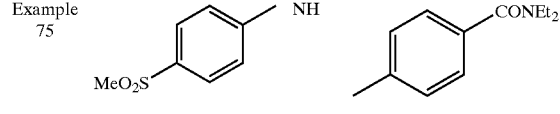 | NH | CONEt$_2$ |
| Example 76 | 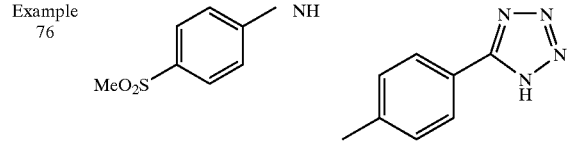 | NH | (tetrazole-phenyl) |
CHART 9
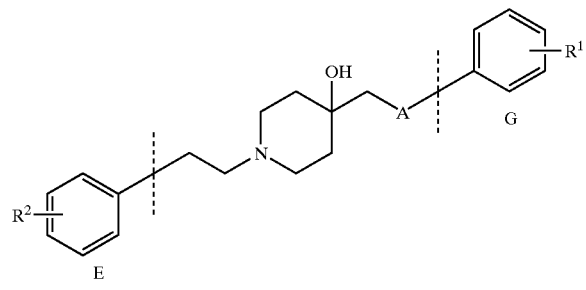
| | E | A | G |
|---|---|---|---|
| Example 77 | 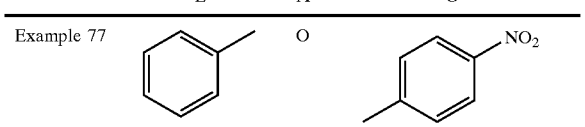 | O | NO$_2$ |
CHART 9-continued
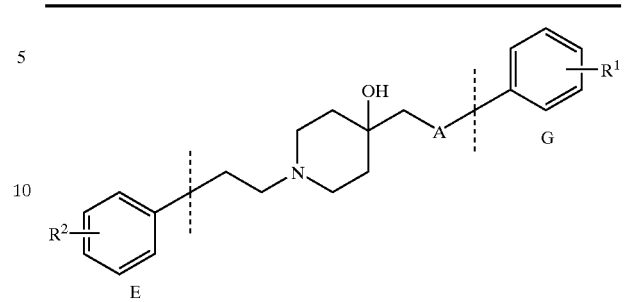
| | E | A | G |
|---|---|---|---|
| Example 78 | 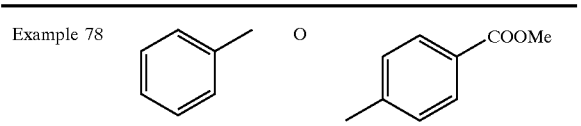 | O | COOMe |
| Example 79 | 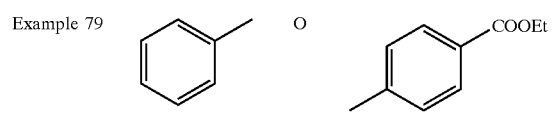 | O | COOEt |
| Example 80 | 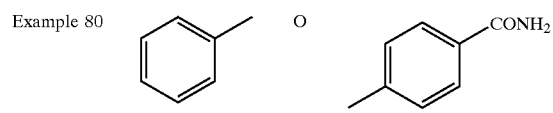 | O | CONH$_2$ |
| Example 81 | 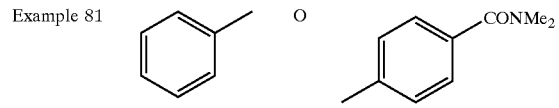 | O | CONMe$_2$ |
| Example 82 | 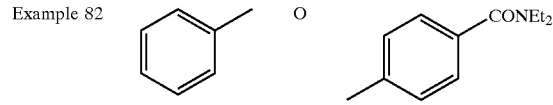 | O | CONEt$_2$ |
| Example 83 | 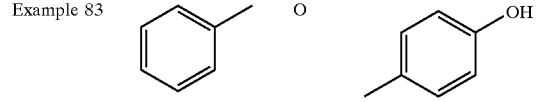 | O | OH |
| Example 84 | 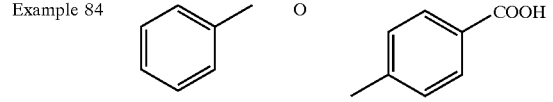 | O | COOH |
| Example 85 | 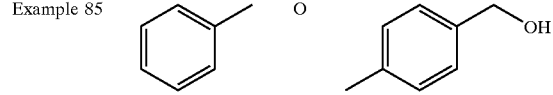 | O | CH$_2$OH |
| Example 86 | 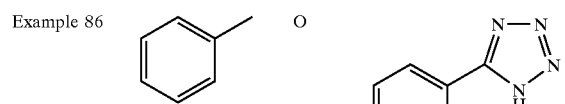 | O | (tetrazole-phenyl) |

CHART 10

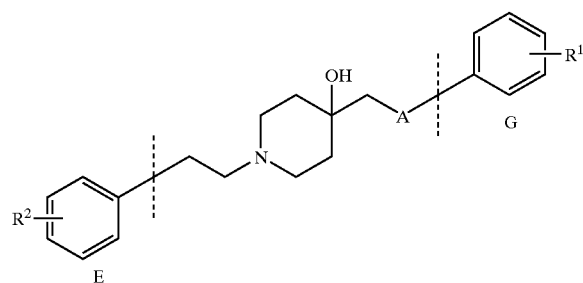

| | E | A | G |
|---|---|---|---|
| Example 87 | phenyl | NMe | 4-NO₂-phenyl |
| Example 88 | phenyl | NMe | 4-COOEt-phenyl |
| Example 89 | phenyl | NMe | 4-CONH₂-phenyl |
| Example 90 | phenyl | NMe | 4-CONMe₂-phenyl |
| Example 91 | phenyl | NMe | 4-CONEt₂-phenyl |
| Example 92 | phenyl | NMe | 4-(1H-tetrazol-5-yl)-phenyl |

CHART 11

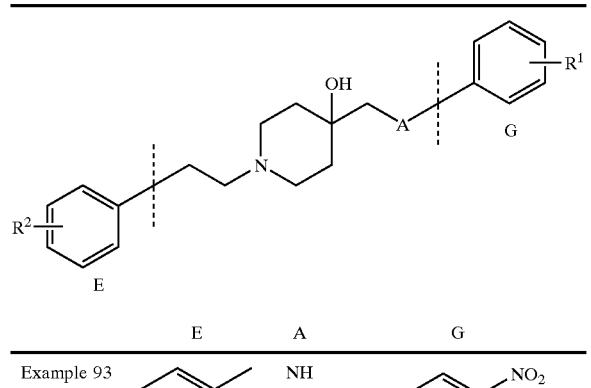

| | E | A | G |
|---|---|---|---|
| Example 93 | phenyl | NH | 4-NO₂-phenyl |

CHART 11-continued

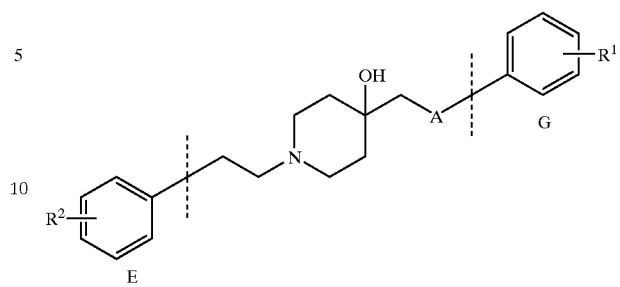

| | E | A | G |
|---|---|---|---|
| Example 94 | phenyl | NH | 4-COOMe-phenyl |
| Example 95 | phenyl | NH | 4-COOEt-phenyl |
| Example 96 | phenyl | NH | 4-CONH₂-phenyl |
| Example 97 | phenyl | NH | 4-CONMe₂-phenyl |
| Example 98 | phenyl | NH | 4-CONEt₂-phenyl |
| Example 99 | phenyl | NH | 4-(1H-tetrazol-5-yl)-phenyl |

Structures of intermediate compounds of the compounds of Examples 1 to 40 are shown in Charts 12 to 14. Example 1-1 is a compound obtained in Step 1 of Example 1. In the abbreviations of the substituents used in the structures, Me- means methyl group and tBu- means tert-butyl group.

Chart 12

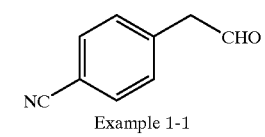

Example 1-1

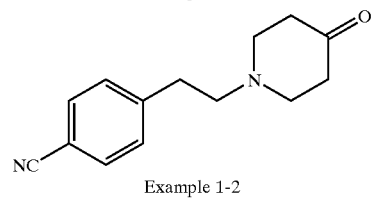

Example 1-2

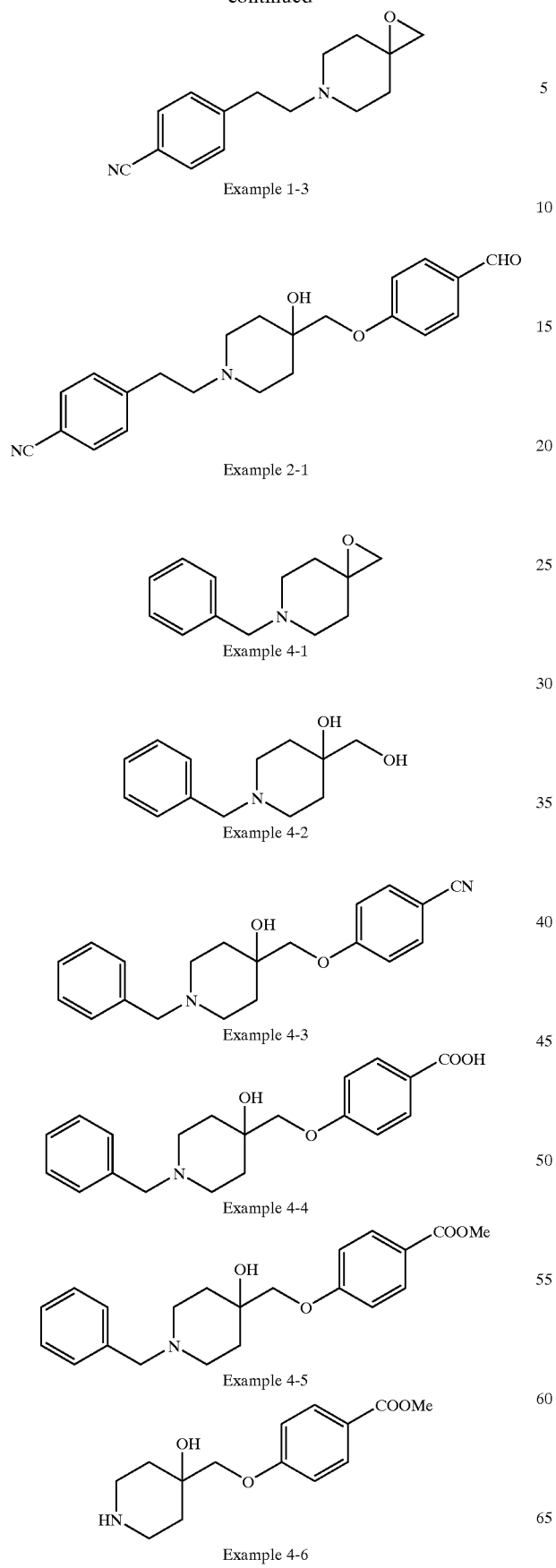
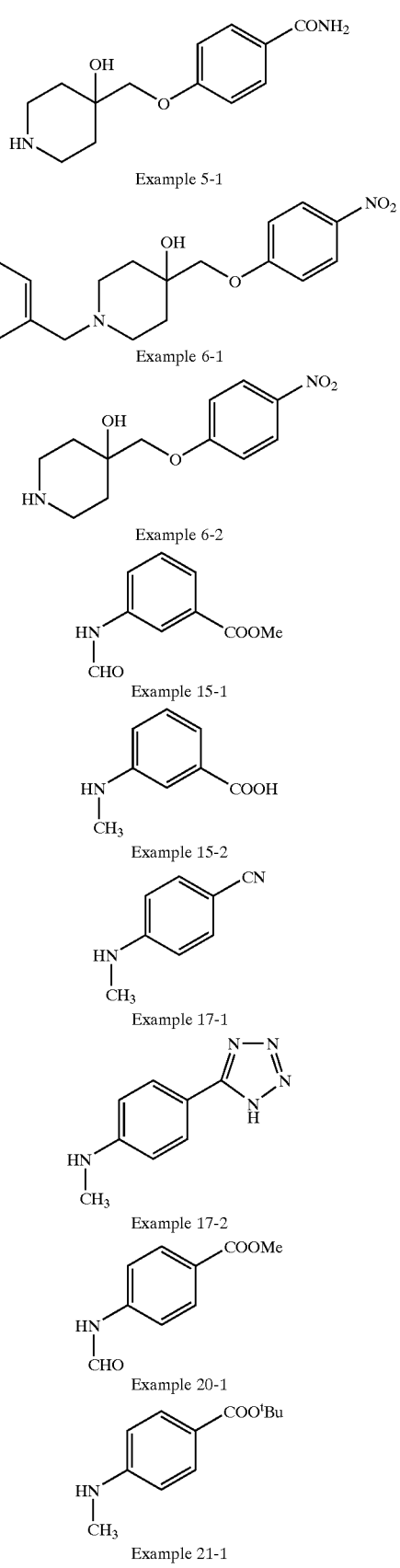

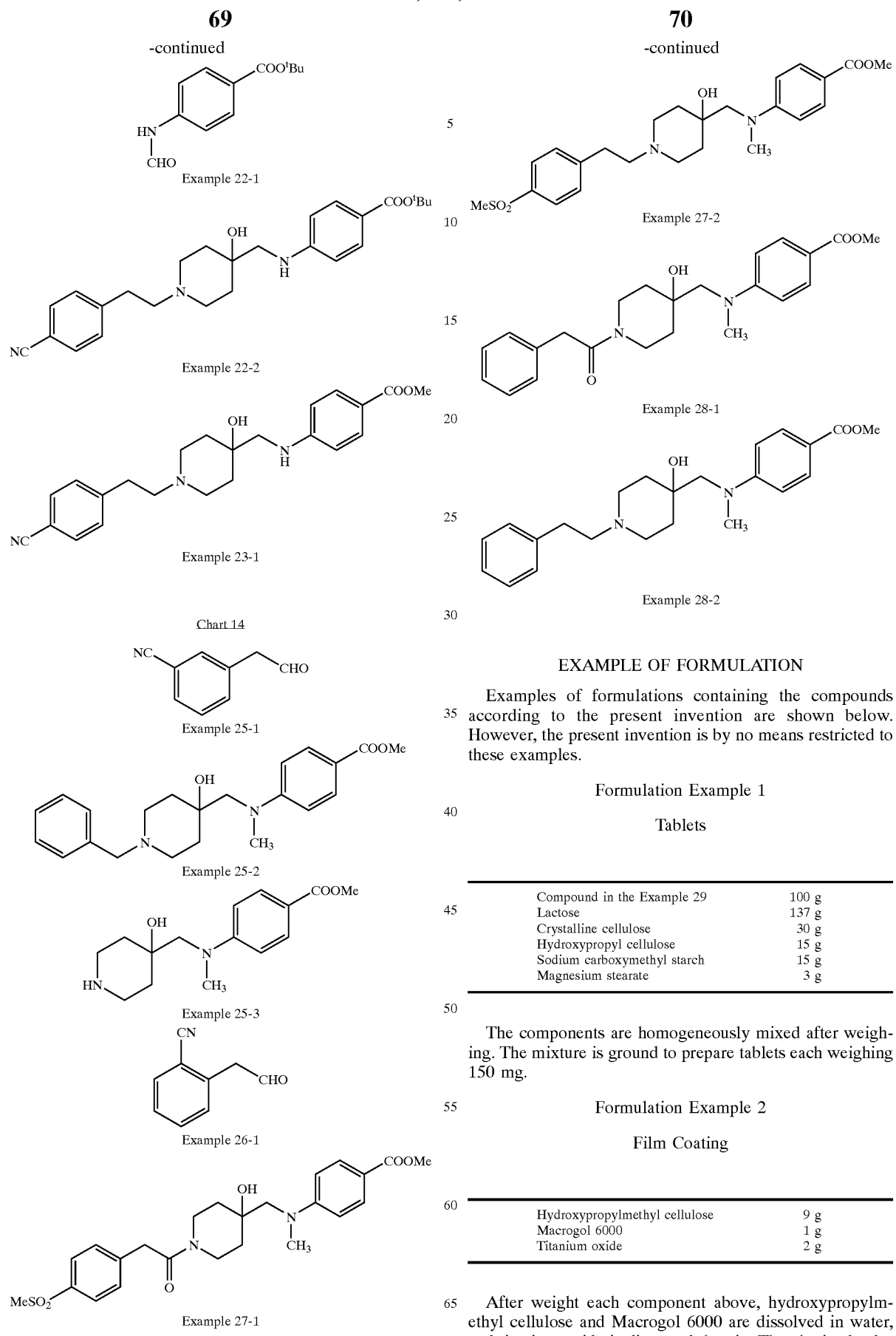

EXAMPLE OF FORMULATION

Examples of formulations containing the compounds according to the present invention are shown below. However, the present invention is by no means restricted to these examples.

Formulation Example 1

Tablets

| | |
|---|---|
| Compound in the Example 29 | 100 g |
| Lactose | 137 g |
| Crystalline cellulose | 30 g |
| Hydroxypropyl cellulose | 15 g |
| Sodium carboxymethyl starch | 15 g |
| Magnesium stearate | 3 g |

The components are homogeneously mixed after weighing. The mixture is ground to prepare tablets each weighing 150 mg.

Formulation Example 2

Film Coating

| | |
|---|---|
| Hydroxypropylmethyl cellulose | 9 g |
| Macrogol 6000 | 1 g |
| Titanium oxide | 2 g |

After weight each component above, hydroxypropylmethyl cellulose and Macrogol 6000 are dissolved in water, and titanium oxide is dispersed therein. The obtained solution is film-coated to the tablet 300 g of Formulation Example 1 to obtain film-coated tablet.

Formulation Example 3

Capsules

| | |
|---|---|
| Compound in the Example 12 | 50 g |
| Lactose | 435 g |
| Magnesium stearate | 15 g |

The components above are homogeneously mixed after weighing. 300 mg each of the mixture is filled in an appropriate hard capsule by using a capsule-encapsulating machine to prepare a capsule drug.

Formulation Example 4

Capsules

| | |
|---|---|
| Compound in the Example 29 | 100 g |
| Lactose | 63 g |
| Corn starch | 25 g |
| Hydroxypropyl cellulose | 10 g |
| talc | 2 g |

After weighing each component above, the compound in the Example 29, lactose and corn starch are homogeneously mixed. An aqueous solution of hydroxypropyl cellulose is added to this mixture, and granules are prepared by a wet granulation method. The granules are homogeneously mixed with talc and filled in an appropriate hard capsule each weighing 200 mg.

Formulation Example 5

Powder

| | |
|---|---|
| Compound in the Example 32 | 200 g |
| Lactose | 790 g |
| Magnesium stearate | 10 g |

A powder containing 20% of the effective ingredient is prepared by mixing each component homogeneously after weighing.

Formulation Example 6

Granules and Fine Granules

| | |
|---|---|
| Compound in the Example 32 | 100 g |
| Lactose | 200 g |
| Crystalline cellulose | 100 g |
| Partly pregelatinized starch | 50 g |
| Hydroxypropyl cellulose | 50 g |

After weighing each component above, the compound in the Example 32, lactose, crystalline cellulose and partly pregelatinized starch are homogeneously mixed. An aqueous solution of hydroxypropyl cellulose (HPC) is added to this mixture, and granules or fine granules are prepared by a wet granulation method. These are dried, and formed into granules or fine granules.

Formulation Example 7

Injection

| | |
|---|---|
| Compound in the Example 24 | 2 g |
| Propylene glycol | 200 g |
| Distilled water for injection | proper volume |

The compound in the example 24 is dissolved in propylene glycol after weighing each component. Aseptic water for injection is added to make a total volume of 1000 mL, and 5 mL each of the aqueous solution is dispensed in a 10 mL ampoule after aseptic filtration, followed by fusing the ampoule to prepare an injection.

Formulation Example 8

Suppository

| | |
|---|---|
| Compound in the Example 27 | 100 g |
| Polyethylene glycol 1500 | 180 g |
| Polyethylene glycol 4000 | 720 g |

After grinding the compound in the Example 27 in a mortar into fine powder, suppositories each weighing 1 g are prepared by hot-melting.

INDUSTRIAL APPLICABILITY

The compounds of the present invention can be used for the treatment of pain accompanying painful diseases such as hyperalgesia, allodynia, spontaneous painful sensation, for example, for the treatment and prevention of pain accompanying central neuropathy (for example, neuropathy resulting from spinal cord injury), peripheral neuropathy (for example, reflex sympathetic dystrophy (RSD)), herpes zoster infection during its acute phase, postherpetic neuralgia (PHN), diabetic neuropathy, trigeminal neuralgia, postoperative neuralgia, cancer pain, low back pain-related neuropathy, pain state subsequent to spinal cord injury, thalamic pain, limb pain, causalgia, reflex sympathetic nerve atrophy, chronic headache, toothache, periarthritis scapulohumeralis, osteoarthritis, arthritis, rheumatism, etc., but its effective use is not limited to the above. Or, the inhibitor may be used for preventing or retarding the aggravation of symptoms accompanying those chronic diseases which otherwise may appear in the course of time.

The compounds of the present invention will be effective not only for the treatment of pain diseases, etc., but also for the treatment of convulsion, epilepsy, dementia (cerebrovascular and dementia senilis), cerebral infarction during its acute phase, cerebral hemorrhage, transient cerebral ischemia, subarachnoidal hemorrhage, head trauma, after-effects subsequent to brain surgery, cerebral vascular disorders subsequent to cerebral arterial sclerosis, diseases accompanied by itching, irritable bowel syndrome (IBS), etc., but their use should not be limited to those diseases.

What is claimed is:

1. A compound represented by the following Formula (I):

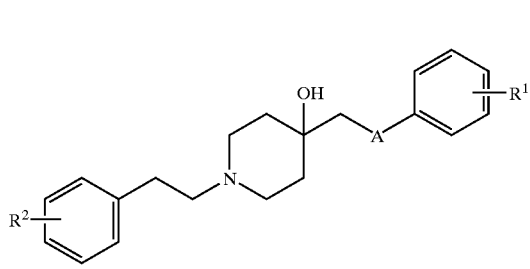

(I)

(wherein A represents oxygen atom or —NR³— (R³ represents hydrogen atom or lower alkyl group); R¹ represents nitro group, lower alkoxycarbonyl group, carbamoyl group unsubstituted or mono- or di-substituted by lower alkyl group, unprotected or protected hydroxyl group, unprotected or protected carboxyl group, lower alkyl group substituted by unprotected or protected hydroxyl group, or tetrazolyl group; and R² represents hydrogen atom, cyano group or lower allylsulfonyl group, provided that when A is —NR³—, it is excluded that R¹ represents unprotected or protected hydroxyl group or lower alkyl group substituted by unprotected or protected hydroxyl group), or its salt.

2. A compound or its salt claimed in claim 1 characterized in that R¹ represents nitro group, lower alkoxycarbonyl group, carbamoyl group unsubstituted or mono- or di-substituted by lower alkyl groups, unprotected or protected carboxyl group, or tetrazolyl group.

3. A compound or its salt claimed in claim 1 characterized in that R² represents cyano group.

4. A compound or its salt selected from

1-[2-(4-cyanophenyl)ethyl]-4-(4-nitrophenoxymethyl)piperidin-4-ol;

1-[2-(4-cyanophenyl)ethyl]-4-(4-hydroxyphenoxymethyl)piperidin-4-ol;

4-(4-carbamoylphenoxymethyl)-1-[2-(4-cyanophenyl)ethyl]piperidin-4-ol;

methyl 4-{1-[2-(4-cyanophenyl)ethyl]-4-hydroxypiperidin-4-ylmethoxy}benzoate;

4-{1-[2-(4-cyanophenyl)ethyl]-4-hydroxypiperidin-4-ylmethoxy}benzoic acid;

1-[2-(4-cyanophenyl)ethyl]-4-(4-hydroxymethylphenoxylmethyl)piperidin-4-ol;

methyl 4-({1-[2-(4-cyanophenyl)ethyl]-4-hydroxypiperidin-4-ylmethyl}methylamino)benzoate;

4-({1-[2-(4-cyanophenyl)ethyl]-4-hydroxypiperidin-4-ylmethyl}methylamino)benzoic acid;

4-({1-[2-(3-cyanophenyl)ethyl]-4-hydroxypiperidin-4-ylmethyl}methylamino)benzoic acid;

4-({1-[2-(2-cyanophenyl)ethyl]-4-hydroxypiperidin-4-ylmethyl}methylamino)benzoic acid;

3-({1-[2-(4-cyanophenyl)ethyl]-4-hydroxypiperidin-4-ylmethyl}methylamino)benzoic acid;

2-({1-[2-(4-cyanophenyl)ethyl]-4-hydroxypiperidin-4-ylmethyl}methylamino)benzoic acid;

4-[2-(4-hydroxy-4-{[methyl(4-nitrophenyl)amino]methyl}piperidin-1-yl)ethyl]benzonitrile;

4-{2-[4-hydroxy-4-({methyl[-4-(1H-tetrazol-5-yl)phenyl]amino}methyl)piperidin-1-yl]ethyl}benzonitrile;

4-({1-[2-(4-cyanophenyl)ethyl]-4-hydroxypiperidin-4-ylmethyl}amino)benzoic acid;

4-({4-hydroxy-1-[2-(4-methanesulfonylphenyl)ethyl]piperidin-4-ylmethyl}methylamino)benzoic acid; and 4-[(4-hydroxy-1-phenethylpiperidin-4-ylmethyl)methylamino]benzoic acid.

5. A compound represented by the following Formula (II):

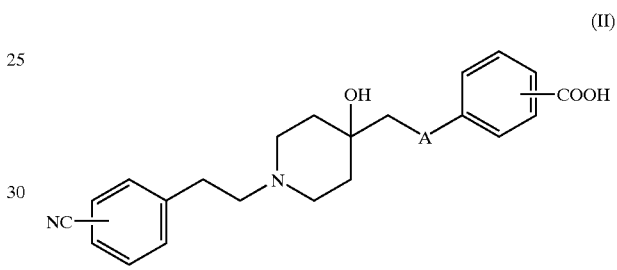

(II)

(wherein A represents oxygen atom or —NR³— (R³ represents hydrogen atom or lower alkyl group)) and its salt.

6. Pharmaceutical composition characterized by containing as active ingredient the compounds described in claim 1, or their salts.

7. Analgesic agent characterized by containing as active ingredient the compounds described in claim 1, or their salts.

8. Antiallodynia agent characterized by containing as active ingredient the compounds described in claim 1, or their salts.

9. Analgesic agent described in claim 7, wherein it is able to be orally administered to mammal.

10. Antiallodynia agent described in claim 8, wherein it is able to be orally administered to mammal.

* * * * *